(12) United States Patent
Stanimirovic et al.

(10) Patent No.: US 10,112,998 B2
(45) Date of Patent: Oct. 30, 2018

(54) INSULIN-LIKE GROWTH FACTOR 1 RECEPTOR-SPECIFIC ANTIBODIES AND USES THEREOF

(71) Applicant: National Research Council of Canada, Ottawa (CA)

(72) Inventors: Danica Stanimirovic, Ottawa (CA); Kristin Kemmerich, Ottawa (CA); Arsalan S. Haqqani, Kanata (CA); Traian Sulea, Kirkland (CA); Mehdi Arbabi-Ghahroudi, Ottawa (CA); Bernard Massie, Laval (CA); Rénald Gilbert, Montréal (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 15/123,781

(22) PCT Filed: Dec. 4, 2014

(86) PCT No.: PCT/CA2014/000861
§ 371 (c)(1),
(2) Date: Sep. 6, 2016

(87) PCT Pub. No.: WO2015/131257
PCT Pub. Date: Sep. 11, 2015

(65) Prior Publication Data
US 2017/0022277 A1    Jan. 26, 2017

Related U.S. Application Data

(60) Provisional application No. 61/948,818, filed on Mar. 6, 2014.

(51) Int. Cl.
| C07K 16/28 | (2006.01) |
| A61K 47/50 | (2017.01) |
| C07K 16/46 | (2006.01) |
| A61K 49/00 | (2006.01) |
| G01N 33/74 | (2006.01) |
| G01N 33/574 | (2006.01) |
| A61K 47/68 | (2017.01) |
| A61K 39/00 | (2006.01) |

(52) U.S. Cl.
CPC ...... *C07K 16/2863* (2013.01); *A61K 47/6849* (2017.08); *A61K 49/0002* (2013.01); *A61K 49/0058* (2013.01); *C07K 16/465* (2013.01); *G01N 33/57492* (2013.01); *G01N 33/74* (2013.01); *A61K 2039/505* (2013.01); *C07K 2317/22* (2013.01); *C07K 2317/24* (2013.01); *C07K 2317/35* (2013.01); *C07K 2317/51* (2013.01); *C07K 2317/52* (2013.01); *C07K 2317/565* (2013.01); *C07K 2317/569* (2013.01); *C07K 2317/64* (2013.01); *C07K 2317/70* (2013.01); *C07K 2317/77* (2013.01); *C07K 2317/92* (2013.01); *C07K 2317/94* (2013.01); *G01N 2333/71* (2013.01); *G01N 2333/72* (2013.01); *G01N 2570/00* (2013.01); *G01N 2800/28* (2013.01)

(58) Field of Classification Search
None
See application file for complete search history.

(56) References Cited

U.S. PATENT DOCUMENTS

| | | | |
|---|---|---|---|
| 5,693,761 A | 12/1997 | Queen et al. | |
| 5,766,886 A | 6/1998 | Studnicka et al. | |
| 5,821,123 A | 10/1998 | Studnicka | |
| 5,859,205 A | 1/1999 | Adair et al. | |
| 5,869,619 A | 2/1999 | Studnicka | |
| 6,054,297 A | 4/2000 | Carter et al. | |
| 6,180,370 B1 | 1/2001 | Queen et al. | |
| 7,741,446 B2 | 6/2010 | Pardridge et al. | |
| 7,943,129 B2 * | 5/2011 | Muruganandam | C07K 16/00 424/130.1 |
| 8,257,705 B2 * | 9/2012 | Tanha | C07K 16/00 424/133.1 |
| 8,524,231 B2 * | 9/2013 | Dreier | C07K 16/2866 424/133.1 |
| 2004/0161738 A1 | 8/2004 | Muruganandam et al. | |
| 2005/0142141 A1 * | 6/2005 | Pardridge | A61K 47/48561 424/178.1 |
| 2008/0171055 A1 | 7/2008 | Pardridge et al. | |
| 2009/0252681 A1 * | 10/2009 | Laeremans | C07K 16/00 424/9.1 |
| 2010/0290985 A1 | 11/2010 | Pardridge et al. | |
| 2011/0110935 A1 * | 5/2011 | Pardridge | C07K 16/18 424/133.1 |
| 2011/0262460 A1 | 10/2011 | Shusta et al. | |

(Continued)

FOREIGN PATENT DOCUMENTS

| EP | 519596 A1 | 12/1992 |
| EP | 626390 A1 | 11/1994 |

(Continued)

OTHER PUBLICATIONS

Swiss-Prot Accession No. P08069, https://www.ncbi.nlm.nih.gov/protein/124240/?report=genpept, accessed Mar. 29, 2017.*

(Continued)

*Primary Examiner* — Marianne P Allen
(74) *Attorney, Agent, or Firm* — Wolf, Greenfield & Sacks, P.C.

(57) ABSTRACT

The blood-brain barrier (BBB) prevents transport of molecules larger than 500 Daltons from blood to brain. Receptor-mediated transcytosis (RMT) facilitates transport across the BBB of specific molecules that bind receptors on brain endothelial cells that form the BBB. An insulin-like growth factor 1 receptor (IGF 1R)-binding antibody or fragment thereof is identified that transmigrates the BBB by RMT. The antibody or fragment is used to deliver a cargo molecule across the BBB, wherein the cargo molecule may be a therapeutic or detectable agent. The antibody is a camelid VHH, prepared by immunizing a llama with a 933-amino acid IGF 1R polypeptide. Humanized forms of the camelid VHH are also generated.

11 Claims, 16 Drawing Sheets
Specification includes a Sequence Listing.

(56) References Cited

U.S. PATENT DOCUMENTS

| | | | | |
|---|---|---|---|---|
| 2011/0294748 | A1* | 12/2011 | Diem | C07K 7/08 |
| | | | | 514/21.4 |
| 2011/0300140 | A1* | 12/2011 | Dreier | C07K 16/2866 |
| | | | | 424/133.1 |
| 2012/0171120 | A1 | 7/2012 | Dennis et al. | |
| 2017/0015748 | A1 | 1/2017 | Stanimirovic et al. | |
| 2017/0015749 | A1 | 1/2017 | Stanimirovic et al. | |

FOREIGN PATENT DOCUMENTS

| | | |
|---|---|---|
| EP | 1943341 | 7/2008 |
| EP | 2029621 | 3/2009 |
| EP | 2197490 | 6/2010 |
| EP | 14884789 | 7/2017 |
| EP | 14884539 | 9/2017 |
| WO | WO 1995/004069 A1 | 2/1995 |
| WO | WO 2002/057445 A1 | 7/2002 |
| WO | WO 2003/046560 A2 | 6/2003 |
| WO | WO 2004/076670 A1 | 9/2004 |
| WO | WO 2007/000328 * | 1/2007 |
| WO | WO 2007/036021 A1 | 4/2007 |
| WO | WO 2007/143711 A2 | 12/2007 |
| WO | WO 2009/032782 A2 | 3/2009 |
| WO | WO 2011/044542 A1 | 4/2011 |
| WO | WO 2011/066721 A1 | 6/2011 |
| WO | WO 2011/127580 A1 | 10/2011 |
| WO | WO 2011/150061 A1 | 12/2011 |
| WO | WO 2013/106577 * | 7/2013 |
| WO | WO 2015/131257 A1 | 9/2015 |
| WO | WO 2015/131258 A1 | 9/2015 |

OTHER PUBLICATIONS

Abbott, Blood-brain barrier structure and function and the challenges for CNS drug delivery. J Inherit Metab Dis. May 2013;36(3):437-49. doi:10.1007/s10545-013-9608-0. Epub Apr. 23, 2013.

Abulrob et al., The blood-brain barrier transmigrating single domain antibody: mechanisms of transport and antigenic epitopes in human brain endothelial cells. J Neurochem. Nov. 2005;95(4):1201-14.

Alam et al., Strategy for effective brain drug delivery. Eur J Pharm Sci. Aug. 11, 2010;40(5):385-403. doi: 10.1016/j.ejps.May 3, 2010. Epub May 16, 2010.

Arbabi Ghahroudi et al., Selection and identification of single domain antibody fragments from camel heavy-chain antibodies. FEBS Lett. Sep. 15, 1997;414(3):521-6.

Arbabi-Ghahroudi et al., Aggregation-resistant VHs selected by in vitro evolution tend to have disulfide-bonded loops and acidic isoelectric points. Protein Eng Des Sel. Feb. 2009;22(2):59-66. doi: 10.1093/protein/gzn071. Epub Nov. 24, 2008.

Arbabi-Ghahroudi et al., Selection of non-aggregating VH binders from synthetic VH phage-display libraries. Methods Mol Biol. 2009;525:187-216, xiii. doi: 10.1007/978-1-59745554-1_10.

Atwal et al., A therapeutic antibody targeting BACE1 inhibits amyloid-fβ production in vivo. Sci Transl Med. May 25, 2011;3(84):84ra43. doi: 10.1126/scitranslmed.3002254.

Bell et al., Differential tumor-targeting abilities of three single-domain antibody formats. Cancer Lett. Mar. 1, 2010;289(1):81-90. doi: 10.1016/j.canlet.Aug. 3, 2009. Epub Aug. 28, 2009.

Bertrand et al., Transport characteristics of a novel peptide platform for CNS therapeutics. J Cell Mol Med. Dec. 2010;14(12):2827-39. doi: 10.1111/j.1582-4934.2009.00930.x.

Boado et al., Pharmacokinetics and brain uptake in the rhesus monkey of a fusion protein of arylsulfatase a and a monoclonal antibody against the human insulin receptor. Biotechnol Bioeng. May 2013;110(5):1456-65. doi: 10.1002/bit.24795. Epub Dec. 25, 2012.

Boado et al., The Trojan horse liposome technology for nonviral gene transfer across the blood-brain barrier. J Drug Deliv. 2011;2011:296151. doi:10.1155/2011/296151. Epub Nov. 16, 2011.

Broussau et al., Inducible packaging cells for large-scale production of lentiviral vectors in serum-free suspension culture. Mol Ther. Mar. 2008;16(3):500-7. doi: 10.1038/sj.mt.6300383. Epub Jan. 8, 2008.

Chang et al., Evaluation of a novel hexavalent humanized anti-IGF-1R antibody and its bivalent parental IgG in diverse cancer cell lines. PLoS ONE. 2012;7(8):e44235. https://doi.org/10.1371/journal.pone.0044235.

Chothia et al., Canonical structures for the hypervariable regions of immunoglobulins. J Mol Biol. Aug. 20, 1987;196(4):901-17.

Davies et al., Affinity improvement of single antibody VH domains:residues in all three hypervariable regions affect antigen binding. Immunotechnology. Sep. 1996;2(3):169-79.

De Kruif et al., Leucine zipper dimerized bivalent and bispecific scFv antibodies from a semi-synthetic antibody phage display library. J Biol Chem. Mar. 2, 1996;271(13):7630-4.

Demeule et al., Involvement of the low-density lipoprotein receptor-related protein in the transcytosis of the brain delivery vector angiopep-2. J Neurochem. Aug. 2008;106(4):1534-44. doi:10.1111/j.1471-4159.2008.05492.x. Epub May 19, 2008.

Doyle et al., Cloning, expression, and characterization of a single-domain antibody fragment with affinity for 15-acetyl-deoxynivalenol. Mol Immunol. Aug. 2008;45(14):3703-13. doi: 10.1016/j.molimm.Jun. 5, 2008. Epub Jul. 15, 2008.

Dumoulin et al., Single-domain antibody fragments with high conformational stability. Protein Sci. Mar. 2002;11(3):500-15.

Durocher et al., High-level and high-throughput recombinant protein production by transient transfection of suspension-growing human 293-EBNA1 cells. Nucleic Acids Res. Jan. 15, 2002;30(2):E9.

Eisenberg et al., Analysis of membrane and surface protein sequences with the hydrophobic moment plot. J Mol Biol. Oct. 15, 1984;179(1):125-42.

Erdlenbruch et al., Alkylglycerol opening of the blood-brain barrier to small and large fluorescence markers in normal and C6 glioma-bearing rats and isolated rat brain capillaries. Br J Pharmacol. Dec. 2003;140(7):1201-10. Epub Nov. 3, 2003.

Fenner et al., Rapid and reliable diagnostic algorithm for detection of Clostridium difficile. J Clin Microbiol. Jan. 2008;46(1):328-30. Epub Nov. 21, 2007.

Fu et al., Intravenous treatment of experimental Parkinson's disease in the mouse with an IgG-GDNF fusion protein that penetrates the blood-brain barrier. Brain Res. Sep. 17, 2010;1352:208-13. doi:10.1016/j.brainres.2010.06.059. Epub Jun. 30, 2010.

Gabathuler, Approaches to transport therapeutic drugs across the blood-brain barrier to treat brain diseases. Neurobiol Dis. Jan. 2010;37(1):48-57. doi:10.1016/j.nbd.Jul. 28, 2009.

Gaillet et al., High-level recombinant protein production in CHO cells using an adenoviral vector and the cumate gene-switch. Biotechnol Prog. Jan.-Feb. 2007;23(1):200-9.

Gaillet et al., High-level recombinant protein production in CHO cells using lentiviral vectors and the cumate gene-switch. Biotechnol Bioeng. Jun. 1, 2010;106(2):203-15. doi: 10.1002/bit.22698.

Gan et al., Gene delivery with viral vectors for cerebrovascular diseases. Front Biosci (Elite Ed). Jan. 1, 2013;5:188-203.

Garberg et al., In vitro models for the blood-brain barrier. Toxicol In Vitro. Apr. 2005;19(3):299-334.

Gergov et al., Simultaneous screening for 238 drugs in blood by liquid chromatography-ion spray tandem mass spectrometry with multiple-reaction monitoring. J Chromatogr B Analyt Technol Biomed Life Sci. Sep. 25, 2003;795(1):41-53.

Gombos et al., Clinical development of insulin-like growth factor receptor--1 (IGF-1R) inhibitors: at the crossroad? Invest New Drugs. Dec. 2012;30(6):2433-42. doi: 10.1007/s10637012-9811-0. Epub Mar. 14, 2012.

Gottesman et al., Biochemistry of multidrug resistance mediated by the multidrug transporter. Annu Rev Biochem. 1993;62:385-427.

Hamers-Casterman et al., Naturally occurring antibodies devoid of light chains. Nature. Jun. 3, 1993;363(6428):446-8.

Haqqani et al., Multiplexed evaluation of serum and CSF pharmacokinetics of brain-targeting single-domain antibodies using a NanoLC-SRM-ILIS method. Mol Pharm. May 6, 2013;10(5):1542-56. doi: 10.1021/mp3004995. Epub Dec. 6, 2012.

(56) References Cited

OTHER PUBLICATIONS

Hargreaves et al., Bradykinin is increased during acute and chronic inflammation: therapeutic implications. Clin Pharmacol Ther. Dec. 1988;44(6):613-21.

Heskamp et al., Optimization of IGF-1R SPECT/CT imaging using 111In-labeled F(ab')2 and Fab fragments of the monoclonal antibody R1507. Mol Pharm. Aug. 6, 2012;9(8):2314-21. doi: 10.1021/mp300232n. Epub Jul. 13, 2012.

Huang et al., A new approach for multiple sampling of cisternal cerebrospinal fluid in rodents with minimal trauma and inflammation. J Neurosci Methods. Dec. 1995;63(1-2):13-22.

Hussack et al., Engineered single-domain antibodies with high protease resistance and thermal stability. PLoS One. 2011;6(11):e28218. doi: 10.1371/journal.pone.0028218. Epub Nov. 30, 2011.

Hussack et al., Neutralization of Clostridium difficile toxin A with single-domain antibodies targeting the cell receptor binding domain. J Biol Chem. Mar. 18, 2011;286(11):8961-76. doi: 10.1074/jbc.M110.198754. Epub Jan. 7, 2011.

Iqbal et al., Integrated platform for brain imaging and drug delivery across the blood-brain barrier. Methods Mol Biol. 2011;686:465-81. doi: 10.1007/978-1-60761-938-3_24.

Iqbal et al., Kinetic analysis of novel mono- and multivalent VHH-fragments and their application for molecular imaging of brain tumours. Br J Pharmacol. Jun. 2010;160(4):1016-28. doi:10.1111/j.1476-5381.2010.00742.x.

Jespers et al., Aggregation-resistant domain antibodies selected on phage by heat denaturation. Nat Biotechnol. Sep. 2004;22(9):1161-5. Epub Aug. 8, 2004.

Kabat et al., Identical V region amino acid sequences and segments of sequences in antibodies of different specificities. Relative contributions of VH and VL genes, minigenes, and complementarity-determining regions to binding of antibody-combining sites. J Immunol. Sep. 1, 1991;147(5):1709-19.

Kim et al., Disulfide linkage engineering for improving biophysical properties of human VH domains. Protein Eng Des Sel. Oct. 2012;25(10):581-9. Epub Aug. 30, 2012.

Kornhuber et al., A method for repeated CSF sampling in the freely moving rat. J Neurosci Methods. Jul. 1986;17(1):63-8.

Kristensen et al., Specificity of insulin and insulin-like growth factor I receptors investigated using chimeric mini-receptors. Role of C-terminal of receptor alpha subunit. J Biol Chem. Dec. 24, 1999;274(52):37351-6.

Lampson, Monoclonal antibodies in neuro-oncology: Getting past the blood-brain barrier. MAbs. Mar.-Apr. 2011;3(2):153-60. Epub Mar. 1, 2011.

Lefranc et al., IMGT unique numbering for immunoglobulin and T cell receptor variable domains and Ig superfamily V-like domains. Dev Comp Immunol. Jan. 2003;27(1):55-77.

Li et al., Pentabody-mediated antigen delivery induces antigen-specific mucosal immune response. Mol Immunol. May 2009;46(8-9):1718-26. doi:10.1016/j.molimm.Feb. 7, 2009. Epub Mar. 9, 2009.

LIN, CSF as a surrogate for assessing CNS exposure: an industrial perspective. Curr Drug Metab. Jan. 2008;9(1):46-59.

Merritt et al., AB5 toxins. Gun Opin Struct Biol. Apr. 1995;5(2):165-71.

Muruganandam et al., Selection of phage-displayed llama single-domain antibodies that transmigrate across human blood-brain barrier endothelium. FASEB J. Feb. 2002;16(2):240-2. Epub Dec. 28, 2001.

Musher et al., Detection of Clostridium difficile toxin: comparison of enzyme immunoassay results with results obtained by cytotoxicity assay. J Clin Microbiol. Aug. 2007;45(8):2737-9. Epub Jun. 13, 2007.

Neuwelt et al., Engaging neuroscience to advance translational research in brain barrier biology. Nat Rev Neurosci. Mar. 2011;12(3):169-82. doi:10.1038/nrn2995.

Nhan et al., Drug delivery to the brain by focused ultrasound induced blood-brain barrier disruption:quantitative evaluation of enhanced permeability of cerebral vasculature using two-photon microscopy. J Control Release. Nov. 28, 2013;172(1):274-80. doi:10.1016/j.jconrel.Aug. 29, 2013. Epub Sep. 2, 2013.

Nicaise et al., Affinity transfer by CDR grafting on a nonimmunoglobulin scaffold. Protein Sci. Jul. 2004;13(7):1882-91. Epub May 28, 2004.

Nielsen et al., Targeting of bivalent anti-ErbB2 diabody antibody fragments to tumor cells is independent of the intrinsic antibody affinity. Cancer Res. Nov. 15, 2000;60(22):6434-40.

Nirogi et al., A simple and rapid method to collect the cerebrospinal fluid of rats and its application for the assessment of drug penetration into the central nervous system. J Neurosci Methods. Mar. 30, 2009;178(1):116-9. doi:10.1016/j.jneumeth.Dec. 1, 2008. Epub Dec. 6, 2008.

Nuttall et al., Isolation and characterization of an IgNAR variable domain specific for the human mitochondrial translocase receptor Tom70. Eur J Biochem. Sep. 2003;270(17):3543-54.

Pardridge et al., Reengineering biopharmaceuticals for targeted delivery across the blood-brain barrier. Methods Enzymol. 2012;503:269-92. doi:10.1016/B978-0-12-396962-0.00011-2.

Pardridge et al., Selective transport of an anti-transferrin receptor antibody through the blood-brain barrier in vivo. J Pharmacol Exp Ther. Oct. 1991;259(1):66-70.

Pardridge, Transport of small molecules through the blood-brain barrier: biology and methodology. Adv. Drug Delivery Reviews, 15, 5-36 (1995).

Pardridge, Blood-brain barrier delivery. Drug Discov Today. Jan. 2007;12(1-2):54-61. Epub Nov. 13, 2006.

Pardridge, Drug and gene delivery to the brain: the vascular route. Neuron. Nov. 14, 2002;36(4):555-8.

Pardridge, Drug targeting to the brain. Pharm Res. Sep. 2007;24(9):1733-44. Epub Jun. 7, 2007.

Pardridge, Drug transport across the blood-brain barrier. J Cereb Blood Flow Metab. Nov. 2012;32(11):1959-72. doi: 10.1038/jcbfm.2012.126. Epub Aug. 29, 2012.

Pardridge, Preparation of Trojan horse liposomes (THLs) for gene transfer across the blood-brain barrier. Cold Spring Harb Protoc. Apr. 2010;2010(4):pdb.prot5407. doi: 10.1101/pdb.prot5407.

Planche et al., Diagnosis of Clostridium difficile infection by toxin detection kits: a systematic review. Lancet Infect Dis. Dec. 2008;8(12):777-84. doi:10.1016/S1473-3099(08)70233-0. Epub Nov. 1, 2008.

Preston et al., Graded reversible opening of the rat blood-brain barrier by intracarotid infusion of sodium caprate. J Neurosci Methods. Mar. 15, 2008;168(2):443-9. Epub Nov. 19, 2007.

Ridgway et al., 'Knobs-into-holes' engineering of antibody CH3 domains for heavy chain heterodimerization. Protein Eng. Jul. 1996;9(7):617-21.

Robertson et al., Anticonvulsant neuropeptides as drug leads for neurological diseases. Nat Prod Rep. Apr. 2011;28(4):741-62. doi:10.1039/c0np00048e. Epub Feb. 21, 2011.

Russmann et al., Evaluation of three rapid assays for detection of Clostridium difficile toxin A and toxin B in stool specimens. Eur J Clin Microbiol Infect Dis. Feb. 2007;26(2):115-9.

Samani et al., Loss of tumorigenicity and metastatic potential in carcinoma cells expressing the extracellular domain of the type 1 insulin-like growth factor receptor. Cancer Res. May 15, 2004;64(10):3380-5.

Samuels et al., Modulation of vinblastine resistance with cyclosporine: a phase I study. Clin Pharmacol Ther. Oct. 1993;54(4):421-9.

Shen et al., Principles and applicability of CSF sampling for the assessment of CNS drug delivery and pharmacodynamics. Adv Drug Deliv Rev. Oct. 14, 2004;56(12):1825-57.

Sloan et al., Comparison of real-time PCR for detection of the tcdC gene with four toxin immunoassays and culture in diagnosis of Clostridium difficile infection. J Clin Microbiol. Jun. 2008;46(6):1996-2001. doi: 10.1128/JCM.00032-08. Epub Apr. 23, 2008.

Sumbria et al., Pharmacokinetics and brain uptake of an IgG-TNF decoy receptor fusion protein following intravenous, intraperitoneal, and subcutaneous administration in mice. Mol Pharm. Apr. 1, 2013;10(4):1425-31. doi: 10.1021/mp400004a. Epub Feb. 28, 2013.

Tanha et al., Phage display technology for identifying specific antigens on brain endothelial cells. Methods Mol Med. 2003;89:435-49.

(56) References Cited

OTHER PUBLICATIONS

To et al., Isolation of monomeric human V(H)s by a phage selection. J Biol Chem. Dec. 16, 2005;280(50):41395-403. Epub Oct. 12, 2005.

Turgeon et al., Six rapid tests for direct detection of Clostridium difficile and its toxins in fecal samples compared with the fibroblast cytotoxicity assay. J Clin Microbiol. Feb. 2003;41(2):667-70.

Watanabe et al., Comparative study on reversal efficacy of SDZ PSC 833, cyclosporin A and verapamil on multidrug resistance in vitro and in vivo. Acta Oncol. 1995;34(2):235-41.

Xiao et al., (2013) Receptor-mediated endocytosis and brain delivery of therapeutic biologics. Int J Cell Biol. doi: 10.1155/2013/703545. Epub Jun. 11, 2013.

Yaksh et al., Chronic catheterization of the spinal subarachnoid space. Physiol Behav. 1976;17(6):1031-6.

Yu et al., Boosting brain uptake of a therapeutic antibody by reducing its affinity for a transcytosis target. Sci Transl Med. May 25, 2011;3(84):84ra44. doi:10.1126/scitranslmed.3002230.

Zhang et al., A pentavalent single-domain antibody approach to tumor antigen discovery and the development of novel proteomics reagents. J Mol Biol. Jul. 30, 2004;341(1):161-9.

Zhang et al., Fluorescent tumour imaging of type I IGF receptor in vivo: comparison of antibody-conjugated quantum dots and small-molecule fluorophore. Br J Cancer. Jul. 7, 2009;101(1):71-9. doi:10.1038/sj.bjc.6605103. Epub Jun. 2, 2009.

Zhang et al., Pentamerization of single-domain antibodies from phage libraries: a novel strategy for the rapid generation of high-avidity antibody reagents. J Mol Biol. Jan. 2, 2004;335(1):49-56.

Zhu et al., COMBODY: one-domain antibody multimer with improved avidity. Immunol Cell Biol. Aug. 2010;88(6):667-75. doi: 10.1038/icb.2010.21. Epub Mar. 9, 2010.

Menting et al., Structural congruency of ligand binding to the insulin and insulin/type 1 insulin-like growth factor hybrid receptors. Structure. Jul. 7, 2015;23(7): 1271-82. doi: 10.1016/j.str.Apr. 16, 2015. Epub May 28, 2015.

Niewoehner et al., Increased brain penetration and potency of a therapeutic antibody using a monovalent molecular shuttle. Neuron. Jan. 8, 2014;81(1):49-60. doi:10.1016/j.neuron.2013.10.061.

Sade et al., A human blood-brain barrier transcytosis assay reveals antibody transcytosis influenced by pH-dependent receptor binding. PLoS One. Apr. 30, 2014;9(4):e96340. doi: 10.1371/journal.pone.0096340. eCollection 2014.

Stanimirovic et al., Engineering and pharmacology of blood-brain barrier-permeable bispecific antibodies. Adv Pharmacol. 2014;71:301-35. doi: 10.1016/bs.apha.Jun. 5, 2014. Epub Aug. 23, 2014.

* cited by examiner

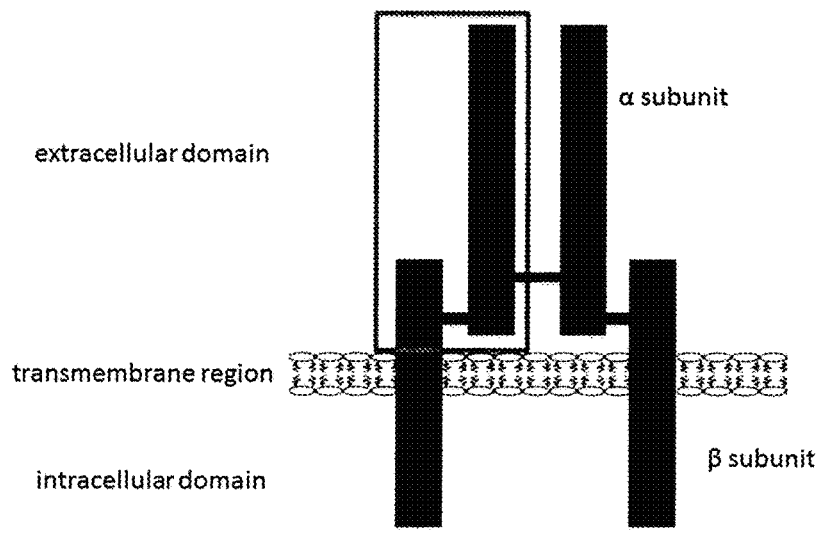

FIG. 1

```
MKSGSGGGSP TSLWGLLFLS AALSLWPTSG EICGPGIDIR NDYQQLKRLE NCTVIEGYLH      60
ILLISKAEDY RSYRFPKLTV ITEYLLLFRV AGLESLGDLF PNLTVIRGWK LFYNYALVIF     120
EMTNLKDIGL YNLRNITRGA IRIEKNADLC YLSTVDWSLI LDAVSNNYIV GNKPPKECGD     180
LCPGTMEEKP MCEKTTINNE YNYRCWTTNR CQKMCPSTCG KRACTENNEC CHPECLGSCS     240
APDNDTACVA CRHYYYAGVC VPACPPNTYR FEGWRCVDRD FCANILSAES SDSEGFVIHD     300
GECMQECPSG FIRNGSQSMY CIPCEGPCPK VCEEERKTKT IDSVTSAQML QGCTIFKGNL     360
LINIRRGHNI ASELENFMGL IEVVTGYVKI RHSHALVSLS FLKNLRLILG EEQLEGNYSF     420
YVLDNQNLQQ LWDWDHRNLT IKAGKMYFAF NPKLCVSEIY RMEEVTGTKG RQSKGDINTR     480
NNGERASCES DVLHFTSTTT SKNRIIITWH RYRPPDYRDL ISFTVYYKEA PFKNVTEYDG     540
QDACGSNSWN MVDVDLPPNK DVEPGILLHG LKPWTQYAVY VKAVTLTMVE NDHIRGAKSE     600
ILYIRTNASV PSIPLDVLSA SNSSSQLIVK WNPPSLPNGN LSYYIVRWQR QPQDGYLYRH     660
NYCSKDKIPI RKYADGTIDI EEVTENPKTE VCGGEKGPCC ACPKTEAEKQ AEKEEAEYRK     720
VFENFLHNSI FVPRPErkrr DVMQVANTTM SSRSRNTTAA DTYNITDPEE LETEYPFFES     780
RVDNKERTVI SNLRPFTLYR IDIHSCNHEA EKLGCSASNF VFARTMPAEG ADDIPGPVTW     840
EPRPENSIFL KWPEPENPNG LILMYEIKYG SQVEDQRECV SRQEYRKYGG AKLNRLNPGN     900
YTARIQATSL SGNGSWTDPV FFYVQAKTGY ENFIHLIIAL PVAVLLIVGG LVIMLYVFHR     960
KRNNSRLGNG VLYASVNPEY FSAADVYVPD EWEVAREKIT MSRELGQGSF GMVYEGVAKG    1020
VVKDEPETRV AIKTVNEAAS MRERIEFLNE ASVMKEFNCH HVVRLLGVVS QGQPTLVIME    1080
LMTRGDLKSY LRSLRPEMEN NPVLAPPSLS KMIQMAGEIA DGMAYLNANK FVHRDLAARN    1140
CMVAEDFTVK IGDFGMTRDI YETDYYRKGG KGLLPVRWMS PESLKDGVFT TYSDVWSFGV    1200
VLWEIATLAE QPYQGLSNEQ VLRFVMEGGL LDKPDNCPDM LFELMRMCWQ YNPKMRPSFL    1260
EIISSIKEEM EPGFREVSFY YSEENKLPEP EELDLEPENM ESVPLDPSAS SSSLPLPDRH    1320
SGHKAENGPG PGVLVLRASF DERQPYAHMN GGRKNERALP LPQSSTC                 1367
```

FIG. 2

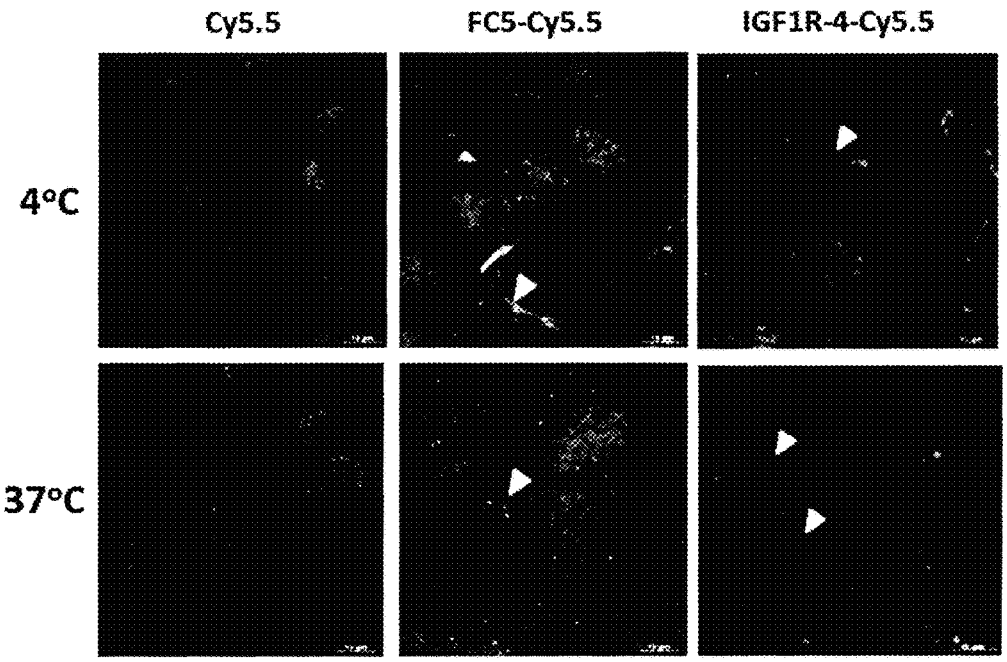

FIG. 4

QVKLEESGGGLVQAGGSLRLSCEVSGGTVSPTAMGWFRQAPGKEREFVGHITWSRGTTRVASS
VKDRFTISRDSAKNTVYLQMNSLKSEDTAVYYCAASTFLRILPEESAYTYWGQGTQVTVSSMTVD
KKLEPSGPISTINPCPPCKECHKCPAPNLEGGPSVFIFPPNIKDVLMISLTPKVTCVVVDVSEDDPDV
QISWFVNNVEVHTAQTQTHREDYNSTIRVVSTLPIQHQDWMSGKEFKCKVNNKDLPSPIERTISK
IKGLVRAPQVYILPPPAEQLSRKDVSLTCLVVGFNPGDISVEWTSNGHTEENYKDTAPVLDSDGSY
FIYSKLNMKTSKWEKTDSFSCNVRHEGLKNYYLKKTISRSPGK

FIG. 5A

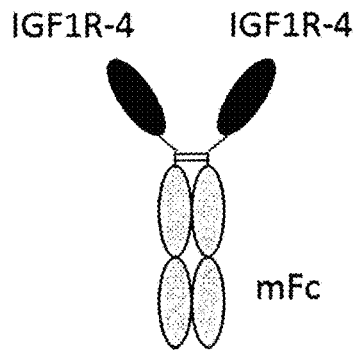

FIG. 5B

SEQUENCE LISTING

```
<160> NUMBER OF SEQ ID NOS: 38

<210> SEQ ID NO 1
<211> LENGTH: 8
<212> TYPE: PRT
<213> ORGANISM: Artificial
<220> FEATURE:
<223> OTHER INFORMATION: IGF1R-4 CDR1

<400> SEQUENCE: 1

Gly Gly Thr Val Ser Pro Thr Ala
1               5

<210> SEQ ID NO 2
<211> LENGTH: 8
<212> TYPE: PRT
<213> ORGANISM: Artificial
<220> FEATURE:
<223> OTHER INFORMATION: IGF1R-4 CDR2

<400> SEQUENCE: 2

Ile Thr Trp Ser Arg Gly Thr Thr
1               5

<210> SEQ ID NO 3
<211> LENGTH: 17
<212> TYPE: PRT
<213> ORGANISM: Artificial
<220> FEATURE:
<223> OTHER INFORMATION: IGF1R-4 CDR3

<400> SEQUENCE: 3

Ala Ala Ser Thr Phe Leu Arg Ile Leu Pro Glu Glu Ser Ala Tyr Thr
1               5                   10                  15

Tyr

<210> SEQ ID NO 4
<211> LENGTH: 124
<212> TYPE: PRT
<213> ORGANISM: Artificial
<220> FEATURE:
<223> OTHER INFORMATION: IGF1R-4 Consensus
<220> FEATURE:
<221> NAME/KEY: MISC_FEATURE
<222> LOCATION: (1)..(1)
<223> OTHER INFORMATION: Xaa is Glu or Gln
<220> FEATURE:
<221> NAME/KEY: MISC_FEATURE
<222> LOCATION: (3)..(3)
<223> OTHER INFORMATION: Xaa is Lys or Gln
<220> FEATURE:
<221> NAME/KEY: MISC_FEATURE
<222> LOCATION: (5)..(5)
<223> OTHER INFORMATION: Xaa is Val or Glu
<220> FEATURE:
<221> NAME/KEY: MISC_FEATURE
<222> LOCATION: (14)..(14)
<223> OTHER INFORMATION: Xaa is Ala or Pro
<220> FEATURE:
<221> NAME/KEY: MISC_FEATURE
<222> LOCATION: (23)..(23)
<223> OTHER INFORMATION: Xaa is Ala or Glu
```

```
<220> FEATURE:
<221> NAME/KEY: MISC_FEATURE
<222> LOCATION: (24)..(24)
<223> OTHER INFORMATION: Xaa is Val or Ala
<220> FEATURE:
<221> NAME/KEY: MISC_FEATURE
<222> LOCATION: (37)..(37)
<223> OTHER INFORMATION: Xaa is Val or Phe
<220> FEATURE:
<221> NAME/KEY: MISC_FEATURE
<222> LOCATION: (44)..(44)
<223> OTHER INFORMATION: Xaa is Gly or Glu
<220> FEATURE:
<221> NAME/KEY: MISC_FEATURE
<222> LOCATION: (45)..(45)
<223> OTHER INFORMATION: Xaa is Leu or Arg
<220> FEATURE:
<221> NAME/KEY: MISC_FEATURE
<222> LOCATION: (47)..(47)
<223> OTHER INFORMATION: Xaa is Phe or Trp
<220> FEATURE:
<221> NAME/KEY: MISC_FEATURE
<222> LOCATION: (49)..(49)
<223> OTHER INFORMATION: Xaa is Gly or Ser
<220> FEATURE:
<221> NAME/KEY: MISC_FEATURE
<222> LOCATION: (60)..(60)
<223> OTHER INFORMATION: Xaa is Val or Tyr
<220> FEATURE:
<221> NAME/KEY: MISC_FEATURE
<222> LOCATION: (66)..(66)
<223> OTHER INFORMATION: Xaa is Asp or Gly
<220> FEATURE:
<221> NAME/KEY: MISC_FEATURE
<222> LOCATION: (74)..(74)
<223> OTHER INFORMATION: Xaa is Asn or Ser
<220> FEATURE:
<221> NAME/KEY: MISC_FEATURE
<222> LOCATION: (75)..(75)
<223> OTHER INFORMATION: Xaa is Ala or Ser
<220> FEATURE:
<221> NAME/KEY: MISC_FEATURE
<222> LOCATION: (79)..(79)
<223> OTHER INFORMATION: Xaa is Leu or Val
<220> FEATURE:
<221> NAME/KEY: MISC_FEATURE
<222> LOCATION: (87)..(87)
<223> OTHER INFORMATION: Xaa is Lys or Arg
<220> FEATURE:
<221> NAME/KEY: MISC_FEATURE
<222> LOCATION: (88)..(88)
<223> OTHER INFORMATION: Xaa is Ala or Ser
<220> FEATURE:
<221> NAME/KEY: MISC_FEATURE
<222> LOCATION: (119)..(119)
<223> OTHER INFORMATION: Xaa is Leu or Gln

<400> SEQUENCE: 4

Xaa Val Xaa Leu Xaa Glu Ser Gly Gly Gly Leu Val Gln Xaa Gly Gly
 1               5                  10                  15

Ser Leu Arg Leu Ser Cys Xaa Xaa Ser Gly Gly Thr Val Ser Pro Thr
            20                  25                  30

Ala Met Gly Trp Xaa Arg Gln Ala Pro Gly Lys Xaa Xaa Glu Xaa Val
        35                  40                  45

Xaa His Ile Thr Trp Ser Arg Gly Thr Thr Arg Xaa Ala Ser Ser Val
    50                  55                  60

Lys Xaa Arg Phe Thr Ile Ser Arg Asp Xaa Xaa Lys Asn Thr Xaa Tyr
65                  70                  75                  80

Leu Gln Met Asn Ser Leu Xaa Xaa Glu Asp Thr Ala Val Tyr Tyr Cys
                85                  90                  95
```

```
Ala Ala Ser Thr Phe Leu Arg Ile Leu Pro Glu Glu Ser Ala Tyr Thr
                100                 105                 110

Tyr Trp Gly Gln Gly Thr Xaa Val Thr Val Ser Ser
        115                 120
```

<210> SEQ ID NO 5
<211> LENGTH: 124
<212> TYPE: PRT
<213> ORGANISM: Artificial
<220> FEATURE:
<223> OTHER INFORMATION: IGF1R-4 VHH

<400> SEQUENCE: 5

```
Gln Val Lys Leu Glu Glu Ser Gly Gly Gly Leu Val Gln Ala Gly Gly
1               5                   10                  15

Ser Leu Arg Leu Ser Cys Glu Val Ser Gly Gly Thr Val Ser Pro Thr
            20                  25                  30

Ala Met Gly Trp Phe Arg Gln Ala Pro Gly Lys Glu Arg Glu Phe Val
        35                  40                  45

Gly His Ile Thr Trp Ser Arg Gly Thr Thr Arg Val Ala Ser Ser Val
    50                  55                  60

Lys Asp Arg Phe Thr Ile Ser Arg Asp Ser Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ala Ser Thr Phe Leu Arg Ile Leu Pro Glu Glu Ser Ala Tyr Thr
                100                 105                 110

Tyr Trp Gly Gln Gly Thr Gln Val Thr Val Ser Ser
        115                 120
```

<210> SEQ ID NO 6
<211> LENGTH: 124
<212> TYPE: PRT
<213> ORGANISM: Artificial
<220> FEATURE:
<223> OTHER INFORMATION: IGF1R-4_H2

<400> SEQUENCE: 6

```
Gln Val Gln Leu Val Glu Ser Gly Gly Gly Leu Val Gln Pro Gly Gly
1               5                   10                  15

Ser Leu Arg Leu Ser Cys Ala Val Ser Gly Gly Thr Val Ser Pro Thr
            20                  25                  30

Ala Met Gly Trp Val Arg Gln Ala Pro Gly Lys Gly Leu Glu Trp Val
        35                  40                  45

Gly His Ile Thr Trp Ser Arg Gly Thr Thr Arg Tyr Ala Ser Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Ser Thr Phe Leu Arg Ile Leu Pro Glu Glu Ser Ala Tyr Thr
                100                 105                 110

Tyr Trp Gly Gln Gly Thr Leu Val Thr Val Ser Ser
        115                 120
```

<210> SEQ ID NO 7
<211> LENGTH: 124
<212> TYPE: PRT
<213> ORGANISM: Artificial

<220> FEATURE:
<223> OTHER INFORMATION: IGF1R-4_H3

<400> SEQUENCE: 7

Gln Val Gln Leu Val Glu Ser Gly Gly Gly Leu Val Gln Pro Gly Gly
1               5                   10                  15

Ser Leu Arg Leu Ser Cys Ala Val Ser Gly Gly Thr Val Ser Pro Thr
            20                  25                  30

Ala Met Gly Trp Phe Arg Gln Ala Pro Gly Lys Gly Leu Glu Phe Val
        35                  40                  45

Gly His Ile Thr Trp Ser Arg Gly Thr Thr Arg Tyr Ala Ser Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Ser Thr Phe Leu Arg Ile Leu Pro Glu Glu Ser Ala Tyr Thr
            100                 105                 110

Tyr Trp Gly Gln Gly Thr Leu Val Thr Val Ser Ser
        115                 120

<210> SEQ ID NO 8
<211> LENGTH: 124
<212> TYPE: PRT
<213> ORGANISM: Artificial
<220> FEATURE:
<223> OTHER INFORMATION: IGF1R-4_H4

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Ala Val Ser Gly Gly Thr Val Ser Pro Thr
            20                  25                  30

Ala Met Gly Trp Phe Arg Gln Ala Pro Gly Lys Gly Leu Glu Phe Val
        35                  40                  45

Gly His Ile Thr Trp Ser Arg Gly Thr Thr Arg Tyr Ala Ser Ser Val
    50                  55                  60

Lys Gly Arg Phe Thr Ile Ser Arg Asp Ser Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Ser Thr Phe Leu Arg Ile Leu Pro Glu Glu Ser Ala Tyr Thr
            100                 105                 110

Tyr Trp Gly Gln Gly Thr Leu Val Thr Val Ser Ser
        115                 120

<210> SEQ ID NO 9
<211> LENGTH: 124
<212> TYPE: PRT
<213> ORGANISM: Artificial
<220> FEATURE:
<223> OTHER INFORMATION: IGF1R-4_H5

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Ala Val Ser Gly Gly Thr Val Ser Pro Thr
            20                  25                  30

-continued

```
Ala Met Gly Trp Phe Arg Gln Ala Pro Gly Lys Glu Arg Glu Phe Val
        35                  40                  45

Gly His Ile Thr Trp Ser Arg Gly Thr Thr Arg Tyr Ala Ser Ser Val
 50                  55                  60

Lys Gly Arg Phe Thr Ile Ser Arg Asp Ser Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Ala Ser Thr Phe Leu Arg Ile Leu Pro Glu Glu Ser Ala Tyr Thr
            100                 105                 110

Tyr Trp Gly Gln Gly Thr Leu Val Thr Val Ser Ser
            115                 120

<210> SEQ ID NO 10
<211> LENGTH: 370
<212> TYPE: PRT
<213> ORGANISM: Artificial
<220> FEATURE:
<223> OTHER INFORMATION: IGF1R-4 consensus-Fc fusion
<220> FEATURE:
<221> NAME/KEY: MISC_FEATURE
<222> LOCATION: (1)..(1)
<223> OTHER INFORMATION: Xaa is Glu or Gln
<220> FEATURE:
<221> NAME/KEY: MISC_FEATURE
<222> LOCATION: (3)..(3)
<223> OTHER INFORMATION: Xaa is Lys or Gln
<220> FEATURE:
<221> NAME/KEY: MISC_FEATURE
<222> LOCATION: (5)..(5)
<223> OTHER INFORMATION: Xaa is Val or Glu
<220> FEATURE:
<221> NAME/KEY: MISC_FEATURE
<222> LOCATION: (14)..(14)
<223> OTHER INFORMATION: Xaa is Ala or Pro
<220> FEATURE:
<221> NAME/KEY: MISC_FEATURE
<222> LOCATION: (23)..(23)
<223> OTHER INFORMATION: Xaa is Ala or Glu
<220> FEATURE:
<221> NAME/KEY: MISC_FEATURE
<222> LOCATION: (24)..(24)
<223> OTHER INFORMATION: Xaa is Val or Ala
<220> FEATURE:
<221> NAME/KEY: MISC_FEATURE
<222> LOCATION: (37)..(37)
<223> OTHER INFORMATION: Xaa is Val or Phe
<220> FEATURE:
<221> NAME/KEY: MISC_FEATURE
<222> LOCATION: (44)..(44)
<223> OTHER INFORMATION: Xaa is Gly or Glu
<220> FEATURE:
<221> NAME/KEY: MISC_FEATURE
<222> LOCATION: (45)..(45)
<223> OTHER INFORMATION: Xaa is Leu or Arg
<220> FEATURE:
<221> NAME/KEY: MISC_FEATURE
<222> LOCATION: (47)..(47)
<223> OTHER INFORMATION: Xaa is Phe or Trp
<220> FEATURE:
<221> NAME/KEY: MISC_FEATURE
<222> LOCATION: (49)..(49)
<223> OTHER INFORMATION: Xaa is Gly or Ser
<220> FEATURE:
<221> NAME/KEY: MISC_FEATURE
<222> LOCATION: (60)..(60)
<223> OTHER INFORMATION: Xaa is Val or Tyr
<220> FEATURE:
<221> NAME/KEY: MISC_FEATURE
<222> LOCATION: (66)..(66)
<223> OTHER INFORMATION: Xaa is Asp or Gly
```

-continued

```
<220> FEATURE:
<221> NAME/KEY: MISC_FEATURE
<222> LOCATION: (74)..(74)
<223> OTHER INFORMATION: Xaa is Asn or Ser
<220> FEATURE:
<221> NAME/KEY: MISC_FEATURE
<222> LOCATION: (75)..(75)
<223> OTHER INFORMATION: Xaa is Ala or Ser
<220> FEATURE:
<221> NAME/KEY: MISC_FEATURE
<222> LOCATION: (79)..(79)
<223> OTHER INFORMATION: Xaa is Leu or Val
<220> FEATURE:
<221> NAME/KEY: MISC_FEATURE
<222> LOCATION: (87)..(87)
<223> OTHER INFORMATION: Xaa is Lys or Arg
<220> FEATURE:
<221> NAME/KEY: MISC_FEATURE
<222> LOCATION: (88)..(88)
<223> OTHER INFORMATION: Xaa is Ala or Ser
<220> FEATURE:
<221> NAME/KEY: MISC_FEATURE
<222> LOCATION: (119)..(119)
<223> OTHER INFORMATION: Xaa is Leu or Gln

<400> SEQUENCE: 10

Xaa Val Xaa Leu Xaa Glu Ser Gly Gly Gly Leu Val Gln Xaa Gly Gly
1               5                   10                  15

Ser Leu Arg Leu Ser Cys Xaa Xaa Ser Gly Gly Thr Val Ser Pro Thr
            20                  25                  30

Ala Met Gly Trp Xaa Arg Gln Ala Pro Gly Lys Xaa Xaa Glu Xaa Val
        35                  40                  45

Xaa His Ile Thr Trp Ser Arg Gly Thr Thr Arg Xaa Ala Ser Ser Val
    50                  55                  60

Lys Xaa Arg Phe Thr Ile Ser Arg Asp Xaa Xaa Lys Asn Thr Xaa Tyr
65                  70                  75                  80

Leu Gln Met Asn Ser Leu Xaa Xaa Glu Asp Thr Ala Val Tyr Tyr Cys
                85                  90                  95

Ala Ala Ser Thr Phe Leu Arg Ile Leu Pro Glu Glu Ser Ala Tyr Thr
            100                 105                 110

Tyr Trp Gly Gln Gly Thr Xaa Val Thr Val Ser Ser Met Thr Val Asp
        115                 120                 125

Lys Lys Leu Glu Pro Ser Gly Pro Ile Ser Thr Ile Asn Pro Cys Pro
130                 135                 140

Pro Cys Lys Glu Cys His Lys Cys Pro Ala Pro Asn Leu Glu Gly Gly
145                 150                 155                 160

Pro Ser Val Phe Ile Phe Pro Pro Asn Ile Lys Asp Val Leu Met Ile
                165                 170                 175

Ser Leu Thr Pro Lys Val Thr Cys Val Val Asp Val Ser Glu Asp
            180                 185                 190

Asp Pro Asp Val Gln Ile Ser Trp Phe Val Asn Asn Val Glu Val His
        195                 200                 205

Thr Ala Gln Thr Gln Thr His Arg Glu Asp Tyr Asn Ser Thr Ile Arg
    210                 215                 220

Val Val Ser Thr Leu Pro Ile Gln His Gln Asp Trp Met Ser Gly Lys
225                 230                 235                 240

Glu Phe Lys Cys Lys Val Asn Asn Lys Asp Leu Pro Ser Pro Ile Glu
                245                 250                 255

Arg Thr Ile Ser Lys Ile Lys Gly Leu Val Arg Ala Pro Gln Val Tyr
            260                 265                 270
```

```
Ile Leu Pro Pro Pro Ala Glu Gln Leu Ser Arg Lys Asp Val Ser Leu
            275                 280                 285

Thr Cys Leu Val Val Gly Phe Asn Pro Gly Asp Ile Ser Val Glu Trp
290                 295                 300

Thr Ser Asn Gly His Thr Glu Glu Asn Tyr Lys Asp Thr Ala Pro Val
305                 310                 315                 320

Leu Asp Ser Asp Gly Ser Tyr Phe Ile Tyr Ser Lys Leu Asn Met Lys
                325                 330                 335

Thr Ser Lys Trp Glu Lys Thr Asp Ser Phe Ser Cys Asn Val Arg His
            340                 345                 350

Glu Gly Leu Lys Asn Tyr Tyr Leu Lys Lys Thr Ile Ser Arg Ser Pro
                355                 360                 365

Gly Lys
    370

<210> SEQ ID NO 11
<211> LENGTH: 370
<212> TYPE: PRT
<213> ORGANISM: Artificial
<220> FEATURE:
<223> OTHER INFORMATION: IGF1R-4-Fc fusion

<400> SEQUENCE: 11

Gln Val Lys Leu Glu Glu Ser Gly Gly Gly Leu Val Gln Ala Gly Gly
1               5                   10                  15

Ser Leu Arg Leu Ser Cys Glu Val Ser Gly Gly Thr Val Ser Pro Thr
            20                  25                  30

Ala Met Gly Trp Phe Arg Gln Ala Pro Gly Lys Glu Arg Glu Phe Val
        35                  40                  45

Gly His Ile Thr Trp Ser Arg Gly Thr Thr Arg Val Ala Ser Ser Val
    50                  55                  60

Lys Asp Arg Phe Thr Ile Ser Arg Asp Ser Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ala Ser Thr Phe Leu Arg Ile Leu Pro Glu Glu Ser Ala Tyr Thr
            100                 105                 110

Tyr Trp Gly Gln Gly Thr Gln Val Thr Val Ser Ser Met Thr Val Asp
        115                 120                 125

Lys Lys Leu Glu Pro Ser Gly Pro Ile Ser Thr Ile Asn Pro Cys Pro
    130                 135                 140

Pro Cys Lys Glu Cys His Lys Cys Pro Ala Pro Asn Leu Glu Gly Gly
145                 150                 155                 160

Pro Ser Val Phe Ile Phe Pro Pro Asn Ile Lys Asp Val Leu Met Ile
                165                 170                 175

Ser Leu Thr Pro Lys Val Thr Cys Val Val Asp Val Ser Glu Asp
            180                 185                 190

Asp Pro Asp Val Gln Ile Ser Trp Phe Val Asn Asn Val Glu Val His
        195                 200                 205

Thr Ala Gln Thr Gln Thr His Arg Glu Asp Tyr Asn Ser Thr Ile Arg
    210                 215                 220

Val Val Ser Thr Leu Pro Ile Gln His Gln Asp Trp Met Ser Gly Lys
225                 230                 235                 240

Glu Phe Lys Cys Lys Val Asn Asn Lys Asp Leu Pro Ser Pro Ile Glu
                245                 250                 255
```

```
Arg Thr Ile Ser Lys Ile Lys Gly Leu Val Arg Ala Pro Gln Val Tyr
            260                 265                 270

Ile Leu Pro Pro Pro Ala Glu Gln Leu Ser Arg Lys Asp Val Ser Leu
        275                 280                 285

Thr Cys Leu Val Val Gly Phe Asn Pro Gly Asp Ile Ser Val Glu Trp
    290                 295                 300

Thr Ser Asn Gly His Thr Glu Glu Asn Tyr Lys Asp Thr Ala Pro Val
305                 310                 315                 320

Leu Asp Ser Asp Gly Ser Tyr Phe Ile Tyr Ser Lys Leu Asn Met Lys
                325                 330                 335

Thr Ser Lys Trp Glu Lys Thr Asp Ser Phe Ser Cys Asn Val Arg His
            340                 345                 350

Glu Gly Leu Lys Asn Tyr Tyr Leu Lys Lys Thr Ile Ser Arg Ser Pro
        355                 360                 365

Gly Lys
    370

<210> SEQ ID NO 12
<211> LENGTH: 1367
<212> TYPE: PRT
<213> ORGANISM: Artificial
<220> FEATURE:
<223> OTHER INFORMATION: IGF1R

<400> SEQUENCE: 12

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240
```

```
Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
    370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
    450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
    530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
        595                 600                 605

Ser Val Pro Ser Ile Pro Leu Asp Val Leu Ser Ala Ser Asn Ser Ser
    610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655
```

```
Leu Tyr Arg His Asn Tyr Cys Ser Lys Asp Lys Ile Pro Ile Arg Lys
                660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
        690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn
    770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
    930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
        995                 1000                1005

Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
    1040                1045                1050

Met Lys Glu Phe Asn Cys His His Val Val Arg Leu Leu Gly Val
    1055                1060                1065
```

-continued

Val Ser Gln Gly Gln Pro Thr Leu Val Ile Met Glu Leu Met Thr
    1070                1075                1080

Arg Gly Asp Leu Lys Ser Tyr Leu Arg Ser Leu Arg Pro Glu Met
    1085                1090                1095

Glu Asn Asn Pro Val Leu Ala Pro Pro Ser Leu Ser Lys Met Ile
    1100                1105                1110

Gln Met Ala Gly Glu Ile Ala Asp Gly Met Ala Tyr Leu Asn Ala
    1115                1120                1125

Asn Lys Phe Val His Arg Asp Leu Ala Ala Arg Asn Cys Met Val
    1130                1135                1140

Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Gly Lys Gly Leu
    1160                1165                1170

Leu Pro Val Arg Trp Met Ser Pro Glu Ser Leu Lys Asp Gly Val
    1175                1180                1185

Phe Thr Thr Tyr Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Ile Lys Glu Glu Met Glu Pro Gly Phe Arg Glu Val Ser
    1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His Ser Gly His
    1310                1315                1320

Lys Ala Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
    1355                1360                1365

<210> SEQ ID NO 13
<211> LENGTH: 4
<212> TYPE: PRT
<213> ORGANISM: Artificial
<220> FEATURE:
<223> OTHER INFORMATION: Furin cleavage site

<400> SEQUENCE: 13

Arg Lys Arg Arg
1

<210> SEQ ID NO 14
<211> LENGTH: 33
<212> TYPE: DNA
<213> ORGANISM: Artificial

```
<220> FEATURE:
<223> OTHER INFORMATION: Forward primer

<400> SEQUENCE: 14
cgggatccgc caccatgaag tctggctccg gag                                    33

<210> SEQ ID NO 15
<211> LENGTH: 34
<212> TYPE: DNA
<213> ORGANISM: Artificial
<220> FEATURE:
<223> OTHER INFORMATION: Reverse primer

<400> SEQUENCE: 15
gctctagatc agaagttttc atatcctgtt ttgg                                   34

<210> SEQ ID NO 16
<211> LENGTH: 45
<212> TYPE: DNA
<213> ORGANISM: Artificial
<220> FEATURE:
<223> OTHER INFORMATION: MJ1 primer

<400> SEQUENCE: 16
gcccagccgg ccatggccsm kgtgcagctg gtggaktctg gggga                       45

<210> SEQ ID NO 17
<211> LENGTH: 45
<212> TYPE: DNA
<213> ORGANISM: Artificial
<220> FEATURE:
<223> OTHER INFORMATION: MJ2 primer

<400> SEQUENCE: 17
gcccagccgg ccatggccca ggtaaagctg gaggagtctg gggga                       45

<210> SEQ ID NO 18
<211> LENGTH: 45
<212> TYPE: DNA
<213> ORGANISM: Artificial
<220> FEATURE:
<223> OTHER INFORMATION: MJ3 primer

<400> SEQUENCE: 18
gcccagccgg ccatggccca ggctcaggta cagctggtgg agtct                       45

<210> SEQ ID NO 19
<211> LENGTH: 21
<212> TYPE: DNA
<213> ORGANISM: Artificial
<220> FEATURE:
<223> OTHER INFORMATION: CH2 primer

<400> SEQUENCE: 19
cgccatcaag gtaccagttg a                                                 21

<210> SEQ ID NO 20
<211> LENGTH: 29
<212> TYPE: DNA
<213> ORGANISM: Artificial
<220> FEATURE:
<223> OTHER INFORMATION: CH2b3 primer

<400> SEQUENCE: 20
ggggtacctg tcatccacgg accagctga                                         29
```

```
<210> SEQ ID NO 21
<211> LENGTH: 34
<212> TYPE: DNA
<213> ORGANISM: Artificial
<220> FEATURE:
<223> OTHER INFORMATION: MJ7 primer

<400> SEQUENCE: 21
catgtgtaga ctcgcggccc agccggccat ggcc                              34

<210> SEQ ID NO 22
<211> LENGTH: 47
<212> TYPE: DNA
<213> ORGANISM: Artificial
<220> FEATURE:
<223> OTHER INFORMATION: MJ8 primer

<400> SEQUENCE: 22
catgtgtaga ttcctggccg gcctggcctg aggagacggt gacctgg                47

<210> SEQ ID NO 23
<211> LENGTH: 38
<212> TYPE: DNA
<213> ORGANISM: Artificial
<220> FEATURE:
<223> OTHER INFORMATION: Forward primer

<400> SEQUENCE: 23
tatgaagaca ccaggcccag gtaaagctgg aggagtct                          38

<210> SEQ ID NO 24
<211> LENGTH: 30
<212> TYPE: DNA
<213> ORGANISM: Artificial
<220> FEATURE:
<223> OTHER INFORMATION: Reverse primer

<400> SEQUENCE: 24
ttgttcggat cctgaggaga cggtgacctg                                   30

<210> SEQ ID NO 25
<211> LENGTH: 10
<212> TYPE: PRT
<213> ORGANISM: Artificial
<220> FEATURE:
<223> OTHER INFORMATION: IGF1R-4 peptide

<400> SEQUENCE: 25

Glu Phe Val Gly His Ile Thr Trp Ser Arg
1               5                   10

<210> SEQ ID NO 26
<211> LENGTH: 19
<212> TYPE: PRT
<213> ORGANISM: Artificial
<220> FEATURE:
<223> OTHER INFORMATION: IGF1R-4 peptide

<400> SEQUENCE: 26

Leu Ser Cys Glu Val Ser Gly Gly Thr Val Ser Pro Thr Ala Met Gly
1               5                   10                  15

Trp Phe Arg
```

<210> SEQ ID NO 27
<211> LENGTH: 15
<212> TYPE: PRT
<213> ORGANISM: Artificial
<220> FEATURE:
<223> OTHER INFORMATION: FC5 and FC5-ILIS peptide

<400> SEQUENCE: 27

Ile Thr Trp Gly Gly Asp Asn Thr Phe Tyr Ser Asn Ser Val Lys
1               5                   10                  15

<210> SEQ ID NO 28
<211> LENGTH: 9
<212> TYPE: PRT
<213> ORGANISM: Artificial
<220> FEATURE:
<223> OTHER INFORMATION: A20.1 peptide

<400> SEQUENCE: 28

Thr Thr Tyr Tyr Ala Asp Ser Val Lys
1               5

<210> SEQ ID NO 29
<211> LENGTH: 11
<212> TYPE: PRT
<213> ORGANISM: Artificial
<220> FEATURE:
<223> OTHER INFORMATION: A20.1 peptide

<400> SEQUENCE: 29

Glu Phe Val Ala Ala Gly Ser Ser Thr Gly Arg
1               5                   10

<210> SEQ ID NO 30
<211> LENGTH: 11
<212> TYPE: PRT
<213> ORGANISM: Artificial
<220> FEATURE:
<223> OTHER INFORMATION: A20.1 peptide

<400> SEQUENCE: 30

Thr Phe Ser Met Asp Pro Met Ala Trp Phe Arg
1               5                   10

<210> SEQ ID NO 31
<211> LENGTH: 26
<212> TYPE: PRT
<213> ORGANISM: Artificial
<220> FEATURE:
<223> OTHER INFORMATION: A20.1 peptide

<400> SEQUENCE: 31

Asp Glu Tyr Ala Tyr Trp Gly Gln Gly Thr Gln Val Thr Val Ser Ser
1               5                   10                  15

Gly Gln Ala Gly Gln Gly Ser Glu Gln Lys
            20                  25

<210> SEQ ID NO 32
<211> LENGTH: 11
<212> TYPE: PRT
<213> ORGANISM: Artificial
<220> FEATURE:
<223> OTHER INFORMATION: EG2 peptide

<400> SEQUENCE: 32

Asp Phe Ser Asp Tyr Val Met Gly Trp Phe Arg
1               5                   10

```
<210> SEQ ID NO 33
<211> LENGTH: 16
<212> TYPE: PRT
<213> ORGANISM: Artificial
<220> FEATURE:
<223> OTHER INFORMATION: EG2 peptide

<400> SEQUENCE: 33

Leu Glu Glu Ser Gly Gly Gly Leu Val Gln Ala Gly Asp Ser Leu Arg
1               5                   10                  15

<210> SEQ ID NO 34
<211> LENGTH: 32
<212> TYPE: PRT
<213> ORGANISM: Artificial
<220> FEATURE:
<223> OTHER INFORMATION: EG2 peptide

<400> SEQUENCE: 34

Asn Met Val Tyr Leu Gln Met Asn Ser Leu Lys Pro Glu Asp Thr Ala
1               5                   10                  15

Val Tyr Tyr Cys Ala Val Asn Ser Ala Gly Thr Tyr Val Ser Pro Arg
            20                  25                  30

<210> SEQ ID NO 35
<211> LENGTH: 14
<212> TYPE: PRT
<213> ORGANISM: Artificial
<220> FEATURE:
<223> OTHER INFORMATION: Albumin peptide

<400> SEQUENCE: 35

Ala Pro Gln Val Ser Thr Pro Thr Leu Val Glu Ala Ala Arg
1               5                   10

<210> SEQ ID NO 36
<211> LENGTH: 29
<212> TYPE: PRT
<213> ORGANISM: Artificial
<220> FEATURE:
<223> OTHER INFORMATION: Galanin-cysteamide

<400> SEQUENCE: 36

Gly Trp Thr Leu Asn Ser Ala Gly Tyr Leu Leu Gly Pro His Ala Ile
1               5                   10                  15

Asp Asn His Arg Ser Phe Ser Asp Lys His Gly Leu Thr
            20                  25

<210> SEQ ID NO 37
<211> LENGTH: 19
<212> TYPE: PRT
<213> ORGANISM: Artificial
<220> FEATURE:
<223> OTHER INFORMATION: Signal peptide

<400> SEQUENCE: 37

Met Glu Phe Gly Leu Ser Trp Val Phe Leu Val Ala Ile Leu Lys Gly
1               5                   10                  15

Val Gln Cys

<210> SEQ ID NO 38
<211> LENGTH: 371
<212> TYPE: PRT
<213> ORGANISM: Artificial
<220> FEATURE:
<223> OTHER INFORMATION: Fc-IGF1R-4 consensus fusion
```

```
<220> FEATURE:
<221> NAME/KEY: MISC_FEATURE
<222> LOCATION: (248)..(248)
<223> OTHER INFORMATION: Xaa is Glu or Gln
<220> FEATURE:
<221> NAME/KEY: MISC_FEATURE
<222> LOCATION: (250)..(250)
<223> OTHER INFORMATION: Xaa is Lys or Gln
<220> FEATURE:
<221> NAME/KEY: MISC_FEATURE
<222> LOCATION: (252)..(252)
<223> OTHER INFORMATION: Xaa is Val or Glu
<220> FEATURE:
<221> NAME/KEY: MISC_FEATURE
<222> LOCATION: (261)..(261)
<223> OTHER INFORMATION: Xaa is Ala or Pro
<220> FEATURE:
<221> NAME/KEY: MISC_FEATURE
<222> LOCATION: (270)..(270)
<223> OTHER INFORMATION: Xaa is Ala or Glu
<220> FEATURE:
<221> NAME/KEY: MISC_FEATURE
<222> LOCATION: (271)..(271)
<223> OTHER INFORMATION: Xaa is Val or Ala
<220> FEATURE:
<221> NAME/KEY: MISC_FEATURE
<222> LOCATION: (284)..(284)
<223> OTHER INFORMATION: Xaa is Val or Phe
<220> FEATURE:
<221> NAME/KEY: MISC_FEATURE
<222> LOCATION: (291)..(291)
<223> OTHER INFORMATION: Xaa is Gly or Glu
<220> FEATURE:
<221> NAME/KEY: MISC_FEATURE
<222> LOCATION: (292)..(292)
<223> OTHER INFORMATION: Xaa is Leu or Arg
<220> FEATURE:
<221> NAME/KEY: MISC_FEATURE
<222> LOCATION: (294)..(294)
<223> OTHER INFORMATION: Xaa is Phe or Trp
<220> FEATURE:
<221> NAME/KEY: MISC_FEATURE
<222> LOCATION: (296)..(296)
<223> OTHER INFORMATION: Xaa is Gly or Ser
<220> FEATURE:
<221> NAME/KEY: MISC_FEATURE
<222> LOCATION: (307)..(307)
<223> OTHER INFORMATION: Xaa is Val or Tyr
<220> FEATURE:
<221> NAME/KEY: MISC_FEATURE
<222> LOCATION: (313)..(313)
<223> OTHER INFORMATION: Xaa is Asp or Gly
<220> FEATURE:
<221> NAME/KEY: MISC_FEATURE
<222> LOCATION: (321)..(321)
<223> OTHER INFORMATION: Xaa is Asn or Ser
<220> FEATURE:
<221> NAME/KEY: MISC_FEATURE
<222> LOCATION: (322)..(322)
<223> OTHER INFORMATION: Xaa is Ala or Ser
<220> FEATURE:
<221> NAME/KEY: MISC_FEATURE
<222> LOCATION: (326)..(326)
<223> OTHER INFORMATION: Xaa is Leu or Val
<220> FEATURE:
<221> NAME/KEY: MISC_FEATURE
<222> LOCATION: (334)..(334)
<223> OTHER INFORMATION: Xaa is Lys or Arg
<220> FEATURE:
<221> NAME/KEY: MISC_FEATURE
<222> LOCATION: (335)..(335)
<223> OTHER INFORMATION: Xaa is Ala or Ser
<220> FEATURE:
<221> NAME/KEY: MISC_FEATURE
<222> LOCATION: (366)..(366)
<223> OTHER INFORMATION: Xaa is Leu or Gln
```

<400> SEQUENCE: 38

```
Glu Pro Ser Gly Pro Ile Ser Thr Ile Asn Pro Cys Pro Pro Cys Lys
1               5                   10                  15

Glu Cys His Lys Cys Pro Ala Pro Asn Leu Glu Gly Gly Pro Ser Val
            20                  25                  30

Phe Ile Phe Pro Pro Asn Ile Lys Asp Val Leu Met Ile Ser Leu Thr
        35                  40                  45

Pro Lys Val Thr Cys Val Val Asp Val Ser Glu Asp Asp Pro Asp
    50                  55                  60

Val Gln Ile Ser Trp Phe Val Asn Asn Val Glu Val His Thr Ala Gln
65                  70                  75                  80

Thr Gln Thr His Arg Glu Asp Tyr Asn Ser Thr Ile Arg Val Val Ser
                85                  90                  95

Thr Leu Pro Ile Gln His Gln Asp Trp Met Ser Gly Lys Glu Phe Lys
            100                 105                 110

Cys Lys Val Asn Asn Lys Asp Leu Pro Ser Pro Ile Glu Arg Thr Ile
        115                 120                 125

Ser Lys Ile Lys Gly Leu Val Arg Ala Pro Gln Val Tyr Ile Leu Pro
    130                 135                 140

Pro Pro Ala Glu Gln Leu Ser Arg Lys Asp Val Ser Leu Thr Cys Leu
145                 150                 155                 160

Val Val Gly Phe Asn Pro Gly Asp Ile Ser Val Glu Trp Thr Ser Asn
                165                 170                 175

Gly His Thr Glu Glu Asn Tyr Lys Asp Thr Ala Pro Val Leu Asp Ser
            180                 185                 190

Asp Gly Ser Tyr Phe Ile Tyr Ser Lys Leu Asn Met Lys Thr Ser Lys
        195                 200                 205

Trp Glu Lys Thr Asp Ser Phe Ser Cys Asn Val Arg His Glu Gly Leu
    210                 215                 220

Lys Asn Tyr Tyr Leu Lys Lys Thr Ile Ser Arg Ser Pro Gly Gly Gly
225                 230                 235                 240

Gly Ser Gly Gly Gly Gly Ser Xaa Val Xaa Leu Xaa Glu Ser Gly Gly
                245                 250                 255

Gly Leu Val Gln Xaa Gly Gly Ser Leu Arg Leu Ser Cys Xaa Xaa Ser
            260                 265                 270

Gly Gly Thr Val Ser Pro Thr Ala Met Gly Trp Xaa Arg Gln Ala Pro
        275                 280                 285

Gly Lys Xaa Xaa Glu Xaa Val Xaa His Ile Thr Trp Ser Arg Gly Thr
    290                 295                 300

Thr Arg Xaa Ala Ser Ser Val Lys Xaa Arg Phe Thr Ile Ser Arg Asp
305                 310                 315                 320

Xaa Xaa Lys Asn Thr Xaa Tyr Leu Gln Met Asn Ser Leu Xaa Xaa Glu
                325                 330                 335

Asp Thr Ala Val Tyr Tyr Cys Ala Ala Ser Thr Phe Leu Arg Ile Leu
            340                 345                 350

Pro Glu Glu Ser Ala Tyr Thr Tyr Trp Gly Gln Gly Thr Xaa Val Thr
        355                 360                 365

Val Ser Ser
    370
```

INSULIN-LIKE GROWTH FACTOR 1 RECEPTOR-SPECIFIC ANTIBODIES AND USES THEREOF

RELATED APPLICATIONS

This application is a national stage filing under 35 U.S.C. § 371 of International Application No. PCT/CA2014/000861, filed Dec. 4, 2014, which was published under PCT Article 21(2) in English, and claims the benefit under 35 U.S.C. § 119(e) of U.S. Provisional Patent Application Ser. No. 61/948,818, filed Mar. 6, 2014, the entire contents of each of which is incorporated herein by reference in its entirety.

FIELD OF THE INVENTION

The present invention relates to Insulin-Like Growth Factor 1 Receptor-specific antibodies, fragments thereof, and uses thereof. More specifically, the present invention relates to Insulin-Like Growth Factor 1 Receptor-specific antibodies and fragments thereof that transmigrate the blood-brain barrier, and uses thereof.

BACKGROUND OF THE INVENTION

Neurodegenerative diseases, such as Alzheimer's and Parkinson's disease, are an increasing burden on our ageing society because there are currently no effective treatments for these disabling conditions. Treatment as well as early diagnosis of these and other diseases that originate in the brain remain challenging because the majority of suitable therapeutic molecules and diagnostics cannot penetrate the tight and highly restrictive blood-brain barrier (BBB) (Abbott, 2013). The BBB constitutes a physical barricade that is formed by brain endothelial cells (BECs) that line the blood vessels and connect with each other through tight junctions (Abbott, 2013). The tight junctions formed between the BECs are essential for the integrity of the BBB and prevent the paracellular transport of molecules larger than 500 daltons (Da). Because brain endothelial cells exhibit very low pinocytosis rates (Abbott, 2013), transcellular transport of larger molecules is limited to the highly specific receptor mediated transcytosis (RMT) pathway, and the passive, charge-based adsorption mediated transcytosis (Abbott, 2013; Pardridge, 2002). Additionally, the high density of efflux pumps, such as P-glycoprotein or the multi-drug resistance protein-1 (MDR-1), contribute to the removal of unwanted substances from the brain (Abbott, 2013).

While all these characteristics protect the brain from pathogens and toxins, they equally prevent the entry of most therapeutics. In fact, less than 5% of small molecule therapeutics and virtually none of the larger therapeutics can cross the BBB in pharmacologically relevant concentrations (i.e., sufficient to engage a central nervous system (CNS) target and elicit pharmacologic/therapeutic response) unless they are specifically 'ferried', that is, coupled to a transporter molecule. Due to the lack of effective 'carriers' to transport molecules across the BBB, numerous drugs against neurodegenerative diseases have been 'shelved' or eliminated from further development as they cannot be delivered to the brain in sufficient amount.

Different approaches to deliver larger molecules into the brain have been explored. For example, the integrity of the BBB may be disrupted, resulting in a leaky BBB, which in turn allows for unrestricted, paracellular entry of larger molecules into the brain. Tight junctions can be successfully loosened or disrupted by various approaches. For example, injection of substances that induce osmotic shock (for example, mannitol, hypertonic solutions) into the blood stream causes cell shrinkage and results in the disruption of tight junctions, therefore severely compromising the BBB (Guillaume, 2010). Other modulators of tight junctions include alkylglycerols, bradykinin and several analogues thereof, as well as viruses that modulate expression of proteins involved in maintaining the tight junctions (Erdlenbruch et al., 2003; Preston et al., 2008; Gan et al., 2013). A more localized disruption of the BBB is possible through application of ultrasound (Nhan et al., 2013). However, the periods during which the BBB is disrupted are sufficient to alter brain homeostasis and allow harmful chemicals, toxins and pathogens to enter the brain; this can result in serious side-effects, e.g., seizures and brain swelling, infection and possibly permanent neuropathological changes. As would be evident to those of skill in the art, repeated treatments with these techniques for chronic and diffuse brain diseases affecting multiple brain regions are not practical. Most of these treatments are costly, necessitate hospitalisation, and some approaches require anesthesia.

Another approach for circumventing the BBB is direct injection of therapeutic molecules into the cerebrospinal fluid (CSF), the parenchymal space, or other parts of the brain. Several delivery methods have been developed, including: intracerebral (intra-parenchymal), intraventricular, and intrathecal delivery via infusion or convection-enhanced diffusion (CED) pumps. However, any type of direct injection into the brain or intracerebral implant is an invasive and costly procedure, as it requires hospitalization, anesthesia, and often surgery. Moreover, the poor diffusion rates of the therapeutics, particularly large biologics, within brain parenchyma limit the penetration of therapeutics to only small areas surrounding the site of injection/implantation. The correct placement of injections, catheters, and implants is challenging yet crucial to achieve diffusion of the drug to the targeted region of the brain. Additionally, catheters and implants provide a site for infection and/or immune response against the foreign material.

In another attempt to increase delivery across the BBB, CNS drugs have been modified to increase their brain uptake. Such modifications can include a change of their surface charge, a reduction in molecule size, and change to the lipohilicity of the drugs. However, any modifications to increase brain penetration are also likely to alter the overall pharmacology of the drug, including its desired activity and/or specificity. In addition, lipophilic molecules are more prone to being exported from the brain through the P-glycoprotein efflux pump.

Finally, endogenous transport mechanisms across the BBB have been exploited. Physiological mechanisms that allow transport of large molecules across the BBB can be divided into the highly specific receptor mediated transcytosis (RMT) and the non-specific charge based adsorptive mediated endocytosis pathways. Endocytosis is triggered upon binding of the specific ligand to its receptor, or upon electrostatic interaction between the cationic ligand or drug and the anionic functional groups on the brain endothelial cell surface (luminal side), respectively. Subsequently, the newly formed endosome is transcytosed across the cell to the abluminal side, to release its cargo.

Because adsorptive mediated transcytosis is non-specific, charge-mediated interaction, it occurs in all vascular beds and organs, limiting the availability of drug for brain delivery. Therefore, exploiting the RMT pathway remains the only physiological, non-invasive yet highly receptor-specific brain delivery method.

Only a few receptors are presently known to undergo RMT at the BBB and 'ferry' across their natural ligands: the well-studied transferrin receptor (TfR), the insulin receptor (IR), low-density lipoprotein receptor related proteins 1 and 2 (LRP-1 and -2), diphtheria toxin receptor, and TMEM30A. Peptides, natural ligands, and antibodies or antibody fragments have been developed that bind to these receptors (Pardridge et al., 1991; Yu et al., 2011; Muruganandam et al., 2001; Abulrob et al., 2005; Demeule, 2008; Sumbria et al., 2013), functioning as drug-to-brain transporters that utilize endogenous RMT pathways. However, to date only a single peptide (Angiopep ANG1005, targeting LRP-1) has been analyzed in phase I clinical studies, while other candidates are being studied in laboratory settings. The RMT pathway appears to be the most promising pathway for drug transport to the brain, but current approaches have limitations, including: non-selective expression of the target receptor at the BBB, competition between the carrier and the natural ligands to the receptor, ineffective transcytosis of a receptor as well as lysosomal degradation of endocytosed carriers (Xiao and Gun, 2013).

The lack of high-capacity and high-selectivity BBB carriers delays the development of new therapeutics and diagnostics for diseases originating in the brain, including brain tumors and neurodegenerative diseases. There is clearly a need for a non-invasive method to deliver small and large therapeutic and diagnostic molecules in pharmacologically efficacious doses into the brain without disrupting the physiology and homeostasis of the BBB.

SUMMARY OF THE INVENTION

The present invention relates to Insulin-Like Growth Factor 1 Receptor (IGF1R)-specific antibodies and uses thereof. More specifically, the present invention relates to Insulin-Like Growth Factor 1 Receptor-specific antibodies and fragments thereof that transmigrate the blood-brain barrier, and uses thereof.

The present invention provides isolated or purified antibodies or fragments thereof specifically binding to an Insulin-Like Growth Factor 1 Receptor (IGF1R) epitope, wherein the antibody or fragment thereof transmigrates the blood-brain barrier, and wherein the epitope is specifically bound by the antibody of SEQ ID NO:5. The IGF1R epitope may be in the extracellular domain of IGF1R.

The present invention further provides isolated or purified antibodies or fragment thereof, comprising
a complementarity determining region (CDR) 1 sequence of GGTVSPTA (SEQ ID NO:1);
a CDR2 sequence of ITWSRGTT (SEQ ID NO:2); and
a CDR3 sequence of AASTFLRILPEESAYTY (SEQ ID NO:3),
wherein the antibody or fragment thereof specifically binds to the Insulin-Like Growth Factor 1 Receptor (IGF1R).

For example, and without wishing to be limiting in any manner, the isolated or purified antibody or fragment thereof specific for IGF1R may be
$X_1VX_2LX_3ESGGGLVQX_4GGSLRLSCX_5X_6SGGTVS$
PTAMGW$X_7$RQAPGK$X_8X_9$EX$_{10}$V$X_{11}$HITWSRGTT
R$X_{12}$ASSVK$X_{13}$RFTISRD$X_{14}X_{15}$KNT$X_{16}$YLQMN
SL$X_{17}X_{18}$EDTAVYYCAASTFLRILPEESAYTYWG
QGT $X_{19}$VTVSS (SEQ ID NO:4), where $X_1$ is E or Q; $X_2$ is K or Q; $X_3$ is V or E; $X_4$ is A or P; $X_5$ is A or E; $X_6$ is V or A; $X_7$ is V or F; $X_8$ is G or E; $X_6$ is L or R;
$X_{10}$ is F or W; $X_{11}$ is G or S; $X_{12}$ is V or Y; $X_{13}$ is D or G; $X_{14}$ is N or S; $X_{15}$ is A or S; $X_{16}$ is L or V; $X_{17}$ is K or R; $X_{18}$ is A or S; and $X_{19}$ is L or Q,
or a sequence substantially identical thereto. In more specific, non-limiting examples, the isolated or purified antibody may comprise a sequence selected from the group consisting of:

(SEQ ID NO: 5)
QVKLEESGGGLVQAGGSLRLSCEVSGGTVSPTAMGWFRQAPGKEREFVGH

ITWSRGTTRVASSVKDRFTISRDSAKNTVYLQMNSLKSEDTAVYYCAAST

FLRILPEESAYTYWGQGTQVTVSS, referred to herein as

IGF1R-4;

(SEQ ID NO: 6)
QVQLVESGGGLVQPGGSLRLSCAVSGGTVSPTAMGWVRQAPGKGLEWVG

HITWSRGTTRYASSVKGRFTISRDNSKNTVYLQMNSLRAEDTAVYYCAAS

TFLRILPEESAYTYWGQGTLVTVSS, referred to herein as

IGF1R-4_H2;

(SEQ ID NO: 7)
QVQLVESGGGLVQPGGSLRLSCAVSGGTVSPTAMGWFRQAPGKGLEFVGH

ITWSRGTTRYASSVKGRFTISRDNSKNTVYLQMNSLRAEDTAVYYCAAST

FLRILPEESAYTYWGQGTLVTVSS, referred to herein as

IGF1R-4_H3;

(SEQ ID NO: 8)
QVQLVESGGGLVQPGGSLRLSCAVSGGTVSPTAMGWFRQAPGKGLEFVGH

ITWSRGTTRYASSVKGRFTISRDSSKNTVYLQMNSLRAEDTAVYYCAAST

FLRILPEESAYTYWGQGTLVTVSS, referred to herein as

IGF1R-4_H4;

(SEQ ID NO: 9)
QVQLVESGGGLVQPGGSLRLSCAVSGGTVSPTAMGWFRQAPGKEREFVGH

ITWSRGTTRYASSVKGRFTISRDSSKNTVYLQMNSLRAEDTAVYYCAAST

FLRILPEESAYTYWGQGTLVTVSS, referred to herein as

IGF1R-4_H5;

and
or a sequence substantially identical thereto.

The isolated or purified antibody or fragment thereof as described above may be a single-domain antibody (sdAb); the sdAb may be of camelid origin.

The isolated or purified antibody or fragment thereof of the present invention may be presented in a multivalent display format. In a multivalent display format, the antibody or fragment thereof may be linked to a Fc fragment; the Fc fragment may be the mouse Fc2b or human Fc1. For example, and without wishing to be limiting in any manner, the isolated or purified antibody or fragment thereof in multivalent display may comprise the sequence of SEQ ID NO: 10 (referred to herein as IGF1R-4 consensus-Fc fusion), SEQ ID NO:38 (referred to herein as Fc-IGF1R-4 consensus fusion), or 11 (referred to herein as IGF1R-4-Fc fusion).

The isolated or purified antibody or fragment thereof as described herein may transmigrate the blood-brain barrier.

The present invention also provides a nucleic acid molecule encoding the isolated or purified antibody or fragment thereof as described herein. A vector comprising the nucleic acid molecule as just described is also provided.

The isolated or purified antibody or fragment thereof as described herein may be immobilized onto a surface.

The present invention further provides the isolated or purified antibody or fragment thereof as described herein linked to a cargo molecule; the cargo molecule may have a molecular weight in the range of about 1 kD to about 200 kDa. The cargo molecule linked to the antibody or fragment thereof may be a detectable agent, a therapeutic, a drug, a peptide, a growth factor, a cytokine, a receptor trap, a chemical compound, a carbohydrate moiety, an enzyme, an antibody or fragments thereof, a DNA-based molecule, a viral vector, or a cytotoxic agent; one or more liposomes or nanocarriers loaded with a detectable agent, a therapeutic, a drug, a peptide, an enzyme, and antibody or fragments thereof, a DNA-based molecule, a viral vector, or a cytotoxic agent; or one or more nanoparticle, nanowire, nanotube, or quantum dots.

Additionally, the present invention provides a composition comprising one or more than one isolated or purified antibody or fragment thereof as described herein and a pharmaceutically-acceptable carrier, diluent, or excipient.

An in vitro method of detecting IGF1R is also provided, the method comprising
 a) contacting a tissue sample with one or more than one isolated or purified antibody or fragment thereof of as described herein linked to a detectable agent; and
 b) detecting the detectable agent detecting the detectable agent linked to the antibody or fragment thereof bound to IGF1R in the tissue sample.

In the method described above, the sample may be a serum sample, a vascular tissue sample, tumour tissue sample, or a brain tissue sample from a human or animal subject. In the method as described, the step of detecting (steb b)) may be performed using optical imaging, immunohistochemistry, molecular diagnostic imaging, ELISA, imaging mass spectrometry, or other suitable method.

Further provided is an in vivo method of detecting IGF1R expression in a subject, the method comprising:
 a) administering one or more than one isolated or purified antibody or fragment thereof as described herein linked to a detectable agent to the subject; and
 b) detecting the detectable agent linked to the antibody or fragment thereof bound to IGF1R.

In the method described above, the step of detecting (steb b)) may be performed using PET (positron emission tomography), SPECT (single-photon emission computed tomography), fluorescence imaging, or any other suitable method.

Presently provided is a method of transporting a molecule of interest across the blood-brain barrier (BBB), the method comprising:
 a) administering one or more than one isolated or purified antibody or fragment thereof as described herein linked to the molecule of interest to a subject, where the antibody or fragment thereof transmigrates the blood-brain barrier,
wherein the one or more than one antibody or fragment thereof ferries the molecule of interest across the BBB. In the method as just described, the molecule of interest may have a molecular weight in the range of about 1 kD to about 200 kDa; the molecule of interest may be a detectable agent, a therapeutic, a drug, a peptide, a growth factor, a cytokine, a receptor trap, a chemical compound, a carbohydrate moiety, an enzyme, an antibody or fragment thereof, a DNA-based molecule, a viral vector, or a cytotoxic agent; one or more liposomes or nanocarriers loaded with a detectable agent, a therapeutic, a drug, a peptide, an enzyme, an antibody or fragment thereof, or a cytotoxic agent; or one or more nanoparticle, nanowire, nanotube, or quantum dots. In the method as described, the administration may be intravenous (iv), subcutaneous (sc), or intramuscular (im).

The invention also encompasses a method of quantifying an amount of a cargo molecule delivered across the BBB of a subject, wherein the cargo molecule is linked to one or more than one isolated or purified antibody or fragment thereof as described herein, the method comprising
 a) collecting cerebrospinal fluid (CSF) from the subject; and
 b) using targeted proteomics methods to quantify the amount of the cargo molecule linked to one or more than one isolated or purified antibody or fragment in the CSF.

The cargo molecule may be any desired molecule, including the cargo molecules previously described; the antibody or fragment thereof transmigrates the BBB; and the molecule may be "linked" to the antibody or fragment thereof, as previously described. In the above method, the CSF is collected from a subject using any suitable method known in the art. The amount of CSF required for targeted proteomics method in step b) may be between about 1 to 10 µl. The targeted proteomics methods used to quantify the amount of the one or more than antibody or fragment thereof linked to the cargo molecule may be any suitable method known in the art. For example and without wishing to be limiting, the targeted proteomics method may be a mass spectrometry method, such as multiple reaction monitoring-isotype labeled internal standards (MRM-ILIS).

The poor delivery of diagnostics or drugs across the tight and highly selective BBB compromises the development of treatments for brain diseases, such as, but not limiting to, brain tumors and neurodegenerative diseases. The lack of carriers to transport molecules across the BBB delays the development of new therapeutics and diagnostics for such diseases. As described herein, an IGF1R-binding $V_HH$ has been produced that provides an effective transport platform for delivery of drugs conjugated to the antibody across the BBB to their targets in the brain. The presently described antibody exploits the natural RMT pathway of the IGF1R from the luminal to abluminal side of the BBB-forming brain endothelial cells. Following binding of the antibody to IGF1R, RMT is initiated and the antibody, together with a conjugated molecule (cargo), is transcytosed through the cell to the abluminal side where they are both released into the brain microenvironment. The anti-IGF1R $V_HH$ was confirmed to bind to IGF1R (FIG. 3C), internalize into BBB cells (FIG. 4), and cross to abluminal side of the in vitro BBB model (FIG. 6B). Drug-to-brain delivery studies in vivo also showed that the IGF1R $V_HH$ 'carried' a conjugated peptide (Galanin; about 3 kDa) as well as a large protein fusion (about 80 kDa) across the BBB (FIGS. 9A and B; FIG. 9C).

The results also show that the anti-IGF1R $V_HH$ can be expressed in fusion with Fc (fragment crystallisable) fragment to prolong circulation half-life by about 75 fold (about 25 h compared to about 20 min for $V_HH$ alone). This high molecular weight fusion construct (about 80 kDa) is also efficiently transported across the BBB. The long plasma half-life increases CSF exposure of the IGF1R $V_HH$-mFc (mFc=mouse Fc) conjugate significantly compared to the $V_HH$ alone and is useful as a BBB delivery carrier for the treatment of chronic diseases with targets in the CNS. The conjugate is readily detected in brain parenchyma using immunofluorescence detection. The results demonstrate that the IGF1R $V_HH$ carrier can "ferry" large molecules (similar in size to: antibodies, enzymes, growth factors, peptides, cytokines, receptor traps) across the BBB.

Thus, the antibody-delivery may not only be useful for short term treatment (e.g. epileptic seizure), but may also be useful for medium-term (e.g. cancer) and long-term (e.g. Alzheimer's or Parkinson's disease) treatments.

Additional aspects and advantages of the present invention will be apparent in view of the following description. The detailed descriptions and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 1 is a schematic diagram of the insulin-like growth factor 1 receptor (IGF1R). The IGF1R is found on the cell surface, and comprises two subunits: the alpha subunit and the beta subunit. The alpha subunit (comprising an extracellular part with the insulin-like growth factor 1 binding site) is connected by a disulphide bond to the beta subunit (comprising a small extracellular domain, a transmembrane region, and an intracellular portion). The IGF1 receptor can form a dimer. A 933 amino acid long fragment comprising the alpha subunit and the extracellular portion of the beta subunit, as indicated within the box, (M1-F933, SwissProt Accession No. P08069; see FIG. 2) was recombinantly produced and used for immunization of a llama.

FIG. 2 shows the sequence of IGF1R (SwissProt Accession No. P08069; SEQ ID NO: 12). The 933 amino acid long protein fragment used for immunization and panning is shown in bold; the full ectodomain is 2 amino acids longer. The furin cleavage site, separating alpha and beta subunits, is shown in italicized lowercase letters. The signal peptide is shown in bold italics.

FIG. 4 shows imaging results of cell uptake of Cy-5.5-labeled IGF1R-4 $V_HH$ and control $V_HH$. Cy5.5-labeled IGF1R-4 $V_HH$ (or FC5 $V_HH$ as a positive control; Muruganandam et al., 2002; Haqqani et al., 2012) were incubated with SV40 immortalized rat brain endothelial cells (svARBEC) at 4° C. (top panels) or at 37° C. (bottom panels) to assess whether IGF1R-4 is internalized passively (4° C.) or through active mechanisms (37° C.) such as receptor mediated endocytosis. Co-staining with wheat germ agglutinin and DAPI was carried out to visualize the cell surface and the nucleus, respectively. Top panel: When incubated at 4° C., IGF1R-4 and FC5 $V_HH$ were found outside the cells (arrowheads), bound to cell membrane (co-localized with the wheat germ agglutinin). Bottom panel: At 37° C. both FC5 and IGF1R-4 $V_HH$ accumulated inside the cells in vesicle-like structures (arrowheads), likely endosomes, suggesting internalization through an active transport mechanism.

FIG. 5A shows the sequence for the C-terminal fusion of IGF1R-4 $V_HH$ with the murine Fc fragment (IGF1R-4-mFc; SEQ ID NO: 11). A schematic representation of the assembled fusion protein is shown in FIG. 5B. The IGF1R-4 $V_HH$ are shown in black and the murine Fc (CH2 and CH3) are shown in grey in FIGS. 5A and 5B.

FIG. 9 shows IGF1R-4-mediated brain delivery of the chemically conjugated peptide Galanin.

FIG. 12 shows that IGF1R-4 does not interfere with insulin or IGF-1 signaling through either the insulin receptor or IGF1R.

DETAILED DESCRIPTION OF THE INVENTION

Figure 3A:
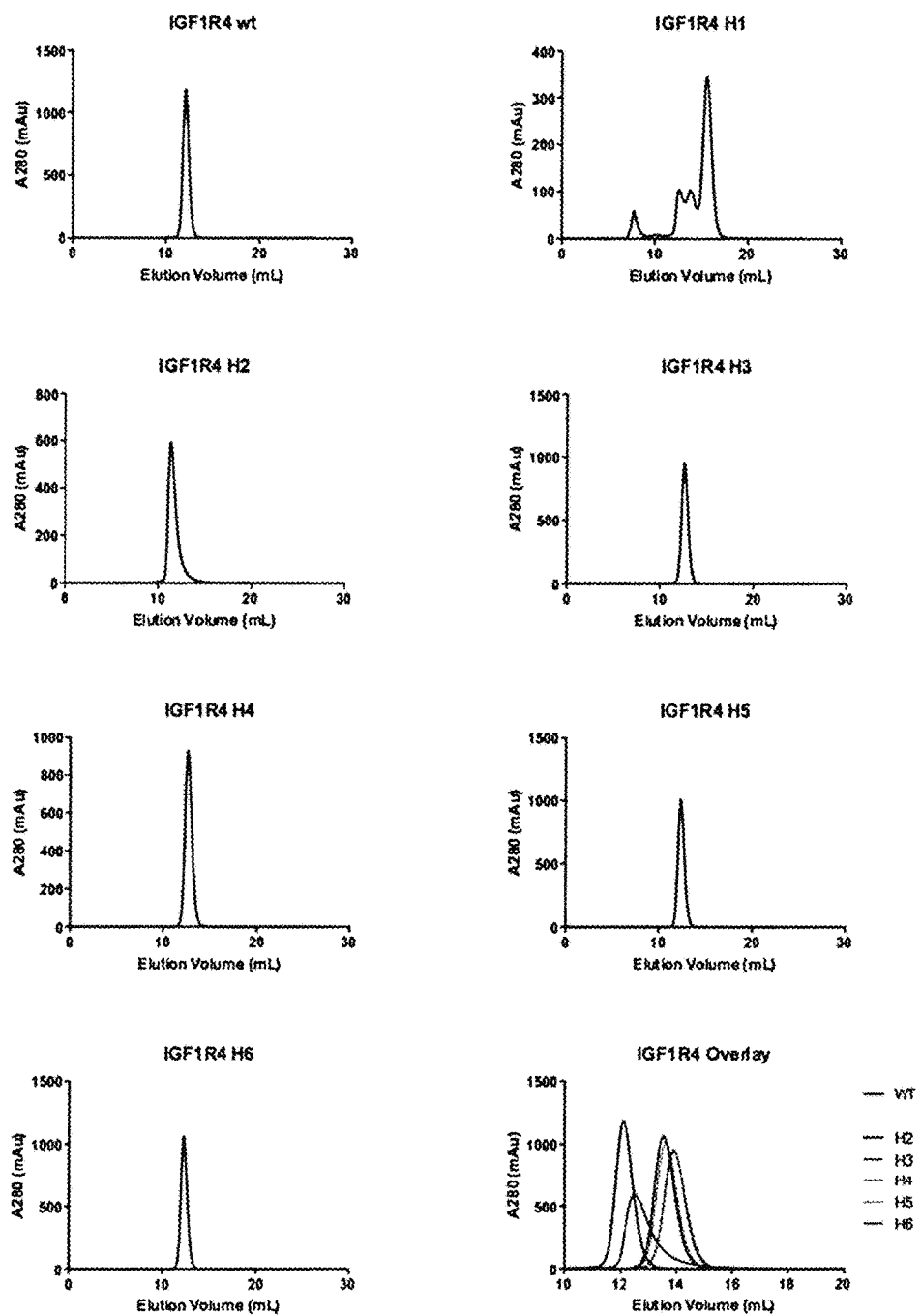
FIG. 3A shows a size exclusion chromatogram of the IGF1R-binding $V_HH$ IGF1R-4 and its humanized variants (H1, H2, H3, H4, H5, H6) run through a Superdex 75 column. The profile suggests that all the $V_HH$s except IGF1R H1 are monomeric and non-aggregating.

The present invention relates to Insulin-Like Growth Factor 1 Receptor-specific antibodies, fragments thereof, and uses thereof. More specifically, the present invention relates to Insulin-Like Growth Factor 1 Receptor-specific antibodies or fragments thereof that transmigrate the blood-brain barrier, and uses thereof.

The present invention provides isolated or purified antibodies or fragments thereof specifically binding to an Insulin-Like Growth Factor 1 Receptor (IGF1R) epitope, wherein the antibody or fragment thereof transmigrates the blood-brain barrier, and wherein the epitope is specifically bound by the antibody of SEQ ID NO:5. The IGF1R epitope may be in the extracellular domain of IGF1R.

The present invention provides an isolated or purified antibody or fragment thereof, comprising a complementarity determining region (CDR) 1 sequence of GGTVSPTA (SEQ ID NO:1);
a CDR2 sequence of ITWSRGTT (SEQ ID NO:2); and
a CDR3 sequence of AASTFLRILPEESAYTY (SEQ ID NO:3),
wherein the antibody or fragment thereof specifically binds to the Insulin-Like Growth Factor 1 Receptor (IGF1R).

The term "antibody", also referred to in the art as "immunoglobulin" (Ig), as used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen-binding determinants of the molecule, and thus determines the specificity of an antibody for its target antigen. The majority of sequence variability occurs in six hypervariable regions, three each per variable heavy ($V_H$) and light ($V_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the $V_H$ and $V_L$ domains. Chothia and Lesk (1987) define the "hypervariable loops" (H or L) based on the location of the structural loop regions in the $V_H$ and $V_L$ domains. As these individual schemes define CDR and hypervariable loop regions that are adjacent or overlapping, those of skill in the antibody art often utilize the terms "CDR" and "hypervariable loop" interchangeably, and they may be so used herein. The CDR/loops are referred to herein according to the more recent IMGT numbering system (Lefranc, M.-P. et al., 2003), which was developed to facilitate comparison of variable domains. In this system, conserved amino acids (such as Cys23, Trp41, Cys104, Phe/Trp118, and a hydrophobic residue at position 89) always have the same position. Additionally, a standardized delimitation of the framework regions (FR1: positions 1 to 26; FR2: 39 to 55; FR3: 66 to 104; and FR4: 118 to 129) and of the CDR (CDR1: 27 to 38, CDR2: 56 to 65; and CDR3: 105 to 117) is provided.

An "antibody fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, single-chain Fv (scFv; a molecule consisting of $V_L$ and $V_H$ connected with a peptide linker), Fab, F(ab')$_2$, single domain antibody (sdAb; a fragment composed of a single $V_L$ or $V_H$), and multivalent presentations of any of these. Antibody fragments such as those just described may require linker sequences, disulfide bonds, or other type of covalent bond to link different portions of the fragments; those of skill in the art will be familiar with the requirements of the different types of fragments and various approaches and various approaches for their construction.

In a non-limiting example, the antibody fragment may be an sdAb derived from naturally-occurring sources. Heavy chain antibodies of camelid origin (Hamers-Casterman et al, 1993) lack light chains and thus their antigen binding sites consist of one domain, termed $V_H$H. sdAb have also been observed in shark and are termed $V_{NAR}$ (Nuttall et al, 2003). Other sdAb may be engineered based on human Ig heavy and light chain sequences (Jespers et al, 2004; To et al, 2005). As used herein, the term "sdAb" includes those sdAb directly isolated from $V_H$, $V_H$H, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, camelization, or other methods of antibody engineering. Also encompassed by the present invention are homologues, derivatives, or fragments that retain the antigen-binding function and specificity of the sdAb.

SdAb possess desirable properties for antibody molecules, such as high thermostability, high detergent resistance, relatively high resistance to proteases (Dumoulin et al, 2002) and high production yield (Arbabi-Ghahroudi et al, 1997); they can also be engineered to have very high affinity by isolation from an immune library (Li et al, 2009) or by in vitro affinity maturation (Davies & Riechmann, 1996). Further modifications to increase stability, such as the introduction of non-canonical disulfide bonds (Hussack et al, 2011; Kim et al, 2012), may also be brought to the sdAb.

A person of skill in the art would be well-acquainted with the structure of a single-domain antibody (see, for example, 3DWT, 2P42 in Protein Data Bank). An sdAb comprises a single immunoglobulin domain that retains the immunoglobulin fold; most notably, only three CDR/hypervariable loops form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3, and numbered as defined by Lefranc, M.-P. et al. (2003).

The antibody or fragment thereof of the present invention is specific for Insulin-Like Growth Factor 1 Receptor (IGF1R), a receptor found on cell surfaces. The IGF1R comprises an alpha subunit, which comprises an extracellular part having the insulin-like growth factor 1 binding site, connected by a disulphide bond to the beta subunit, which comprises a small extracellular domain, a transmembrane region, and an intracellular portion. The IGF1 receptor assembles into a homo-dimer or may form a heterodimer with the insulin receptor. The sequence of IGF1R may be, but is not limited to that shown in FIG. 2 (SwissProt Accession No. P08069; SEQ ID NO:12), or a sequence substantially identical thereto.

The antibody or fragment thereof as described herein should not interfere with signaling through the Insulin Receptor (IR) or IGF1R. Specifically, the antibodies or fragments thereof as described herein should not inhibit AKT phosphorylation induced by insulin, nor should they induce phosphorylation of the IR on their own or inhibit insulin-induced signaling; additionally, the antibodies or fragments thereof described herein should not inhibit IGF-1-induced phosphorylation of IGF1R. Moreover, they should not bind to the Insulin Receptor.

As previously stated, the antibody or fragment thereof may be an sdAb. The sdAb may be of camelid origin or derived from a camelid $V_HH$, and thus may be based on camelid framework regions; alternatively, the CDR described above may be grafted onto $V_{NAR}$, $V_HH$, $V_H$ or $V_L$ framework regions. In yet another alternative, the hypervariable loops described above may be grafted onto the framework regions of other types of antibody fragments (Fv, scFv, Fab) of any source (for example, mouse) or proteins of similar size and nature onto which CDR can be grafted (for example, see Nicaise et al, 2004).

The present invention further encompasses an antibody or fragment that is "humanized" using any suitable method known in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the CDR defined herein may be fused or grafted to a human variable region ($V_H$, or $V_L$), to other human antibody (IgA, IgD, IgE, IgG, and IgM), to other human antibody fragment framework regions (Fv, scFv, Fab), or to other proteins of similar size and nature onto which CDR can be grafted (Nicaise et al, 2004). In such a case, the conformation of said one or more than one hypervariable loop is likely preserved, and the affinity and specificity of the sdAb for its target (i.e., IGF1R) is likely minimally affected. CDR grafting is known in the art and is described in at least the following: U.S. Pat. No. 6,180,370, U.S. Pat. No. 5,693,761, U.S. Pat. No. 6,054,297, U.S. Pat. No. 5,859,205, and European Patent No. 626390. Veneering, also referred to in the art as "variable region resurfacing", involves humanizing solvent-exposed positions of the antibody or fragment; thus, buried non-humanized residues, which may be important for CDR conformation, are preserved while the potential for immunological reaction against solvent-exposed regions is minimized. Veneering is known in the art and is described in at least the following: U.S. Pat. No. 5,869,619, U.S. Pat. No. 5,766,886, U.S. Pat. No. 5,821,123, and European Patent No. 519596. Persons of skill in the art would also be amply familiar with methods of preparing such humanized antibody fragments and humanizing amino acid positions.

For example, and without wishing to be limiting in any manner, the isolated or purified antibody or fragment thereof specific for IGF1R may be $X_1VX_2LX_3ESGGGLVQX_4GGSLRLSCX_5X_6SGGTVS$ PTAMGW$X_7$RQAPGK$X_8X_9$EX$_{10}$VX$_{11}$HITWSRGT TR$X_{12}$ASSVK$X_{13}$RFTISRD$X_{14}X_{15}$KNT$X_{16}$YLQM NSL$X_{17}X_{18}$EDTAVYYCAASTFLRILPEESAYTYW GQGT $X_{19}$VTVSS (SEQ ID NO:4), where $X_1$ is E or Q; $X_2$ is K or Q; $X_3$ is V or E; $X_4$ is A or P; $X_5$ is A or E; $X_6$ is V or A; $X_7$ is V or F; $X_8$ is G or E; $X_3$ is L or R; $X_{10}$ is F or W; $X_{11}$ is G or S; $X_{12}$ is V or Y; $X_{13}$ is D or G; $X_{14}$ is N or S; $X_{15}$ is A or S; $X_{16}$ is L or V; $X_{17}$ is K or R; $X_{18}$ is A or S; and $X_{19}$ is L or Q, or a sequence substantially identical thereto. Alternatively, the isolated or purified antibody may comprise a sequence selected from the group consisting of:

```
                                         (SEQ ID NO: 5)
QVKLEESGGGLVQAGGSLRLSCEVSGGTVSPTAMGWFRQAPGKEREFVGH

ITWSRGTTRVASSVKDRFTISRDSAKNTVYLQMNSLKSEDTAVYYCAAST

FLRILPEESAYTYWGQGTQVTVSS, referred to herein as

IGF1R-4;

(SEQ ID NO: 6)
QVQLVESGGGLVQPGGSLRLSCAVSGGTVSPTAMGWVRQAPGKGLEWVGH

ITWSRGTTRYASSVKGRFTISRDNSKNTVYLQMNSLRAEDTAVYYCAAST

FLRILPEESAYTYWGQGTLVTVSS, referred to herein as

IGF1R-4_H2;

(SEQ ID NO: 7)
QVQLVESGGGLVQPGGSLRLSCAVSGGTVSPTAMGWFRQAPGKGLEFVGH

ITWSRGTTRYASSVKGRFTISRDNSKNTVYLQMNSLRAEDTAVYYCAAST

FLRILPEESAYTYWGQGTLVTVSS, referred to herein as

IGF1R-4_H3;

(SEQ ID NO: 8)
QVQLVESGGGLVQPGGSLRLSCAVSGGTVSPTAMGWFRQAPGKGLEFVGH

ITWSRGTTRYASSVKGRFTISRDSSKNTVYLQMNSLRAEDTAVYYCAAST

FLRILPEESAYTYWGQGTLVTVSS, referred to herein as

IGF1R-4_H4;

(SEQ ID NO: 9)
QVQLVESGGGLVQPGGSLRLSCAVSGGTVSPTAMGWFRQAPGKEREFVGH

ITWSRGTTRYASSVKGRFTISRDSSKNTVYLQMNSLRAEDTAVYYCAAST

FLRILPEESAYTYWGQGTLVTVSS, referred to herein as

IGF1R-4_H5;
``` and or a sequence substantially identical thereto.

A substantially identical sequence may comprise one or more conservative amino acid mutations. It is known in the art that one or more conservative amino acid mutations to a reference sequence may yield a mutant peptide with no substantial change in physiological, chemical, physicochemical or functional properties compared to the reference sequence; in such a case, the reference and mutant sequences would be considered "substantially identical" polypeptides. A conservative amino acid substitution is defined herein as the substitution of an amino acid residue for another amino acid residue with similar chemical properties (e.g. size, charge, or polarity). These conservative amino acid mutations may be made to the framework regions of the sdAb while maintaining the CDR sequences listed above and the overall structure of the CDR of the antibody or fragment; thus the specificity and binding of the antibody are maintained.

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blasta BLAST-P, Blast-N, or FASTA-N, or any other appropriate software that is known in the art.

The substantially identical sequences of the present invention may be at least 90% identical; in another example, the substantially identical sequences may be at least 90, 91, 92, 93, 94, 95, 96, 97, 98, 99, or 100% identical, or any percentage therebetween, at the amino acid level to sequences described herein. Importantly, the substantially identical sequences retain the activity and specificity of the reference sequence. In a non-limiting embodiment, the difference in sequence identity may be due to conservative amino acid mutation(s). In a non-limiting example, the present invention may be directed to an antibody or fragment thereof comprising a sequence at least 95%, 98%, or 99% identical to that of the antibodies described herein.

The antibody or fragment thereof of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection/purification tag (for example, but not limited to c-Myc, $His_5$, or $His_6$), or a combination thereof. In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags, or may serve as a detection/purification tag.

The antibody or fragment thereof of the present invention may also be in a multivalent display format, also referred to herein as multivalent presentation. Multimerization may be achieved by any suitable method of known in the art. For example, and without wishing to be limiting in any manner, multimerization may be achieved using self-assembly molecules such as those described in Zhang et al (2004a; 2004b) and WO2003/046560, where pentabodies are produced by expressing a fusion protein comprising the antibody or fragment thereof of the present invention and the pentamerization domain of the B-subunit of an $AB_5$ toxin family (Merritt & Hol, 1995). A multimer may also be formed using the multimerization domains described by Zhu et al. (2010); this form, referred to herein as a "combody" form, is a fusion of the antibody or fragment of the present invention with a coiled-coil peptide resulting in a multimeric molecule (Zhu et al., 2010). Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielson et al, 2000), c-jun/Fos interaction (de Kruif & Logtenberg, 1996), "Knob into holes" interaction (Ridgway et al, 1996).

Another method known in the art for multimerization is to dimerize the antibody or fragment thereof using an Fc domain, for example, but not limited to human Fc domains. The Fc domains may be selected from various classes including, but not limited to, IgG, IgM, or various subclasses including, but not limited to IgG1, IgG2, etc. In this approach, the Fc gene in inserted into a vector along with the sdAb gene to generate a sdAb-Fc fusion protein (Bell et al, 2010; lqbal et al, 2010); the fusion protein is recombinantly expressed then purified. For example, and without wishing to be limiting in any manner, multivalent display formats may encompass chimeric formats of anti-IGF1R-4 $V_HH$ linked to an Fc domain, or bi- or tri-specific antibody fusions with two or three anti-IGF1R-4 $V_HH$ recognizing unique epitopes. Such antibodies are easy to engineer and to produce, can greatly extend the serum half-life of sdAb, and may be excellent tumor imaging reagents (Bell et al., 2010).

The Fc domain in the multimeric complex as just described may be any suitable Fc fragment known in the art. The Fc fragment may be from any suitable source; for example, the Fc may be of mouse or human origin. In a specific, non-limiting example, the Fc may be the mouse Fc2b fragment or human Fc1 fragment (Bell et al, 2010; Iqbal et al, 2010). The Fc fragment may be fused to the N-terminal or C-terminal end of the anti-IGF1R-3 $V_HH$ or humanized versions of the present invention. In a specific, non-limiting example, the multimerized isolated or purified antibody or fragment as just described may comprise the sequence of SEQ ID NO:10, 38, or 11.

Each subunit of the multimers described above may comprise the same or different antibodies or fragments thereof of the present invention, which may have the same or different specificity. Additionally, the multimerization domains may be linked to the antibody or antibody fragment using a linker, as required; such a linker should be of sufficient length and appropriate composition to provide flexible attachment of the two molecules, but should not hamper the antigen-binding properties of the antibody.

The antibody or fragment thereof as described herein may transmigrate across the blood brain barrier. The brain is separated from the rest of the body by a specialized endothelial tissue known as the blood-brain barrier (BBB). The endothelial cells of the BBB are connected by tight junctions and efficiently prevent many therapeutic compounds from entering the brain. In addition to low rates of vesicular transport, one specific feature of the BBB is the existence of enzymatic barrier(s) and high level(s) of expression of ATP-dependent transporters on the abluminal (brain) side of the BBB, including P-glycoprotein (Gottesman et al., 1993; Watanabe, 1995), which actively transport various molecules from the brain into the blood stream (Samuels, 1993). Only small (<500 Daltons) and hydrophobic (Pardridge, 1995) molecules can more readily cross the BBB. Thus, the ability of the antibody or fragment thereof as described above to specifically bind the surface receptor, internalize into brain endothelial cells, and undergo transcytosis across the BBB by evading lysosomal degradation is useful in the neurological field.

The present invention also encompasses nucleic acid sequences encoding the molecules as described herein. Given the degeneracy of the genetic code, a number of nucleotide sequences would have the effect of encoding the polypeptide, as would be readily understood by a skilled artisan. The nucleic acid sequence may be codon-optimized for expression in various micro-organisms. The present invention also encompasses vectors comprising the nucleic acids as just described. Furthermore, the invention encompasses cells comprising the nucleic acid and/or vector as described.

The present invention further encompasses the isolated or purified antibody or fragments thereof immobilized onto a surface using various methodologies; for example, and without wishing to be limiting, the antibody or fragment may be linked or coupled to the surface via His-tag coupling, biotin binding, covalent binding, adsorption, and the like. Immobilization of the antibody or fragment thereof of the present invention may be useful in various applications for capturing, purifying or isolating proteins. The solid surface may be any suitable surface, for example, but not limited to the well surface of a microtiter plate, channels of surface plasmon resonance (SPR) sensorchips, membranes, beads (such as magnetic-based or sepharose-based beads or other chromatography resin), glass, plastic, stainless steel, a film, or any other useful surface such as nanoparticles, nanowires and cantilever surfaces.

The invention also encompasses the antibody or fragment thereof as described above linked to a cargo molecule. The cargo molecule may be any suitable molecule, which is delivered across the BBB by the antibody or fragment thereof. The cargo molecule may have a molecular weight in the range of about 1 kD to about 200 kDa; for example, the cargo molecule may have a molecular weight of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kDa, or any weight therebetween, or any range of weights defined by any two aforementioned weights. In specific, non-limiting examples, the cargo molecule may have a molecular weight of 1 kDa (for example, but not limited to a small molecule such as Cy5.5), 1-10 kDa (for example, but not limited to a peptide such as galanin, 3 kDa), about 80 kDa (for example, but not limited to a Fc fragment, enzyme, protein, antibody etc), or about 200 kDa (for example, but not limited to a monoclonal antibody).

For example, and without wishing to be limiting in any manner, the cargo molecule may be a detectable agent, a therapeutic agent, a drug, a peptide, an enzyme, a growth factor, a cytokine, a receptor trap, an antibody or fragment thereof (e.g., IgG, scFv, Fab, $V_HH$, $V_H$, $V_L$, etc) a chemical compound, a carbohydrate moiety, DNA-based molecules (anti-sense oligonucleotide, microRNA, siRNA, plasmid), a cytotoxic agent, viral vector (adeno-, lenti-, retro), one or more liposomes or nanocarriers loaded with any of the previously recited types of cargo molecules, or one or more nanoparticle, nanowire, nanotube, or quantum dots. The cargo molecule as described above may be a detectable agent. For example, the IGF1R-specific antibody or fragment thereof may be linked to a radioisotope, a paramagnetic label, a fluorophore, a fluorescent agent, Near Infra-Red (NIR; for example Cy5.5) fluorochrome or dye, an echogenic microbubble, an affinity label, a detectable protein-based molecule, nucleotide, quantum dot, nanoparticle, nanowire, or nanotube or any other suitable agent that may be detected by imaging methods. The antibody or fragment thereof may be linked to the cargo molecule using any method known in the art (recombinant technology, chemical conjugation, etc.).

The cargo molecule as described herein may be linked, also referred to herein as "conjugated", to the antibody or fragment thereof by any suitable method known in the art. For example, and without wishing to be limiting, the cargo molecule may be linked to the peptide by a covalent bond or ionic interaction. The linkage may be achieved through a chemical cross-linking reaction, or through fusion using recombinant DNA methodology combined with any peptide expression system, such as bacteria, yeast or mammalian cell-based systems. When conjugating the cargo molecule to the antibody or fragment thereof, a suitable linker may be used. Methods for linking an antibody or fragment thereof to a cargo molecule such as a therapeutic or detectable agent would be well-known to a person of skill in the art.

In one non-limiting example, the cargo molecule may be a detectable label, a radioisotope, a paramagnetic label such as gadolinium or iron oxide, a fluorophore, Near Infra-Red (NIR) fluorochrome or dye, an echogenic microbubble, an affinity label (for example biotin, avidin, etc), enzymes, or any other suitable agent that may be detected by diagnostic imaging methods. In a specific, non-limiting example, the anti-IGF1R-4 or fragment thereof may be linked to a near infrared fluorescence (NIRF) imaging dye, for example and not wishing to be limiting Cy5.5, Alexa680, Dylight680, or Dylight800.

Thus, the present invention further provides an in vitro method of detecting IGF1R, comprising contacting a tissue sample with one or more than one isolated or purified antibody or fragment thereof of the present invention linked to a detectable agent. The IGF1R-antibody complex can then be detected using detection and/or imaging technologies known in the art. The tissue sample in the method as just described may be any suitable tissue sample, for example but not limited to a serum sample, a vascular tissue sample, a tumour tissue sample, or a brain tissue sample; the tissue sample may be from a human or animal subject. The step of contacting is done under suitable conditions, known to those skilled in the art, for formation of a complex between the antibody or fragment thereof and IGF1R. The step of detecting may be accomplished by any suitable method known in the art, for example, but not limited to optical imaging, immunohistochemistry, molecular diagnostic imaging, ELISA, imaging mass spectrometry, or other suitable method. For example, and without wishing to be limiting in any manner, the isolated or purified antibody or fragment thereof linked to a detectable agent may be used in immunoassays (IA) including, but not limited to enzyme IA (EIA), ELISA, "rapid antigen capture", "rapid chromatographic IA", and "rapid EIA". (For example, see Planche et al, 2008; Sloan et al, 2008; Rüssmann et al, 2007; Musher et al, 2007; Turgeon et al, 2003; Fenner et al, 2008).

The present invention also provides an in vivo method of detecting IGF1R expression in a subject. The method comprises administering one or more than one isolated or purified antibody or fragment thereof as described herein linked to a detectable agent to the subject, then detecting the labelled antibody or fragment thereof bound to IGF1R. The step of detecting may comprise any suitable method known in the art, for example, but not limited to PET, SPECT, or fluorescence imaging, or any other suitable method. The method as just described may be useful in detecting the expression of IGF1R in blood vessels or tissues, for example but not limited to tumor tissues.

The in vivo detection step in the methods described above may be whole body imaging for diagnostic purposes or local imaging at specific sites, such as but not limited to brain vessels or brain tumor vessels, in a quantitative manner to assess the progression of disease or host response to a treatment regimen. The detection step in the methods as described above may be immunohistochemistry, or a non-invasive (molecular) diagnostic imaging technology including, but not limited to:

Optical imaging;
Positron emission tomography (PET), wherein the detectable agent is an isotopes such as $^{11}$C, $^{13}$N, $^{15}$O, $^{18}$F, $^{64}$Cu, $^{62}$Cu, 1$^{24}$I, $^{76}$Br, $^{82}$Rb and $^{68}$Ga, with $^{18}$F being the most clinically utilized;
Single photon emission computed tomography (SPECT), wherein the detectable agent is a radiotracer such as $^{99m}$Tc, $^{111}$In, $^{123}$I, $^{201}$Tl, $^{133}$Xe, depending on the specific application;
Magnetic resonance imaging (MRI), wherein the detectable agent may be, for example and not limited to gadolinium, iron oxide nanoparticles and carbon-coated iron-cobalt nanoparticles thereby increasing the sensitivity of MRI for the detection of plaques.
Contrast-Enhanced Ultrasonography (CEUS) or ultrasound, wherein the detectable agent is at least one acoustically active and gas-filled microbubble. Ultrasound is a widespread technology for the screening and early detection of human diseases. It is less expensive than MRI or scintigraphy and safer than molecular imaging modalities such as radionuclide imaging because it does not involve radiation.

The present invention further provides a method of transporting a molecule of interest across the blood-brain barrier. The method comprises administering the molecule linked to an antibody or fragment thereof as described herein to a subject; the antibody or fragment thereof transmigrates the blood-brain barrier. The molecule may be any desired molecule, including the cargo molecules as previously described; the molecule may be "linked" to the antibody or fragment thereof using any suitable method, including, but not limited to conjugation or expression in a fusion protein. The administration may be by any suitable method, for example parenteral administration, including but not limited to intravenous (iv), subcutaneous (sc), and intramuscular (im) administration. In this method, the antibody or fragment thereof of the present invention 'ferries' the molecule of interest across the BBB to its brain target.

The present invention also encompasses a composition comprising one or more than one isolated or purified antibody or fragment thereof as described herein. The composition may comprise a single antibody or fragment as described above, or may be a mixture of antibodies or fragments. Furthermore, in a composition comprising a mixture of antibodies or fragments of the present invention, the antibodies may have the same specificity, or may differ in their specificities; for example, and without wishing to be limiting in any manner, the composition may comprise antibodies or fragments thereof specific to IGF1R (same or different epitope).

The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but limited to lyophilised or encapsulated), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the antibody or fragment thereof. Dry powders may also include additives to improve stability and/or carriers to increase bulk/volume; for example, and without wishing to be limiting, the dry powder composition may comprise sucrose or trehalose. In a specific, non-limiting example, the composition may be so formulated as to deliver the antibody or fragment thereof to the gastrointestinal tract of the subject. Thus, the composition may comprise encapsulation, time-release, or other suitable technologies for delivery of the antibody or fragment thereof. It would be within the competency of a person of skill in the art to prepare suitable compositions comprising the present compounds.

The invention also encompasses a method of quantifying an amount of a cargo molecule delivered across the BBB of a subject, wherein the cargo molecule is linked to one or more than one isolated or purified antibody or fragment thereof as described herein, the method comprising
  a) collecting cerebrospinal fluid (CSF) from the subject; and
  b) using targeted proteomics methods to quantify the amount of the cargo molecule linked to one or more than one antibody or fragment thereof in the CSF.

The cargo molecule may be any desired molecule, including the cargo molecules, as previously described; the isolated or purified antibody or fragment thereof transmigrates the blood-brain barrier; and the molecule may be "linked" to the antibody or fragment thereof using any suitable method, including, but not limited to conjugation or expression in a fusion protein, as previously described. In the above method, the CSF is collected from a subject using any suitable method known in the art. The amount of CSF required for targeted proteomics method in step b) may be between about 1 to 10 µl; for example, the amount of CSF required may be about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10 µl, or any amount therebetween, or any range defined by the amount just described. The antibody or fragment linked to the cargo molecule may have been administered to the subject prior to collection of the CSF. A suitable delay between administration and delivery of the antibody or fragment linked to the cargo molecule across the BBB may be required. The delay may be at least 30 minutes following administration of the antibody or fragment linked to the cargo molecule; for example and without wishing to be limiting in any manner, the delay may be at least 30 minutes, 1 hour, 1.5 hour, 2 hours, 2.5 hours, 3 hours, 3.5 hours, 4 hours, 4.5 hours, or 5 hours. The targeted proteomics methods used to quantify the amount of the one or more than one antibody or fragment thereof linked to the cargo molecule may be any suitable method known in the art. For example and without wishing to be limiting, the targeted proteomics method may be a mass spectrometry method, such as but not limited to multiple reaction monitoring using an isotopically labeled internal standard (MRM-ILIS; see for example Haqqani et al., 2013). MRM is advantageous in that it allows for rapid, sensitive, and specific quantification of unlabelled targeted analytes (for example, an antibody or fragment thereof as described herein) in a biological sample. The multiplexing capability of the assay may allow for quantification of both the antibody or fragment thereof and the cargo molecule.

The present invention will be further illustrated in the following examples. However, it is to be understood that these examples are for illustrative purposes only and should not be used to limit the scope of the present invention in any manner.

Example 1: Purification of IGF1R Recombinant Fragment

A 933 amino acid long recombinant fragment of the extracellular domain of IGF1R (shown by the grey box in FIG. 1; see also amino acids 1-933 of SEQ ID NO:12) was prepared. The fragment comprised an N-terminal 30 amino acid signal peptide, the full alpha subunit, a furin cleavage site (RKRR, SEQ ID NO:13; separating alpha and beta subunits), as well as the majority of the extracellular portion of the beta subunit (FIGS. 1 and 2).

Cloning.

The sequence of the IGF1R ectodomain of interest was amplified by PCR using the following primers:

(forward; SEQ ID NO: 14)
5'-CGGGATCCGCCACCATGAAGTCTGGCTCCGGAG-3'

(reverse; SEQ ID NO: 15)
5'-GCTCTAGATCAGAAGTTTTCATATCCTGTTTTGG-3' and subcloned into the SmaI site of Puc19. The IGF1R$^{933}$ sequence was then sub-cloned into pCDN4/myc-His (Invitrogen) to generate pIGF1R$^{933}$-His, which allows for expression of a His-tagged ectodomain as described previously (Samani et al. 2004).

Transient Transfection.

Lentivirus particles expressing IGF1R$^{933}$-His were generated in the packaging cell line 293SF-PacLV, as detailed previously (Broussau et al., 2008). Briefly, the cells were transfected with the vector using polyethylenimine. Fresh medium (LC-SFM), containing 1 µg/ml doxycycline and 10 µg/ml cumate, was added to the cells 5 hours post-transfection and the supernatants containing LV particles were collected after 48-72 hours, concentrated by ultracentrifugation at 100,000×g for 2 h at 4° C. on a 20% sucrose cushion (Gaillet B et al. 2007), re-suspended in LC-SFM medium supplemented with 1% FBS and stored at −70° C. until used.

Stable Expression.

A stable cell line, 293SF-cum2-CR5-IGF1R-His, was generated by transduction of 293SF-Cum2 cell lines with the respective lentivirus particles using a protocol described previously (Gaillet B. et al. 2010). Briefly, 0.5-1.0×10$^5$ 293 SF-Cum2 cells were seeded in 24 wells plates into 200 µl of LC-SFM medium without dextran sulfate. The LV suspension was prepared by mixing 200-500 µL of LV with 8 µg/mL of polybrene and incubating it for 30 min at 37° C. The freshly made LV suspension was added to the cells 4 hours after seeding. After 24 h, 500 µL medium supplemented with dextran sulfate was added to the cells. To increase the level of expression the cells were re-transduced up to 6 times using the same protocol after 3-4 days of cell recovery. Finally the cells were expanded in 6-well plates and shaker flasks.

Large Scale Protein Production and Purification.

The clone identified as the highest producer was expanded in shaker or spinner flasks. Protein production was initiated by the addition of 1 µg/ml cumate in fresh medium, followed by a 24 h incubation at 37° C. and a 4-8 day incubation at 30° C. Cells were removed by centrifugation and the supernatants filtered and concentrated (10×) using the Tangential Flow Filtration Systems (Pellicon ultrafiltration cassettes, EMD Millipore).

The IGF1R$^{933}$-His was purified using a HisPrep column (GE Healthcare) according to the manufacturer's instructions. Briefly, the concentrated sample was applied to a His-prep FF (16/10) column (GE Healtcare), equilibrated and washed with 50 mM sodium phosphate, 300 mM NaCl, 5 mM imidazole pH 7.5 and eluted with the 50 mM sodium phosphate, 300 mM NaCl, 500 mM imidazole pH 7.5. A step elution with 0.1 M sodium citrate pH 4.5 to pH 2.5 was used to elute the protein and peak fractions were pooled. Buffer exchange was performed by ultrafiltration using a 50 kDa cut-off membrane or a desalting column with a buffer containing 50 mM sodium phosphate, 150 mM NaCl and 0.01% Tween-80, pH 7.2. Purity of both proteins was verified by SDS-PAGE and they were stored at −80° C. until used (see subsequent examples).

Example 2: Llama Immunization and Serum Response

To isolate V$_H$Hs that targets the extracellular domain of IGF1R, a llama was immunized with the recombinant IGF1R$^{933}$-His fragment obtained in Example 1.

One male llama (*Lama glama*) was immunized by subcutaneous, lower-back injection of IGF1R$^{933}$-His recombinant antigen (Example 1). On day 1, 200 µg of antigen diluted in PBS to 1 ml was injected together with 1 ml of Freund's Complete Adjuvant (Sigma, St. Louis, Mo.). Three further injections of 100 µg of IGF1R$^{933}$-His antigen plus Freund's Incomplete Adjuvant (Sigma) were performed on days 22, 36, and 50. A final injection of 100 µg of antigen with no adjuvant was performed on day 77. Pre-immune blood was drawn before the first injection on day 1 and served as a negative control. Blood (10-15 ml) was collected on days 29, 43, 57 and 84. The blood from day 84 was processed immediately to isolate peripheral blood mononuclear cells (PBMC). The blood was diluted 1:1 with phosphate buffered saline (PBS) and PBMCs were purified from the blood using the Lymphoprep Tube (Axis Shield). The cells were counted and stored as aliquots of about 1×10$^7$ cells at −80° C. for future use.

Pre-immune and post-immune total serum was analyzed for a specific response to IGF1R933-His antigen by ELISA on day 57. Llama sera from day 84 were fractionated as previously described (Doyle et al, 2008). The resulting fractions, A1 (HCAb), A2 (HCAb), G1 (HCAb) and G2 (cIgG) were analyzed for specific binding to the IGF1R$^{933}$-His antigen by ELISA. Briefly, 5 µg of IGF1R$^{933}$-His recombinant antigen diluted in PBS was incubated overnight (100 µl/well, 18 h, 4° C.) in 96 well Maxisorp plates (Nalgene, Nunc) to coat the plates. Plates were blocked with bovine serum albumin (BSA), washed with PBS-T (PBS+ 0.05% (v/v) Tween-20), and serial dilutions of pre-immune total serum, post-immune total serum (day 57), and fractionated serum (day 84) were applied. After incubation at room temperature for 1.5 h the plates were washed with PBS-T, before goat anti-llama IgG (1:1,000 in PBS) was added and plates were incubated for 1 h at 37° C. After washing with PBS-T, pig anti-goat IgG-HRP conjugate (1:3,000 in PBS) was added and plates were incubated for 1 h at 37° C. A final PBS-T wash was carried out prior to the addition of 100 µl/well TMB substrate (KPL, Gaithersburg, Md.); the substrate was incubated for 10 min. The reaction was stopped with 100 µl/well 1 M $H_3PO_4$. Absorbance was read at 450 nm.

Example 3: Library Construction and Selection of IGF1R-Binding $V_HH$s

A hyperimmunized llama $V_HH$ library was constructed based on RNA isolated from the PBMCs in Example 2.

Library construction and panning was performed essentially as previously described (Arbabi-Ghahroudi et al, 2009a, 2009b; Tanha et al, 2003). Total RNA was isolated from approximately $10^7$ PBMCs collected on day 84 post-immunization (Example 2) using the QIAamp RNA Blood Mini Kit (Qiagen). About 5 µg of total RNA was used as template for first strand cDNA synthesis with oligo dT primers using the First-Strand cDNA Synthesis Kit (GE Healthcare). The cDNA was amplified by an equimolar mix of three variable region-specific sense primers:

```
MJ1:
                                          (SEQ ID NO: 16)
5'-GCCCAGCCGGCCATGGCCSMKGTGCAGCTGGTGGAKTCTGGGGGA-
3'

MJ2:
                                          (SEQ ID NO: 17)
5'-GCCCAGCCGGCCATGGCCCAGGTAAAGCTGGAGGAGT0TGGG3GA-
3'

MJ3:
                                          (SEQ ID NO: 18)
5'-GCCCAGCCGGCCATGGCCCAGGCTCAGGTACAGCTGGTGGAGTCT-
3',
``` and two antisense $CH_2$-specific primers:

```
CH2:
                                          (SEQ ID NO: 19)
5'-CGCCATCAAGGTACCAGTTGA-3'

CH2b3:
                                          (SEQ ID NO: 20)
5'-GGGGTACCTGTCATCCACGGACCAGCTGA-3'.
```

Briefly, the PCR reaction mixture was set up in a total volume of 50 µl with the following components: 1-3 µl cDNA, 5 pmol of MJ1-3 primer mixture, 5 pmol of $CH_2$ or $CH_2b_3$ primers, 5 µl of 10× reaction buffer, 1 µl of 10 mM dNTP, 2.5 unit of Taq DNA polymerase (Hoffmann-La Roche). The PCR protocol consisted of an (i) initial step at 94° C. for 3 min, (ii) followed by 30 cycles of 94° C. for 1 min, 55° C. for 30 s, 72° C. for 30 s and (iii) a final extension step at 72° C. for 7 min. The amplified PCR products were run on a 2% agarose gel and two major bands were observed: a band of about 850 bp, corresponding to conventional IgG, and a second band of around 600 bp, corresponding to the $V_HH$-CH2 region of camelid heavy chain antibodies. The smaller bands were cut and purified using the QIAquick Gel Extraction Kit (Qiagen) and re-amplified in a second PCR in a total volume of 50 µl using 1 µl (30 ng) of DNA template, 5 pmol of each of MJ7 primer (5'-CATGTGTAGACTCGCG GCCCAGCCGGCCATGGCC-3' SEQ ID NO:21) and MJ8 primer (5-CATGTGTAGAT-TCCTGGCCGGCCTGGCCTGAGGAGACGGTGACCT-GG-3' SEQ ID NO:22), 5 µl of 10× reaction buffer, 1 µl of 10 mM dNTP, 2.5 unit of Taq DNA polymerase. The PCR protocol consisted of (i) an initial step at 94° C. for 3 min, (ii) followed by 30 cycles of 94° C. for 30 s, 57° C. for 30 s and 72° C. for 1 min and (iii) a final extension step at 72° C. for 7 min. The amplified PCR products, ranging between 340 bp and 420 bp and corresponding to $V_HH$ fragments of heavy chain antibodies, were purified using the QIAquick PCR Purification Kit (Qiagen), digested with SfiI restriction enzyme (New England BioLabs) and re-purified using the same kit.

80 µg of pMED1 phagemid vector (Arbabi-Ghahroudi et al, 2009b) were digested with SfiI overnight at 50° C. To minimize self-ligation, 20 units of XhoI and PstI restriction enzymes were added to cut the excised fragment and the digestion reaction was incubated for an additional 2 h at 37° C. 60 µg of digested phagemid DNA was ligated with 6 µg of digested (SfiI for 5 h at 50° C.) $V_HH$ fragments (molar ratio 1:1) for 3 h at room temperature using LigaFast Rapid DNA Ligation System (Promega) according to the manufacturer's instructions. The ligated plasmids were purified using the QIAquick PCR Purification Kit (Qiagen), eluted in a final volume of 100 µl, and transformed into electrocompetent TG1 E. coli (Stratagene) using 5 µl of ligated DNA aliquot per transformation reaction, as described (Arbabi-Ghahroudi et al, 2009b). The size of the library was determined to be $5\times10^7$ as described in (Arbabi-Ghahroudi et al, 2009b). 20 clones were sequenced and contained all unique $V_HH$ sequences. The E. coli, containing the library was grown for 2-3 h at 37° C., 250 rpm in the presence of 2% (w/v) glucose. The bacteria were then pelleted, resuspended in 2×YT/Amp/Glu (2×YT medium with 100 µg/ml ampicillin and 2% (w/v) glucose) with 35% (v/v) glycerol and stored at −80° C. in small aliquots.

Panning experiments were essentially performed as described in (Arbabi et al, 1997). Two milliliters of the library ($2.0\times10^{10}$ bacteria) were thawed on ice and grown in 2×YT/Amp/Glu for about 2 h at 37° C. ($A_{600}$=0.4-0.5). The E. coli were subsequently infected with 20× excess M13KO7 helper phage (New England Biolabs) for 1 h at 37° C. The culture was then centrifuged at 4° C. and infected bacterial pellets were re-suspended in 200 ml of 2×YT/Amp with 50 µg/ml kanamycin and incubated at 37° C. and 250 rpm. The phage particles in the culture supernatant were incubated with ⅕ volume of 20% PEG 8000/2.5M NaCl on ice for 1 h and centrifuged at 10,000 rpm for 15 min. The phage pellets were re-suspended in 1.5 ml of sterile PBS, titrated and used as input phage for panning. For panning round 1, 96-well Maxisorp™ plates were coated with 10 µg of recombinant IGF1R$^{933}$-His per well in 100 µl PBS overnight at 4° C. The wells were rinsed with PBS and blocked with PBS plus 1% (w/v) casein for 2 h at 37° C. Approximately $10^{12}$ phages were added to the blocked wells and incubated for 2 h at 37° C. After 10× washing with PBS/0.1° 70 (v/v) Tween 20, the bound phages were eluted with 0.1 M triethylamine, neutralized (50 µl of 1M Tris-HCl, pH 7.4) and mixed with exponentially growing TG1 E. coli. Titration of eluted phage was performed and infected bacteria were superinfected with M13K07 and grown overnight at 37° C. The purified phage from the overnight culture was used as the input for the next round of panning. The panning was continued for three further rounds. The same protocol as described above was used, except that the amount of recombinant antigen used to coat the plates was reduced to 7 µg, 5 µg and 5 µg for the second, third and fourth rounds of panning, respectively.

Individual TG1 colonies obtained after round four of panning were subjected to phage ELISA screening, essentially as described elsewhere (Doyle et al, 2008), with the exception that 5 µg/ml of IGF1R$^{933}$-His recombinant antigen were used to coat the microtiter plates. All positive clones were sent for DNA sequencing. Unique clones that gave high phage ELISA signals were selected for large-scale expression and purification using known methods (see Example 4). A clone dubbed IGF1R-4 was identified for further study; its sequence is shown below.

(SEQ ID NO: 5)
QVKLEESGGGLVQAGGSLRLSCEVSGGTVSPTAMGWFRQAPGKEREFVGH
ITWSRGTTRVASSVKDRFTISRDSAKNTVYLQMNSLKSEDTAVYYCAAST
FLRILPEESAYTYWGQGTQVTVSS

Example 4: Humanization of IGF1R-4

To avoid potential immunogenicity of llama-derived IGF1R-4 when applied as BBB carrier for therapeutics, to the camelid-derived sdAb was "humanized" by mutation of "camelid" residues in the V$_H$H. It should be noted that, for the purpose of humanization, Kabat numbering (Kabat et al, 1991) was used for identification of CDR residues.

3D-Structure Modeling of Camelid V$_H$Hs.

Template structures similar to IGF1R-4 V$_H$H were identified using BLAST searches against the Protein Data Bank (PDB). The 3D structure of the IGF1R-4 was approximated using homology modeling based on 4KRP|B (PDB code|Chain ID) as the main template, with additional information from 4FHB|D. The IGF1R-4 V$_H$H structure was then built by mutating the main template structure to the IGF1R-4 sequence; this included 35 mutations at various positions. The IGF1R-4 V$_H$H model was then refined by energy minimization with the AMBER force-field and a stepwise release of constraints, ranging from the CDR loops, which were relaxed first, to the backbone heavy atoms of the framework region, which were fully relaxed only in the last stage. The CDR-H3 loop of the V$_H$H model was then refined by Monte-Carlo-minimization (MCM) conformational sampling, in which dihedral angles in the CDR-H3 region were sampled followed by energy minimization.

Selection of the Human Heavy-Chain Framework for the Camelid CDR.

Human heavy-chain framework was selected by standard sequence homology comparison against the human germline databases (VBASE), against other sequence databases (Genbank and SwissProt), and against the human framework consensus sequences. BLAST searches were conducted to retrieve sequence matches with highest homology in the framework region only (i.e., excluding CDR) while matching the length of the CDR. The closest human frameworks identified for IGF1R-4 V$_H$H corresponded to the human VH-3 subgroup. Several human germline VH-3 framework sequences that were most similar to IGF1R-4 V$_H$H were also retained in addition to the human VH-3 consensus sequence. The IGF1R-4 V$_H$H framework sequences required 18 mutations in order to arrive at the consensus human VH-3 sequence for 100% framework humanization.

Identification of Framework Residues for Back-Mutations.

The IGF1R-4 V$_H$H model and its fully-humanized counterpart were characterized to estimate the humanness index, antigen contact propensity index, to delineate the CDR, canonical residues, unusual framework residues, potential glycosylation sites, buried residues, Vernier zone residues, and proximity to CDR. The analysis of these data suggested the design of several humanized variants for the anti-IGF1R V$_H$H, each variant having varying numbers of back-mutations to the parent camelid residues at various positions. 6 humanized variants were designed for IGF1R-4 V$_H$H (IGF1R-4_H1 to IGF1R-4_H6), where variants contained up to 10 back-mutations. Some of these camelid back-mutations residues were buried inside the V$_H$H domain core and hence are not expected to induce an immune response.

Example 5: Expression and Purification of Selected V$_H$H Constructs

IGF1R-4 identified in Example 3 and the humanized versions constructed in Example 4 (collectively referred to herein as "V$_H$H constructs") were sub-cloned into expression plasmids for protein expression and purification.

A phagemid vector containing the DNA of the V$_H$H IGF1R-4 clone was purified using the MiniPrep Kit (Qiagen). The IGF1R-binding V$_H$H IGF1R-4 was PCR amplified from the pMED1 phagemid vector, adding an N-terminal BbsI cleavage site and a BamHI cleavage site at the C-terminus, using primers:

(forward; SEQ ID NO: 23)
5'-TATGAAGACACCAGGCCCAGGTAAAGCTGGAGGAGTCT-3

(reverse; SEQ ID NO: 24)
5'-TTGTTCGGATCCTGAGGAGACGGTGACCTG-3'

The PCR fragment and the pSJF2H expression vector was digested with BbsI and BamHI restriction enzymes (NEB) according to the manufacturer's instructions. Following digestion, each digested IGF1R-4 V$_H$H fragment was ligated into the digested pSJF2H expression vector, using methods similar to those described in Arbabi-Ghahroudi et al. (2009b); the ligation products were then transformed into electro-competent TG1 E. coli. Clones were selected on LB agar plates+100 µg/ml ampicillin and verified by DNA sequencing.

The humanized clones were synthesized and directly cloned into pSJF2H, similarly as described above and subsequently transformed into E. coli TG1 and selected as described above.

Protein Expression.

All IGF1R-4 V$_H$H constructs were expressed in TG1 E. coli. An overnight culture in LB/amp/glu medium (LB medium supplemented with 100 µg/ml ampicillin and 1% glucose) was subcultured at 1:100 dilution in 1 L LB/amp/glu. Protein expression was induced at an OD$_{600}$ of 0.8-0.9 by the addition of IPTG to a final concentration of 0.2 mM. The culture was grown at 220 rpm overnight at 37° C. The bacteria were pelleted by centrifuging at 6000 rpm for 12 min; the pellet was re-suspended in 35 ml of cold TES buffer (0.2M Tris-Cl pH 8.0, 20% sucrose, 0.5 mM EDTA). The suspension was incubated on ice and vortexed every 10 min for 1 hour. Then 45 ml of cold TES (⅛ volume of total volume) was added and immediately vortexed for 1 minute and for 15 seconds every 10 min thereafter for 1 hour to extract the protein from the periplasm. The resulting supernatant containing V$_H$H was filtered through a 0.22 µm membrane and dialysed overnight into immobilized metal-affinity chromatography (IMAC) buffer A (10 mM HEPES pH 7.0, 500 mM NaCl). The protein was purified using HiTrap Chelating HP columns (GE Healthcare) as described previously (Arbabi-Ghahroudi 2009b). Eluted protein fractions were analyzed by SDS-PAGE and Western blotting before being dialysed against PBS as described previously (Arbabi-Ghahroudi 2009b). The purified protein fractions were pooled and dialyzed against PBS+3 mM EDTA, and the protein concentration was determined.

Example 6: Biophysical Characterization of Anti-IGF1R $V_HH$ IGF1R-4

The anti-IGF1R $V_HH$ IGF1R-4 constructs expressed and purified in Example 4 were characterized using size exclusion chromatography, melting temperature analysis, and surface plasmon resonance.

Size Exclusion Chromatography:

Size exclusion chromatography employing Superdex™ 75 (GE Healthcare) was used to eliminate any possible aggregates prior to Surface Plasmon Resonance (SPR) analysis. The running buffer used was 10 mM HEPES, pH7.4 containing 150 mM NaCl, 3 mM EDTA and 0.005% P20. Concentrations of fractions used for SPR analysis were determined by measuring absorbance at 280 nm wavelength. The SEC analysis suggested that all IGF1R-4 $V_HH$ constructs, except H1 were monomeric, based on the elution volume compared to standards (FIG. 3A). IGF1R-4 H1 was therefore excluded from further evaluation.

Melting Temperature:

The thermal stability of the IGF1R-4 $V_HH$ and humanized constructs was evaluated using melting temperature ($T_m$) measurement by CD spectroscopy. A Jasco J-815 spectropolarimeter equipped with a Peltier thermoelectric type temperature control system (Jasco, Easton, Md., USA) was used to carry out experiments. A CD cuvette with a path length of 1 mm was used. The spectra were recorded over a wavelength range of 180-260 nm with scanning speed of 50 nm/min, digital integration time (DIT) of 4 s, a band width of 1 nm, data pitch of 1 nm, and an integration time of 1 s. To measure melting temperature or $T_m$ (Greenfield, 2006a; 2006b), CD spectra were recorded over a temperature range of 30° C. to 96° C. All CD spectra were subtracted from the blank corresponding to buffer spectra. Measurements were performed with concentrations of 50 µg/mL $V_HH$ in 100 mM sodium phosphate buffer, pH 7.4. Heat-induced protein denaturation was monitored at 210 nm for all variants. The fraction folded (ff) was obtained by a formula as described (Greenfield, 2006a; 2006b):

$$ff=([\theta]_T-[\theta]_U)/([\theta]_F-[\theta]_U)$$ formula I where $[\theta]_T$ is the molar ellipticity at any temperature, $[\theta]_F$, is the molar ellipticity of the fully folded protein at 30° C. and $[\theta]_U$ is the molar ellipticity of the unfolded protein at 90° C. Melting temperature ($T_m$) was obtained as a midpoint of the unfolding curve (fraction folded (ff) versus temperature) by a nonlinear regression curve fit (Boltzman sigmoidal equation) using the graphing software GraphPad Prism (version 4.02 for Windows). The melting temperatures ($T_m$) of $V_HH$ were determined based on ellipticity data assuming a two-state system, which is in agreement with the observed denaturation curves corresponding to a sharp transition into denaturation. The $T_m$ values were taken at midpoint of the sigmoidal denaturation curves of fraction folded (ff) versus temperature.

Figure 3B:
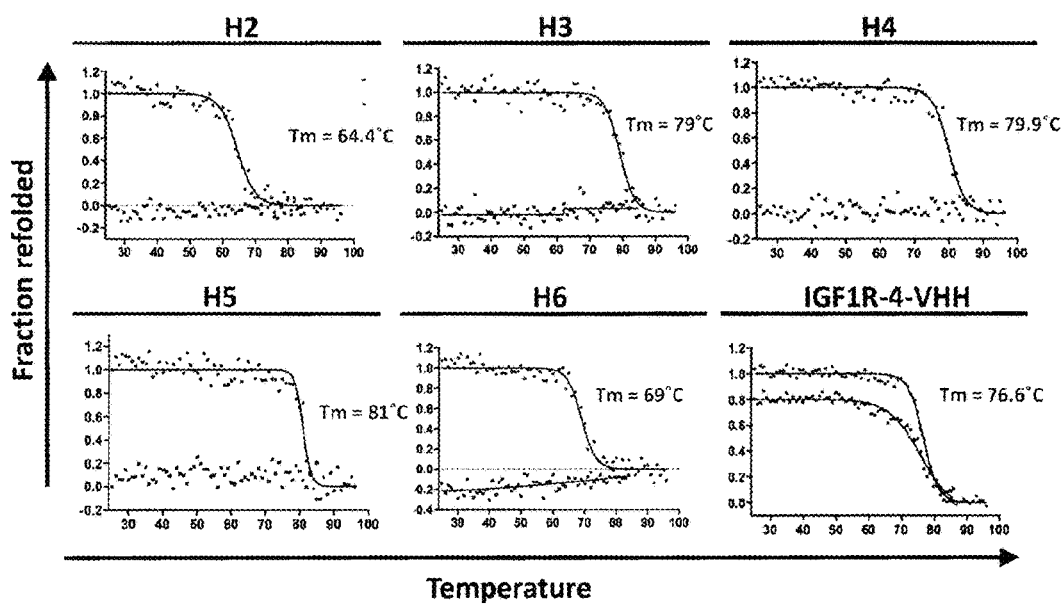
FIG. 3B shows the melting temperature ($T_m$) as determined by circular dichroism (CD) for IGF1R-4 $V_HH$ and its humanized variants (H2, H3, H4, H5, H6). The proteins were heated to above 90° C. and measurements were taken in the CD instrument to determine the melting curve (top curve) and the $T_m$. Subsequently, the proteins were cooled to room temperature, heated once more and analysed by CD (bottom curve for IGF1R-4 VHH; line or dots around 0% refolded for humanized variants). This allowed the determination of the fraction of refolded protein, which was zero for humanized versions and 80% for IGF1R-4.

Results are shown in FIG. 3B. The melting temperatures of humanized $V_HH$ H3, H4, and H5 were improved (higher) in comparison to the IGF1R-4 $V_HH$, suggesting improved biophysical properties. Humanized constructs H2 and H6 had poorer melting temperatures compared to IGF1R-4 $V_HH$. In contrast to IGF1R-4 $V_HH$, none of the humanized $V_HH$s refolded after heat exposure.

Figure 3C:
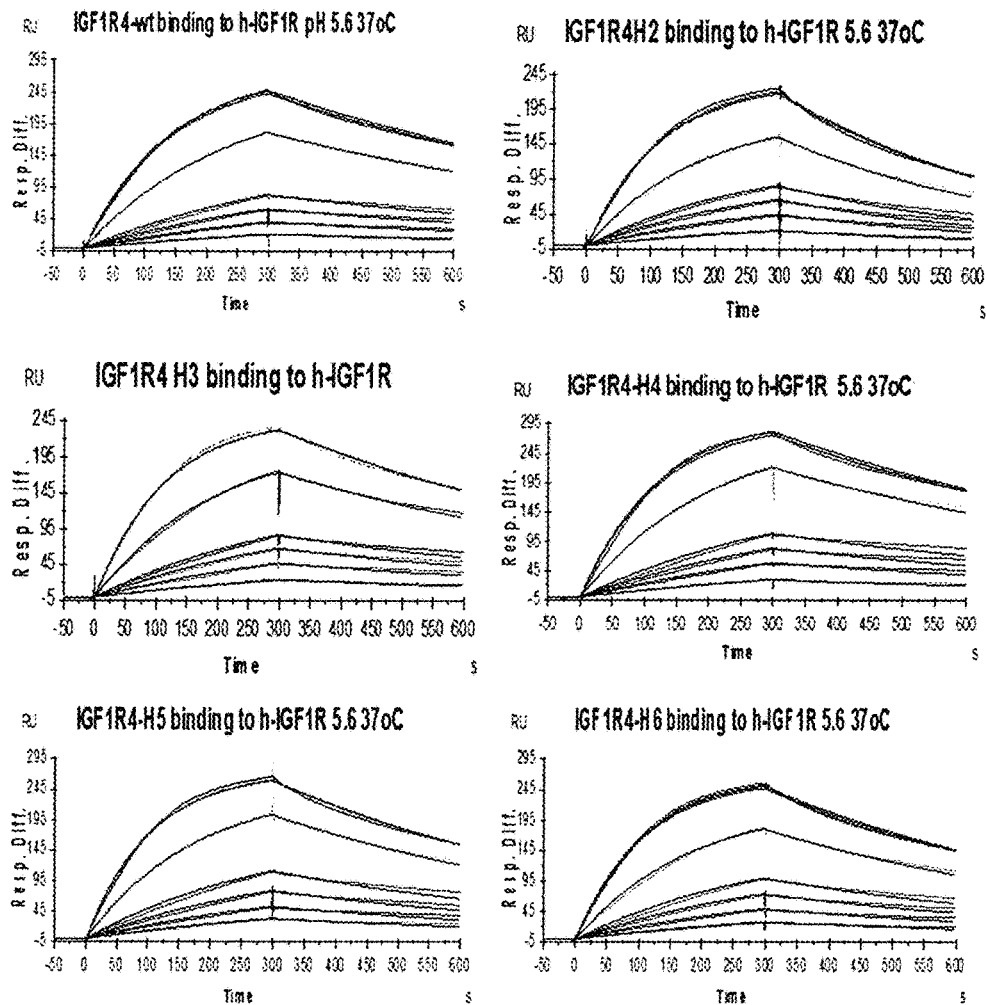
FIG. 3C shows a surface plasmon resonance (SPR) sensogram overlay for binding of 0.1-5 nM IGF1R-4 $V_HH$ and its humanized variants (H2, H3, H4, H5, H6) to the recombinant extracellular portion of the human IGF1R fragment. The data fit well to a 1:1 model.

Surface Plasmon Resonance (SPR):

The binding of monomeric IGF1R-4 $V_HH$ constructs to immobilized recombinant human IGF1R (Example 1) was determined by SPR using BIACORE 3000 (GE Healthcare). Approximately 3000 Resonance Units (RU) of recombinant human IGF1R were immobilized on a Sensor chip CM5. Immobilization was carried out at a concentration of 10 µg/ml in 10 mM acetate at pH4.0 using the amine coupling kit supplied by the manufacturer. The remaining binding sites were blocked with 1 M ethanolamine pH 8.5. An ethanolamine blocked surface was used as a reference surface. For the binding studies, analyses were carried out at 25° C. in 10 mM HEPES, pH7.4 containing 150 mM NaCl, 3 mM EDTA and 0.005% surfactant P20 (Polyoxyethylenesorbitan; GE Healthcare). Various concentrations of the IGF1R-4 $V_HH$ were injected over the immobilized human IGF1R and reference surfaces at a flow rate of 20 µl/min. Surfaces were regenerated with 10 mM glycine pH 2.0 with a contact time of 24 seconds. Data were analyzed with BIAevaluation 4.1 software (GE Healthcare). The sensograms in FIG. 3C show that the data fit well to a 1:1 model, giving $K_D$ and 'off-rates' shown Table 1. This indicates that the IGF1R-4 and the humanized variants are high-affinity single-domain antibodies binding to the extracellular domain of human IGF1R.

TABLE 1

Affinity of IGF1R-4 constructs for human IGF1R as determined by surface plasmon resonance.

|  | $K_D$ (nM) | $k_d$ (s$^{-1}$) |
| --- | --- | --- |
| IGF1R-4 | 0.32 | 2.9 × 10$^{-4}$ |
| IGF1R-4 H2 | 1.07 | 6.1 × 10$^{-4}$ |
| IGF1R-4 H3 | 0.39 | 3.4 × 10$^{-4}$ |
| IGF1R-4 H4 | 0.45 | 3.9 × 10$^{-4}$ |
| IGF1R-4 H5 | 0.52 | 4.6 × 10$^{-4}$ |
| IGF1R-4 H6 | 0.52 | 3.8 × 10$^{-4}$ |

Figure 3D:
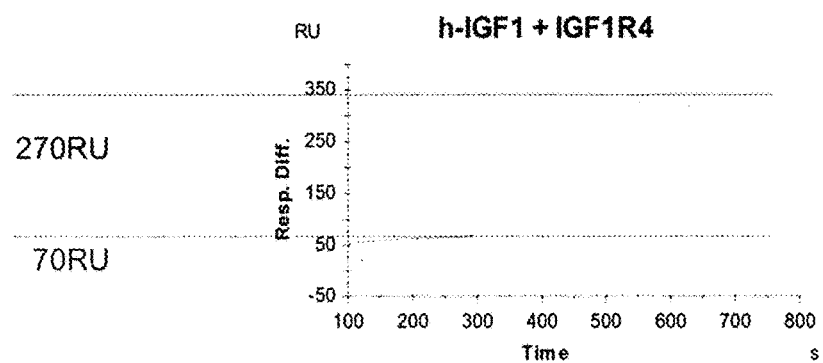
FIG. 3D shows SPR sensograms of IGF1R-4 $V_HH$ binding to the recombinant extracellular portion of the human IGF1R fragment in presence of IGF1. IGF1 in 100-fold excess did not affect IGF1R-4 $V_HH$ binding, showing that both bind to different epitopes on the receptor.

The SPR analyses were further used to demonstrate that IGF1R-4 $V_HH$ does not bind to the same epitope on the receptor as the natural ligand IGF-1 (FIG. 3D). The experiment was set up, carried out and analysed as described above. Binding to freshly immobilized human IGF1R surface was studied by injection of human IGF1 ligand at a concentration of 25×$K_D$ followed by co-injection of IGF1R-4 both at concentrations 25×14), with flow rates of 20 µl/min and injection times of 5 minutes. Surfaces were regenerated by washing with running buffer. The natural ligand IGF-1 bound the receptor with saturation reached at 70RU; the IGF1R-4 $V_HH$ bound to the IGF1R-IGF-1 complex with the expected ~265RU (relative units; binding saturation). The simultaneous binding of both IGF1R-4 $V_HH$ and IGF-1 to the receptor demonstrates that both bind to different epitopes.

Figure 3E:
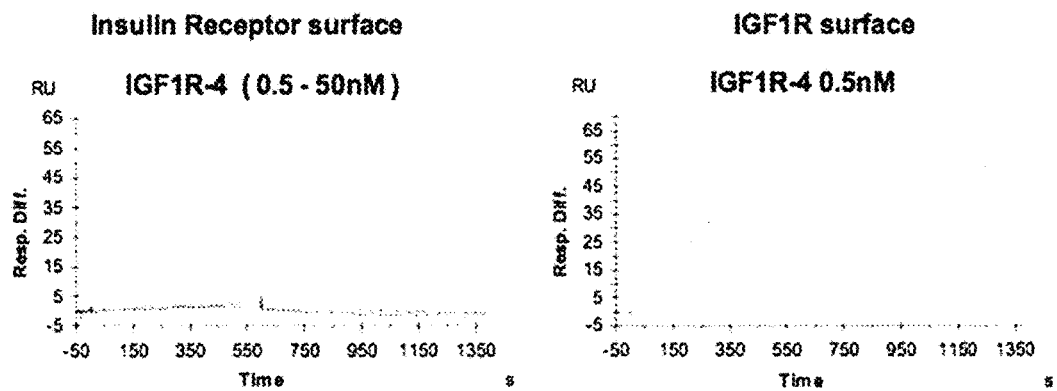
FIG. 3E shows that IGF1R-4 $V_HH$ did not bind to the recombinant extracellular portion of the human Insulin Receptor (IR) immobilized on SPR surface, while it did bind to the control surface of human IGF1R.

The cross-reactivity of IGF1R-4 binding to human Insulin Receptor was also evaluated using SPR. The experiment was set up, carried out and analysed as described above. Briefly, besides human IGF1R, approximately 4000 Resonance Units (RU) of recombinant human Insulin Receptor (R&D systems) was immobilized on a separate cell on a Sensor chip CM5. Subsequently, different concentrations of IGF1R-4 were flowed over the surfaces (0.5-50 nM). While binding to IGF1R could be observed at already 0.5 nM IGF1R-4, no binding to the Insulin Receptor surface was observed even at 50 nM (FIG. 3E), suggesting that IGF1R-5 cannot bind the Insulin receptor.

Example 7: Internalization of the IGF1R-4 by Brain Endothelial Cells

To determine whether IGF1R-4 is internalized into cells, svARBEC cells were incubated with Cy5-5-labelled IGF1R-4.

IGF1R-4 V$_H$H was labeled with NHS-Cy5.5. The labeling was done through a stable amine bond between primary amines (at the N-terminus and/or on lysine side chains of the protein) and the NHS ester. Typically, 10% v/v of 1M carbonate/bicarbonate buffer (759 mM bicarbonate, 258 mM carbonate) pH 9.3 was added to 4 mg of V$_H$H prepared in PBS (1.06 mM KH$_2$PO$_4$, 154 mM NaCl, 5.6 mM Na$_2$HPO$_4$) pH7.4 and adjusted to a final concentration of 4 mg/mL. The NHS-Cy5.5, dissolved in DMSO at 10 mg/mL, was added at a 2× molar ratio of dye to protein. The mixture was incubated at room temperature for 2 h with several inversions in a 1.5 mL microcentrifuge tube. Following the incubation, unbound dye and reaction bi-products were filtered using Zeba Spin Desalting Columns, 7K MWCO (Pierce) and measured using a Beckman DU530 spectrophotometer (Beckman Coulter). Cy5.5-labeled IGF1R-4 or FC5 as a positive control (1 mg/ml) were incubated with SV40 immortalized rat brain endothelial cells (svARBEC) at 4° C. (FIG. 4, top panels), thus allowing only for passive, non-specific transport mechanism to occur, or at 37° C. (FIG. 4, bottom panels) to allow for active transport such as receptor mediated endocytosis to take place. Co-staining with wheat germ agglutinin and DAPI was carried out to visualize the cell surface and the nucleus, respectively. Cells were observed under fluorescent microscope and images were captured.

If incubated at 4° C., IGF1R-4 was found outside the cells co-localizing with the cell membrane stained with wheat germ agglutinin. In contrast, when incubated at 37° C., IGF1R-4 accumulated in vesicles inside the cells, likely endosomes, suggesting that the antibody internalized into cells through an active transport mechanism. Similar behaviour was observed for FC5, previously shown to enter the cells by energy-dependent endocytosis via clathrin-coated vesicles (Abulrob et al. 2005)

Example 8: Production of a IGF1R-4-mFc Construct

Constructs comprising IGF1R-4 V$_H$H fused to a murine antibody fragment crystallisable (Fc; mFc2b) was prepared, expressed, and isolated. The sequence of the IGF1R-4-mFc construct is shown in FIG. 5A, with a schematic of the molecule shown in FIG. 5B. The fusion protein also comprised a N-terminal signal peptide (MEFGLSWVFLVAILK-GVQC; SEQ ID NO:37) that is not shown in the sequence of FIG. 5A.

The IGF1R-4 cDNA was cloned into mammalian expression vector pTT5 (Durocher, 2002) containing the mouse Fc2b fragment. Polyplexes of the resulting vector were pre-formed by mixing 25 ml of plasmid DNA solution containing 187.5 µg pTT5-IR5mFc2b, 56.25 µg pTT-AK-Tdd (activated mutant of Protein Kinase B), 18.75 µg pTTo-GFP (to monitor transfection efficiency), and 112.5 µg of salmon testis DNA (Sigma-Aldrich); and 25 ml of PEI solution containing 1.125 mg of PEIpro™ (PolyPlus Transfection), both made in F17 medium. The mixture was incubated for 10 minutes prior to addition to the cell culture. A 450 ml culture of CHO cells stably expressing a truncated EBNA1 protein (CHO-3E7) and grown in F17 medium (Invitrogen) was transfected with 50 ml of polyplexes. Twenty four hours post-transfection, the culture was fed with 12.5 ml of 40% (w/v) tryptone N1 (Organotechnie) solution and 1.25 ml of 200 mM valproic acid solution. The culture was harvested 8 days post-transfection and clarified by centrifugation. Clarified medium was filtered through a 0.22 µm membrane prior to its application on a column packed with 5 ml of protein-A MabSelect SuRe resin (GE Healthcare). After loading, the column was washed with 5 volumes of phosphate-buffered saline pH 7.1 (PBS) and the antibody was eluted with 100 mM sodium citrate buffer pH 3.0. Fractions containing the eluted antibody were pooled and a buffer exchange was performed by loading on a desalting Econo-Pac column (BioRad) equilibrated in PBS. Desalted antibody was then sterile-filtered by passing through a Millex GP (Millipore) filter unit (0.22 µm) and aliquoted.

Figure 6A:
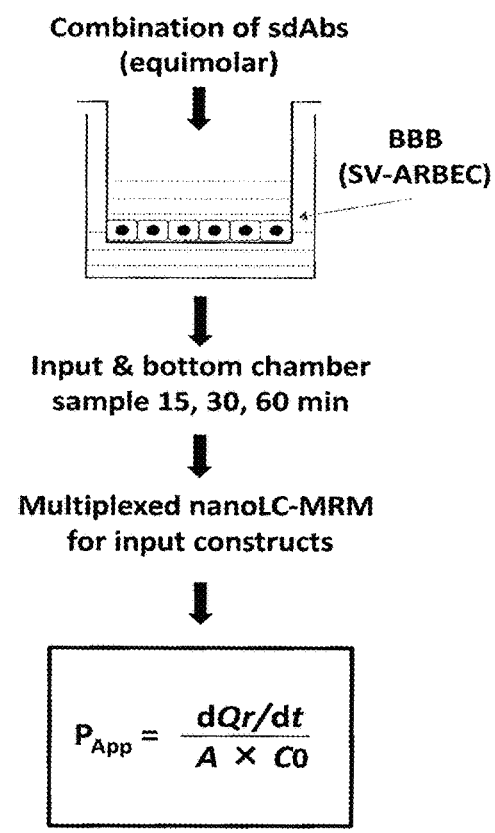
FIG. 6A is a flowchart summarizing the use of the in vitro BBB model to assess the ability of various $V_HH$s to cross the BBB. Equimolar amounts (5.6 µM or 1.25 µM) of positive (FC5) and negative control (A20.1, a *Clostridium difficile* toxin A-binding $V_HH$; and EG2, an EGFR binding $V_HH$) $V_HH$ and IGF1R-4 were tested simultaneously for their ability to cross a rat in vitro BBB model. SV40-immortalized brain endothelial cells from adult rat (svARBECs) are grown in a monolayer on the membrane of an insert in the presence of rat astrocyte-conditioned medium in the bottom chamber and standard medium in the top chamber. Following co-addition of equimolar amounts of the various $V_HH$ to the luminal side of the BBB model, samples were taken from the bottom chamber after 15, 30, and 60 min. The concentrations of each $V_HH$ were then quantified by mass spectrometry (multiple reaction monitoring-isotype labeled internal standards; MRM-ILIS) in these samples. The $P_{app}$ value [Qr/dt=cumulative amount in the receiver compartment versus time; A=area of the cell monolayer; C0=initial concentration of the dosing solution] is commonly used to determine the ability of a molecule to cross the BBB.

Example 9: Transport of the IGF1R-4 Across In Vitro Blood Brain Barrier Model To evaluate whether the IGF1R-4 V$_H$H, its humanized versions (H2 to H6), and IGF1R-4-mFc (Example 8) transmigrate the blood-brain barrier, an in vitro assay was used as described below. A flow chart summarizing the experiment is shown at FIG. 6A.

SV40-immortalized Adult Rat Brain Endothelial Cells (Sv-ARBEC) were used to generate an in vitro blood-brain barrier (BBB) model as described (Garberg et al., 2005; Haqqani et al., 2012). Sv-ARBEC (80,000 cells/membrane) were seeded on a 0.1 mg/mL rat tail collagen type I-coated tissue culture inserts (pore size-1 µm; surface area 0.9 cm$^2$, Falcon) in 1 ml of growth medium. The bottom chamber of the insert assembly contained 2 ml of growth medium supplemented with the immortalized neonatal rat astrocytes-conditioned medium in a 1:1 (v/v) ratio. Equimolar amounts (5.6 µM) of positive (FC5) or negative controls (A20.1, a *Clostridium difficile* toxin A binding V$_H$H; and EG2, an EGFR binding V$_H$H), IGF1R-4 V$_H$H, humanized versions (H2-H6) or IGF1R-4mFc were tested for their ability to cross this rat in vitro BBB model. Following exposure of equimolar amounts of the sdAbs to the luminal side of the BBB, samples were taken after 15, 30, and 60 min from the abluminal side. The sdAb content of each sample was then quantified by mass spectrometry (multiple reaction monitoring-isotype labeled internal standards; MRM-ILIS) as described by Haqqani et al. (2012) (see method description below).

Determination of the Apparent Permeability Coefficient:

Quantified values can be directly plotted or the P$_{app}$ (apparent permeability coefficient) values can be determined with the given formula (FIG. 6A) and plotted. The P$_{app}$ value is commonly used to determine the ability of a molecule to cross the BBB. [Qr/dt=cumulative amount in the receiver compartment versus time; A=area of the cell monolayer; C0=initial concentration of the dosing solution]. P$_{app}$ values are a measure of the specific permeability of the compound across brain endothelial monolayer.

Figure 6B:
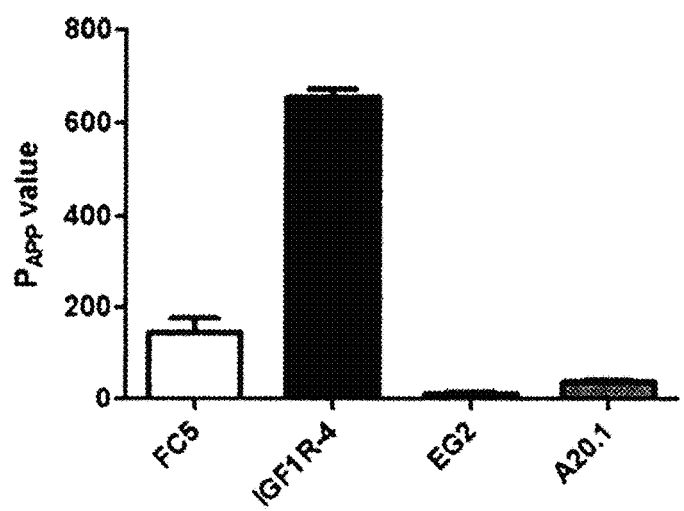
FIG. 6B shows the $P_{app}$ values of the four co-administered $V_HH$s. IGF1R-4 $V_HH$ has a significantly higher $P_{app}$ value than FC5, while both negative controls have low $P_{app}$ values, indicating facilitated transport of FC5 and IGF1R-4 $V_HH$ compared to low non-specific transport or paracellular transport of control $V_HH$s.
Figure 6C:
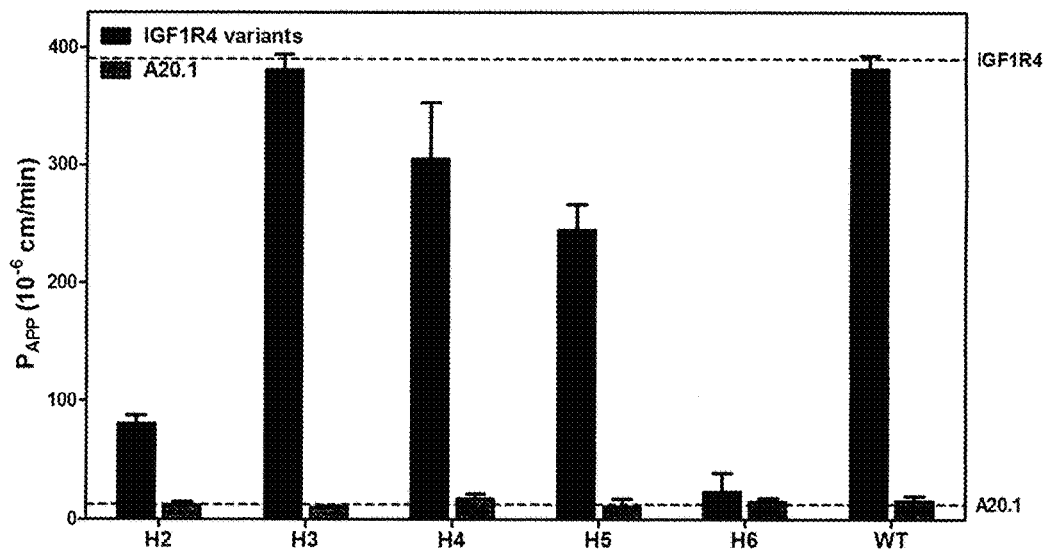
FIG. 6C shows the $P_{app}$ values of the humanized IGF1R-4 single-domain antibodies (H2, H3, H4, H5, H6) (black bars), compared to A20.1 $V_HH$ (grey bars), which was tested as a control in the same well (the average A20.1 value is indicated by a grey dotted line). The result clearly indicates that simply binding of IGF1R (as seen for the humanized 6 variant (H6)) is not sufficient to trigger transmigration of the BBB.
Figure 6D:
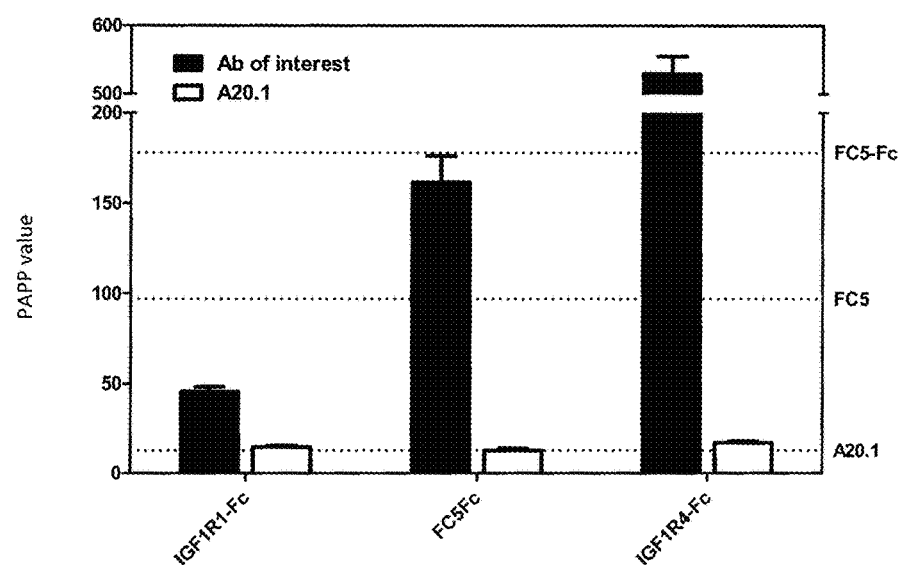
FIG. 6D shows the $P_{app}$ values of the C-terminal fusion of IGF1R-4 $V_HH$ to mouse Fc (black), compared to the A20.1-mouse Fc (A20.1mFc) (grey) which was tested in the same well and has a very low $P_{app}$ value. IGF1R-4-mFc has a significantly higher $P_{app}$ value than FC5-mFc (typically around 180 cm/min, as indicated by the grey dotted line). Another IGF1R-binding $V_HH$, IGF1R-1 in fusion with Fc has only marginally higher P$_{app}$ value than the internal negative control A20.1 V$_H$H. This result as well demonstrates that not all IGF1R-binding antibodies transmigrate the BBB. The data further shows that IGF1R-4-mFc has a similar high rate of transport across the BBB compared to the monovalent IGF1R-4 V$_H$H. The results are average P$_{app}$ values obtained in 3-6 independent experiments. Average Papp values of FC5 (V$_H$H) and A20.1 (V$_H$H) are also indicated by dotted lines for comparison.

Results are shown in FIGS. 6B-D. The results given are average P$_{app}$ values obtained from several independent experiments. Both negative controls have a very low P$_{app}$ value, indicating that non-specific transport or paracellular transport of these V$_H$Hs across the BBB model is minimal. IGF1R-4 V$_H$H has a high P$_{app}$ value, indicating high rate of transport across the in vitro BBB model. The P$_{app}$ for IGF1R-4 V$_H$H is 4-fold higher than that of a positive control—BBB-permeable V$_H$H FC5 (WO 02/057445). The results provide strong indication that IGF1R-4 undergoes a facilitated trans-cellular transport across brain endothelial cells in vitro and could have similar properties in vivo. Humanized IGF1R-4 $V_HH$ variants H3, H4 and H5 showed similar (H3) or slightly lower $P_{app}$ values compared to IGF1R-4 $V_HH$; H2 variant showed a significantly attenuated ability to cross in vitro BBB model, whereas H6 variants completely lost this ability, showing the same $P_{app}$ value as internal control $V_HH$ A20.1 (FIG. 6C) and was excluded from further study. The $P_{app}$ value for IGF1R-4mFc (FIG. 6D) was similar to that of a 6-fold smaller IGF1R-4 $V_HH$ (FIG. 6B), indicating that IGF1R-4 can 'carry' large (antibody-size) molecules across the BBB. $P_{app}$ value for the positive control, FC5mFc was 3-fold lower than that for IGF1R-4mFc. It is worth noting that constructs comprising IGF1R-5 or a humanized version linked to a cargo molecule (MW ~110 kDa or 180 kDa) have also been shown to be ferried across the BBB (data not shown).

Another IGF1R-binding $V_HH$, IGF1R-1 was also tested as mFc fusion in this assay. The IGF1R-1mFc had only marginally higher $P_{app}$ value that control A20.1 $V_HH$ (FIG. 6D), indicating that only a subset of IGF1R-binding $V_HHs$ isolated from immune llama library has BBB-transmigrating properties.

Absolute Quantitation of $V_HHs$ Using MRM-ILIS Method.

The methods are all as described in Haqqani et al. (2012). Briefly, to develop the SRM (selected reaction monitoring also known as multiple reaction monitoring (MRM) assay for $V_HH$, each $V_HH$ was first analyzed by nanoLC-MS/MS using data-dependent acquisition to identify all ionizible peptides. For each peptide, the 3 to 5 most intense fragment ions were chosen. An initial SRM assay was developed to monitor these fragments at attomole amounts of the digest (about 100-300 amol). Fragments that showed reproducible intensity ratios at low amounts (i.e., had Pearson r2≥0.95 compared to higher amounts) were considered stable and were chosen for the final SRM assay. To further optimize the assay, elution times for each peptide were also included, with care taken to not choose peptides that have close m/z (mass-to-charge ratio) and elution times.

A typical multiplexed SRM analysis of $V_HH$ in cell media or body fluids (serum or cerebrospinal fluid (CSF)) involved spiking known amount of ILIS (0.1-10 nM) followed by injecting 100-400 ng of CSF or cultured media proteins (0.3-1 µL) or about 50-100 ng of serum proteins (1-3 nanoliters) into the nanoLC-MS system. The precursor m/z of each target peptide ion was selected in the ion trap (and the remaining unrelated ions were discarded) at the specified elution time for the target, followed by collision induced dissociation (CID) fragmentation, and selection of only the desired fragment ions in the ion trap for monitoring by the detector. For quantification analysis, raw files generated by the LTQ (ThermoFisher) were converted to the standard mass spectrometry data format mzXML and intensities were extracted using an in-house software called Q-MRM (Quantitative-MRM; see Haqqani et al. 2012), which is a modified version of MatchRx software. For each $V_HH$, extracted-ion chromatograms were generated for each of its fragment ion that consisted of combined intensities within 0.25 Da of the fragment m/z over the entire elution time. To obtain a final intensity value for each fragment, all intensities within 0.5 min of the expected retention times were summed. A $V_HH$ was defined as detectable in a sample if the fragments of at least one of its peptides showed the expected intensity ratios, i.e., the final intensity values showed a strong Pearson correlation r≥0.95 and p<0.05 compared with the final intensities values of its corresponding pure $V_HH$.

Samples containing mixtures of $V_HH$ (media, serum, CSF) were reduced, alkylated and trypsin-digested as previously described (Haqqani et al., 2012; Gergov et al., 2003). The digests (tryptic peptides) were acidified with acetic acid (5% final concentration) and analyzed on a reversed-phase nanoAcquity UPLC (Waters, Milford, Mass.) coupled to LTQ XL ETD or LTQ Orbitrap ETD mass spectrometer (ThermoFisher, Waltham, Mass.). The desired aliquot of the sample was injected and loaded onto a 300 µm I.D.×0.5 mm 3 µm PepMaps C18 trap (ThermoFisher) then eluted onto a 100 µm I.D.×10 cm 1.7 µm BEH130C18 nanoLC column (Waters) using a gradient from 0%-20% acetonitrile (in 0.1% formic) in 1 minute, 20%-46% in 16 min, and 46%-95% in 1 min at a flow rate of 400 nL/min. The eluted peptides were ionized into the mass spectrometer by electrospray ionization (ESI) for MS/MS and SRM analysis using CID for fragmentation of the peptide ions. The CID was performed with helium as collision gas at normalized collision energy of 35% and 30 ms of activation time. Ion injection times into linear ion trap were adjusted by the instrument using an automatic gain control (AGC) target value of 6×10³ and a maximum accumulation time of 200 ms The $V_HH$-specific peptides used for detection and quantification of each $V_HH$ in multiplexed assay are shown in Table 2.

TABLE 2

Peptides used in nanoLC-SRM detection of FC5, FC5-ILIS, EG2, A20.1, IGF-1R-5 and albumin. (a) In various studies described, assays were multiplexed in different combinations for simultaneous monitoring in the same sample; (b) Heavy-labeled peptide; (c) Limits of detection and quantification of the SRM assay for each peptide ranged from 1.5-2.5 ng/ml. 1 ng/mL corresponds to about 60-70 pM of $V_HH$. A20-1 as described in Hussack et al, 2011b; EG2 as described in Iqbal et al, 2010.

| Protein | Signatures | SEQ ID NO: | Unique |
|---|---|---|---|
| IGF1R-4 | EFVGHITWSR | 25 | Yes |
| | LSCEVSGGTVSPTAMGWFR | 26 | Yes |
| FC5 | ITWGGDNTFYSNSVK | 27 | Yes |
| FC5-ILIS | ITWGGDNTFYSNSVK[b] | 27 | Yes |
| A20.1 | TTYYADSVK | 28 | Yes |
| | EFVAAGSSTGR | 29 | Yes |
| | TFSMDPMAWFR | 30 | Yes |
| | DEYAYVVGQGTQVTSSGQAGQGSEQK | 31 | Yes |

TABLE 2-continued

Peptides used in nanoLC-SRM detection of FC5, FC5-ILIS, EG2,
A20.1, IGF-1R-5 and albumin. (a) In various studies described,
assays were multiplexed in different combinations for
simultaneous monitoring in the same sample; (b) Heavy-labeled
peptide; (c) Limits of detection and quantification of the SRM
assay for each peptide ranged from 1.5-2.5 ng/ml. 1 ng/mL
corresponds to about 60-70 pM of $V_HH$. A20-1 as described in
Hussack et al, 2011b; EG2 as described in Iqbal et al, 2010.

| Protein | Signatures | SEQ ID NO: | Unique |
|---------|-----------|------------|--------|
| EG2 | DFSDYVMGWFR | 32 | Yes |
| | LEESGGGLVQAGDSLR | 33 | Yes |
| | NMVYLQMNSLKPEDTAVYYCAVNSAGTYVSPR | 34 | Yes |
| Albumin | APQVSTPTLVEAAR | 35 | Yes |

Example 10: In Vivo and Ex-Vivo Optical Imaging

To determine whether IGF1R-4 $V_HH$ accumulates in the brain after intravenous (iv) injection, IGF1R-4 $V_HH$ and negative control A20.1 $V_HH$ were conjugated to the near-infrared fluorescent tracer, Cy5.5 and purified as described in Example 7. 2.5 mg/kg of either IGF1R-Cy5.5 or A20.1 Cy5.5 (in 150 µl volume) were injected via tail vein into CD-1 nude mice, and they were imaged live in prone position in eXplore Optix preclinical imager MX2 (Advanced Research Technologies, QC) 30 min after injection. One hour after injections, animals were anesthetized with 2% isoflurane (Baxter Canada, Mississauga, ON, Canada), cardiac puncture was made and 10 mL of saline (Baxter Canada, Mississauga, ON, Canada) supplemented with 1 EU/mL heparin (Organon, Toronto, ON, Canada) was perfused from the same needle at 2 mL/min to remove the blood (ascertained by the appearance of blood-free fluid at the site of right ventricle incision). The perfused brains were removed and imaged ex vivo using in eXplore Optix. The imaging protocols were as described in detail in Iqbal et al., 2011.

Figure 7:
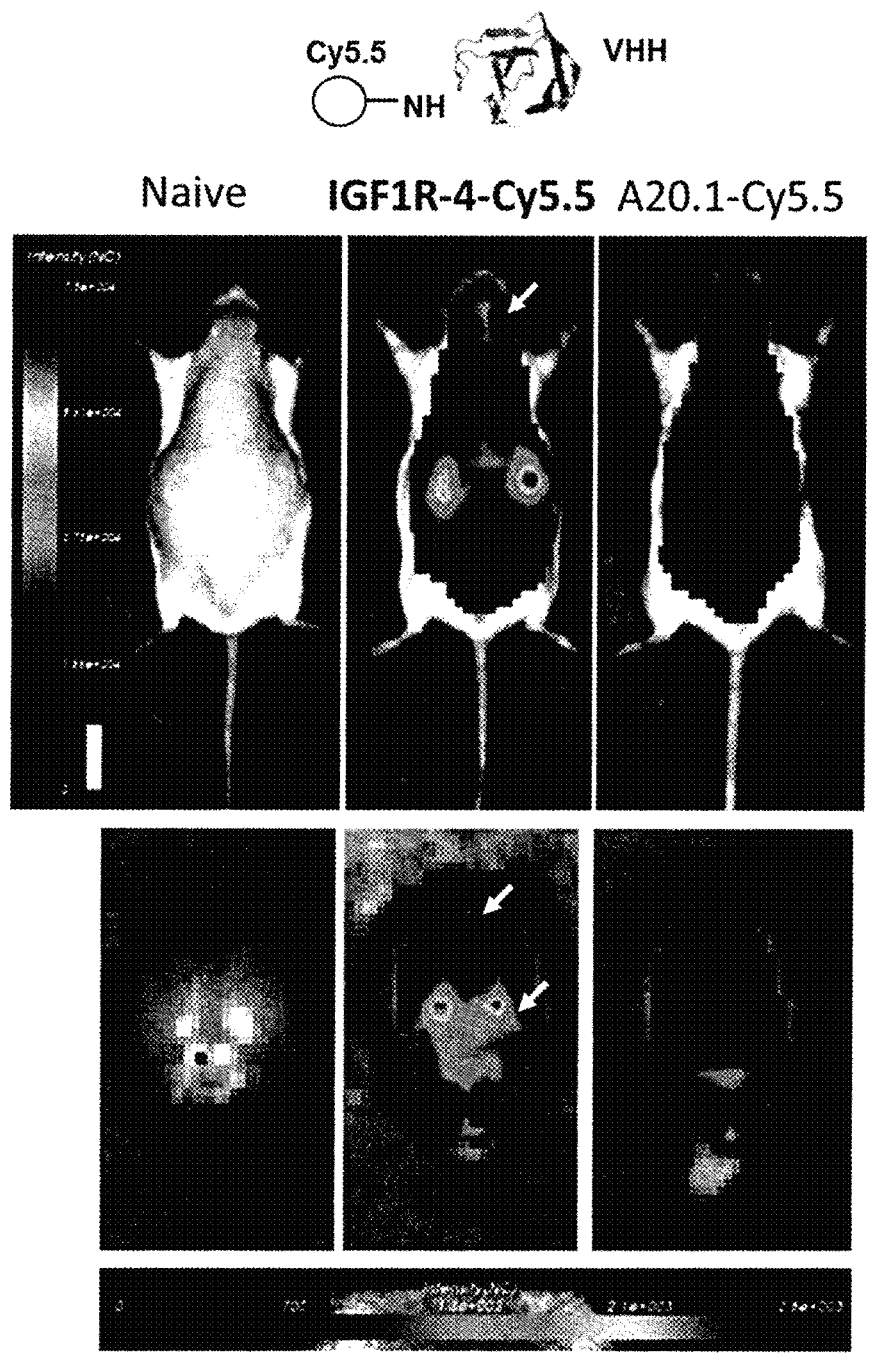
FIG. 7 (upper panels) shows in vivo whole body images of CD-1 mice injected intravenously with PBS (naïve) or 2.5 mg/kg of either Cy5.5-IGF1R-4 V$_H$H or Cy5.5-A20.1 V$_H$H (schematic of injected molecules is shown on top) and scanned in eXplore Optix time-domain optical imager 30 min after injection. Bottom panels show ex-vivo brain images of the same animals obtained 1 h after V$_H$H injection and after transcardial perfusion to remove antibodies from the circulation. Arrows indicate high optical signal (light gray) of the fluorescent tracer in the head and in ex-vivo brain in the animal injected with Cy5.5-IGF1R-4, whereas it cannot be detected in the animal injected with the Cy5.5-A20.1 control (black).

The results are shown in FIG. 7. Mice injected with Cy5.5-IGF1R-4 showed enhanced optical signal in the head region in vivo (upper panels, arrow) and in ex-vivo brain after perfusion (bottom panels, arrows), whereas Cy5.5-A20.1-injected mice showed only low background signal. The data suggest that IGF1R-4 $V_HH$ can deliver imaging agent (Cy5.5, 1 kD) across the blood-brain barrier in vivo.

Example 11: Conjugation of IGF1R-4 to Galanin

To determine whether IGF1R-4 $V_HH$ can cross the blood-brain barrier (BBB) in vivo and 'ferry' across the BBB a molecule that cannot cross the BBB on its own, the neuropeptide Galanin was chemically conjugated to IGF1R-4 $V_HH$ or to IGF1R4-mFc and administered systemically. Galanin is a neuroactive peptide that produces analgesia by binding GalR1 and GalR2 expressed in brain tissue. When given peripherally, Galanin has no analgesic effects because it cannot cross the BBB on its own (Robertson et al., 2011).

Figure 8A:
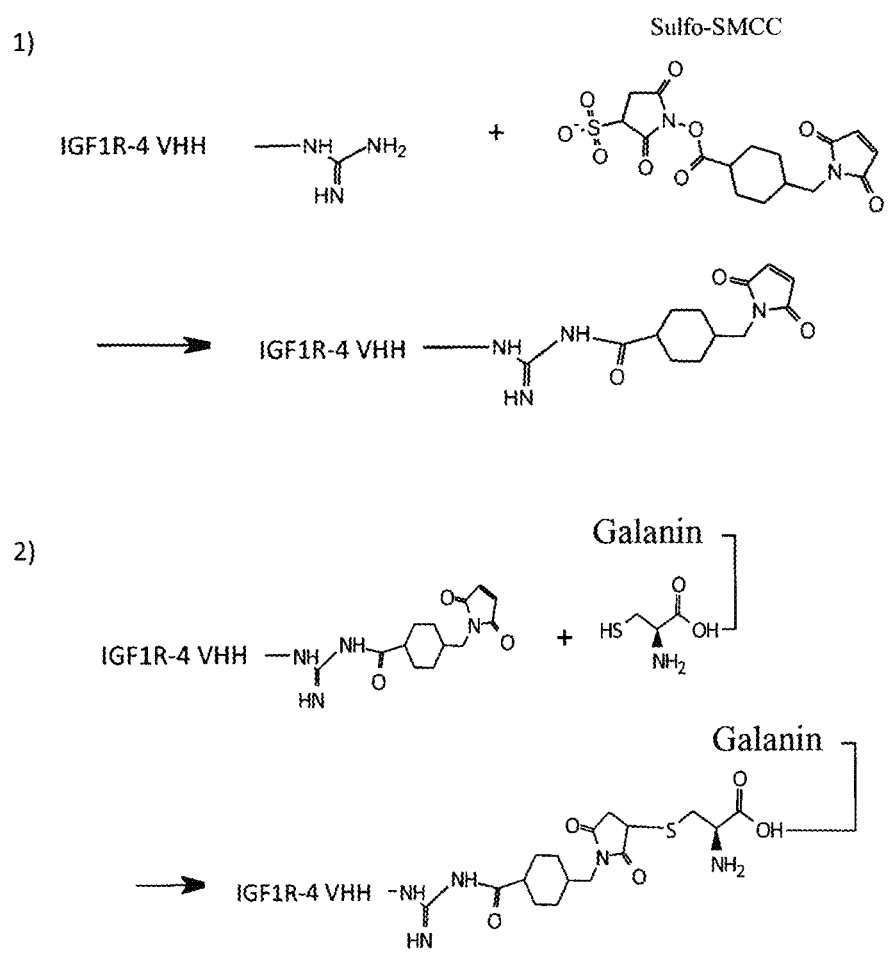
FIG. 8A shows the scheme for chemical synthesis of IGF1R-4 V$_H$H-Galanin conjugate. IGF1R-4 was first conjugated to the NHS group of a Sulfo-SMCC cross-linker (1); then maleimide-activated IGF1R-4-sulfo-SMCC was conjugated to the reduced cysteine of Galanin (2).

The IGF1R-4 $V_HH$ was conjugated to a rat Galanin (Gal) fragment with cysteamide modified C-terminus (Biomatic) (GWTLNSAGYLLGPHAIDNHRSFSDKHGLT-cysteamide, SEQ ID NO:36). The scheme for conjugation is shown in FIG. 8A.

Briefly, 5 mg of IGF1R-4 $V_HH$ (Example 4) in 0.5×PBS, 2.5 mM EDTA at [2 mg/ml] were mixed with 436.4 µl of 2.5 mg/ml sulfosuccinimidyl-4-(N-maleimidomethyl)cyclohexane-1-carboxylate (Sulfo-SMCC) (7.5× excess molar ratio). The mixture was then flushed with nitrogen gas and incubated for 30 minutes at room temperature (RT) to allow the NHS ester arm of the Sulfo-SMCC to react with amines on the $V_HH$. Subsequently the unreacted Sulfo-SMCC was removed from the maleimide-activated IGF1R-5 $V_HH$ using a 10 ml 7K Zeba column (Pierce). Prior to sample loading, the column was washed 3 times with 5 ml PBS and spun at 1000×g for 2 min. After sample loading, the column was topped-up with 200 µl of PBS and was spun for 2 min at 1000×g. As for the IGF1R-Fc constructs, 5 mg were reacted with ~68 µl of Sulfo-SMCC (6.5× excess molar ratio) in the same way as described above.

Separately and concurrently, cysteamide modified C-TERM galanin (Gal-cya) was prepared by dissolving 10 mg of lyophilized powder in 10 ml of endotoxin free water to make a 1 mg/ml stock (the galanin-cya powder has a small amount of DTT to prevent disulfide bridge formation during purification). Finally, 100 µl of 0.5M EDTA was added (5 mM final concentration).

The purified maleimide-activated IGF1R-4 $V_HH$ and IGF1R-Fc constructs (2.6 ml) were diluted to 5 ml with 0.5×PBS, 2.5 mM EDTA and then 5 ml or 1 ml Gal-cya respectively was added while vortexing. The samples were flushed with nitrogen, sealed and incubated overnight at 4° C. The next day, the unreacted Gal-cya was removed using Amicon-15 10K and 30K column (Millipore) respectively. The sample were added to the column and spun at 4000×g for 7 minutes until the volume was reduced to 5 ml. 5 ml of 0.5×PBS, 2.5 mM EDTA was added to the remaining 5 ml sample in the column's insert and was spun again until the sample was reduced to 4 ml. The conjugated samples were then added to a 10 ml 7K Zeba column (Pierce), prepared as described above, and then spun for 2 min at 1000×g.

Figure 8B:
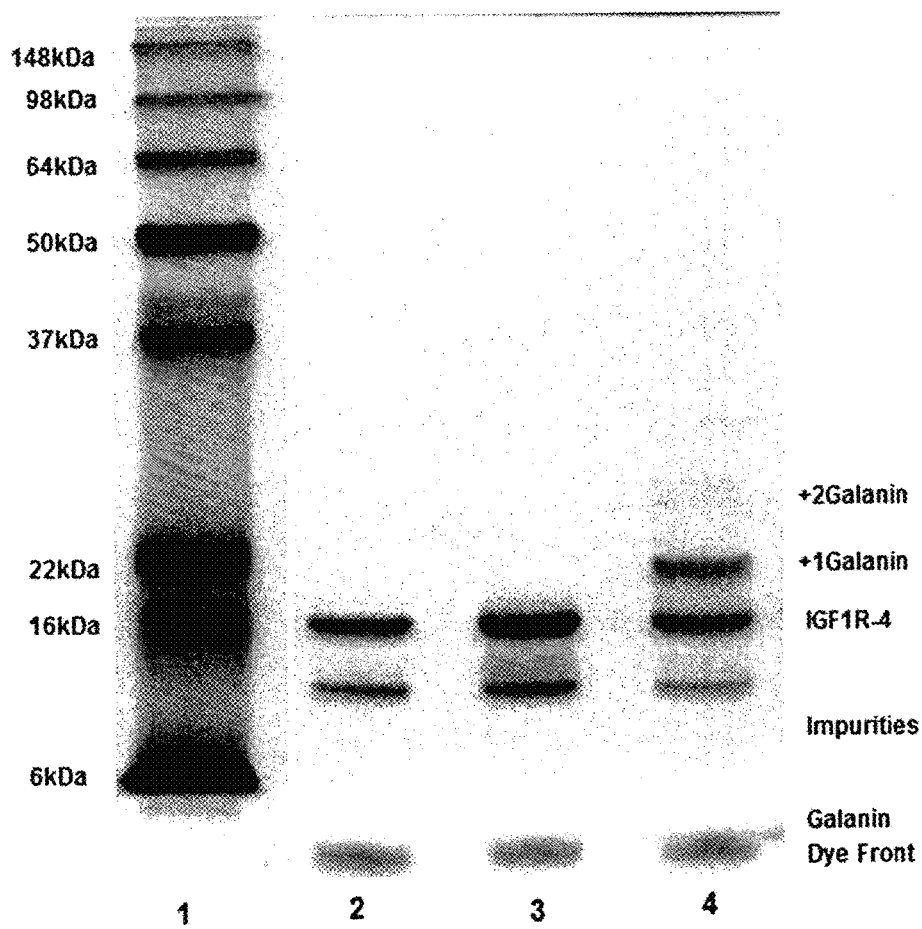
FIG. 8B shows SDS-PAGE gel of IGF1R-4 (lane 2), IGF1R-4-SMCC (lane 3), and IGF1R-4-Galanin conjugate (lane 4). The 'banding' pattern indicates the attachment of 1-2 galanin molecules per IGF1R-4. The same conjugation methods were used to link Galanin with IGF1R-mFc.

Conjugated IGF1R-4-Gal and IGF1R-4 Fc-Gal samples were then ran on a 16% or 10% SDS-PAGE non-reducing gel and silver stained to confirm shift in molecular weight size after conjugation. The reaction was titrated to achieve ~1 to 2 galanin molecules per $V_HH$ or IGF1R-Fc constructs. Results confirm the galanin load on the IGF1R-4 $V_HH$ (see FIG. 8B).

Endotoxin Removal and Determination of Endotoxin Levels:

Endotoxins were removed using Amicon Ultra-molecular weight cut-off (MWCO) cellulose membrane spin columns (Millipore). First, 15 ml of the $V_HH$ preparation was passed through an Amicon-15-50K MWCO column by centrifugation at 4000×g for 10 minutes; the elution was collect. This elution was then added to an Amicon-15-10K MWCO column and spun at 4000×g for 7-10 minutes resulting in a reduction of the supernatant volume from 15 ml to 7.5 ml.

The supernatant volume in the column was adjusted back to 15 ml by adding PBS. The column was spun again as described above. The supernatant was collect and the endotoxin levels were measured with EndoSafe-PTS system using cartridges with a sensitivity range of 10-0.1 EU/ml (Charles River Laboratories International). 25 ul of sample was loaded in each of the 4 wells on the cartridge and diluted if necessary. Only samples with EU<1 per 1 mg were used for animal studies.

Example 12: Transport of the IGF1R-4-Gal Using the Hargreaves Model

To evaluate whether the IGF1R-4-Gal or IGF1R-4-mFc-Gal (Example 11) transmigrate the blood-brain barrier, an in vivo assay, was utilized, previously described in International Patent Publication No. WO 2011/127580.

A rat model of inflammatory hyperalgesia, similar to that described by Hargreaves et al. (1988), was used. Animals were housed in groups of three (Hargreaves model) per polypropylene cage, and were allowed free access to food and water. Experiments were done in a 12 h light/dark cycle at a temperature of 24° C. and a relative humidity of 50±5%. All animal procedures were approved by the NRC's Animal Care Committee and were in compliance with the Canadian Council of Animal Care guidelines.

In this model, male Wistar rats, 6-8 weeks (weight range 230-250 g) old were injected with low volume (100 µl with a 30-gauge needle) of complete Freund's adjuvant (CFA; heat-killed *M. tuberculosis* (Sigma) suspended in oil:saline 1:1 emulsion) into the right hind paw under brief isoflurane anesthesia (3%). CFA induces the release of pro-inflammatory substances that activate nociceptors and create a chronic pain state and hyperalgesia (a heightened sensitivity to noxious heat). The paw withdrawal latency was measured by the application of a radiant stimulus in the plantar surface in both hind paws (inflamed an non-inflamed control paw) using the plantar Analgesia Meter equipment for paw stimulation (IITC Model #336TG Life Science, Inc.). The time taken by the animal to respond by licking or flicking its paw was interpreted as positive response (paw withdrawal latency). The light-intensity lamp was adjusted to elicit baseline paw withdrawal latencies between 17 to 20 s in both hind paws before CFA administration. If a withdrawal response does not occur within 20 s, the light beam was automatically turned off to avoid tissue damage and the paw was assigned the maximum score.

Two days post-CFA injection and prior to the administration of the compounds, the animals were manipulated and acclimatized in the analgesia meter equipment for at least 60 min with the aim to reduce stress and prevent false positive responses The baseline was measured in both paws to verify the developed pain (thermal hyperalgesia); the non-inflamed paw was used as a control against the injected paw. Animals with paw withdrawal latency of more than 6 s for the "inflamed paw" and less than 17 s for the "normal paw" were excluded from the experiment.

To determine whether IGF1R-4-Gal is delivered across the blood brain barrier and can engage target receptors (GalR1 and 2) in brain parenchyma, the rats received one tail vein injection of IGF1R-4-Galanin (3 mg/kg) or IGF1R-4mFc-Galanin (2 mg/kg or 5 mg/kg) or control compounds three days post-CFA injection. The paw withdrawal latency (PWL) was tested for each hind paw (inflamed and non-inflamed) every 15 min for 3 hours. An increased latency of paw withdrawal indicates suppression of thermal hyperalgesia, which can only be obtained through successful delivery of Galanin into the brain parenchyma by IGF1R-4. Galanin can only induce analgesia when present in the brain parenchyma and on its own cannot cross an intact BBB (Robertson et al., 2011).

Figure 9A:
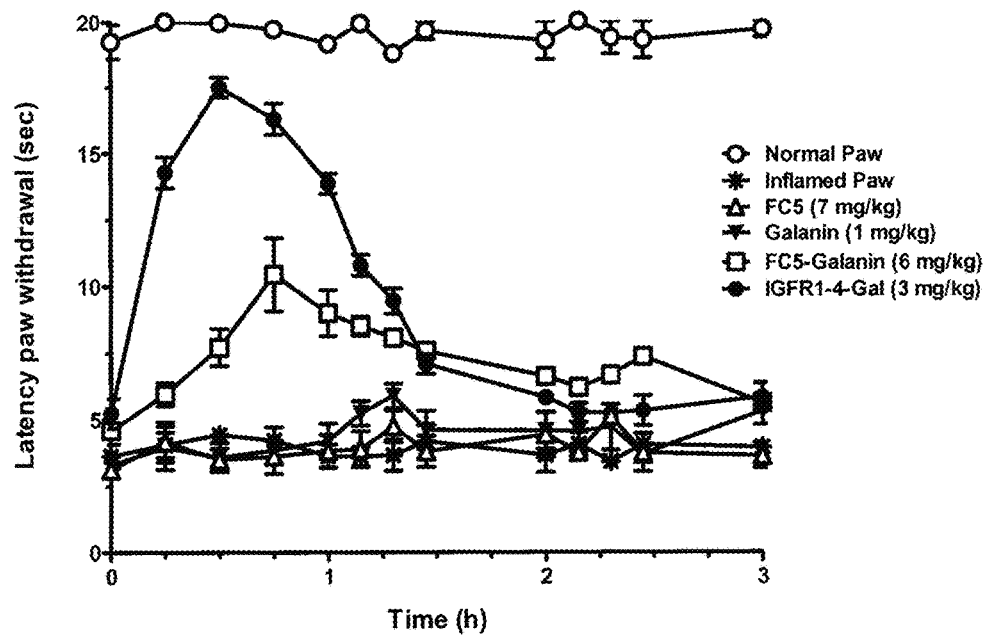
FIG. 9A is a graph showing the ability of IGF1R-4 to deliver pharmacologically efficacious doses of the analgesic peptide Galanin (3.2 kD) into the brain using Hargraeves pain model. In this model, localised chronic pain is induced in male Wistar rats (4-6 weeks age), by injecting 100 µl of complete Freund's adjuvant (CFA) into the left plantar surface, causing a local inflammation within a few hours. Following tail vein injection of the BBB carrier V$_H$H-drug conjugate or Galanin alone, the rats are placed into Plexiglas enclosures set on a glass surface. A thermal stimulus is focused on the inflamed or contralateral paw via an angled mirror. The latency between stimulus application and paw withdrawal (lick or flick of paw) is interpreted as a measure of the analgesic effect (inhibition of thermal hyperalgesia). The peptide Galanin alone cannot penetrate the BBB, as demonstrated by the lack of analgesic effect after systemic (tail-vein) injection of 1 mg/kg Galanin (solid black triangles). Systemic injection of IGF1R-4-Galanin conjugate (3 mg/kg) inhibits thermal hyperalgesia, reaching maximal reversal 30 min after administration (solid black circles); the effect was more pronounced than that observed with the 6 mg/kg of FC5-Galanin conjugate (white open squares).
Figure 9B:
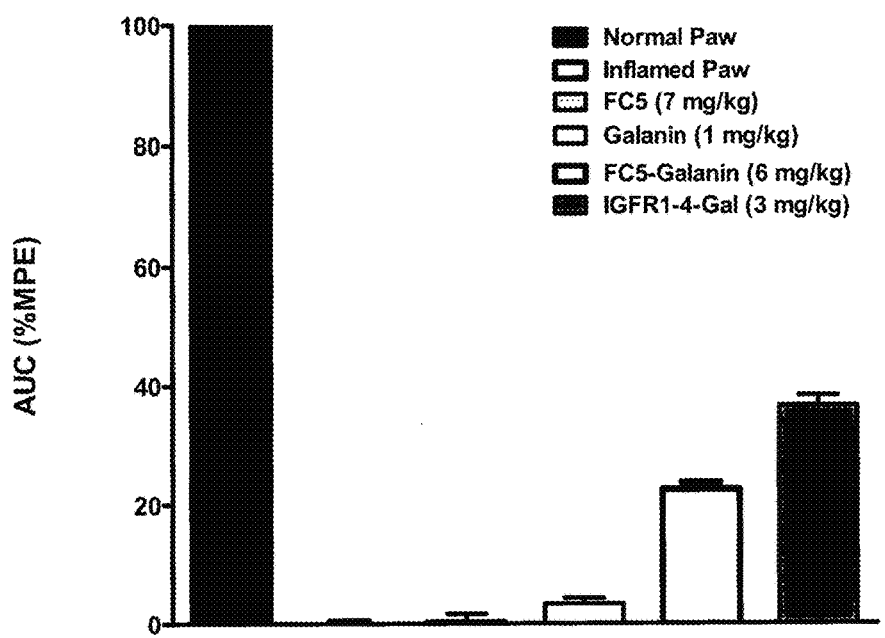
FIG. 9B shows these results as area under the curve (AUC) of the response compared to the maximal possible effect (MPE; control paw).
Figure 9C:
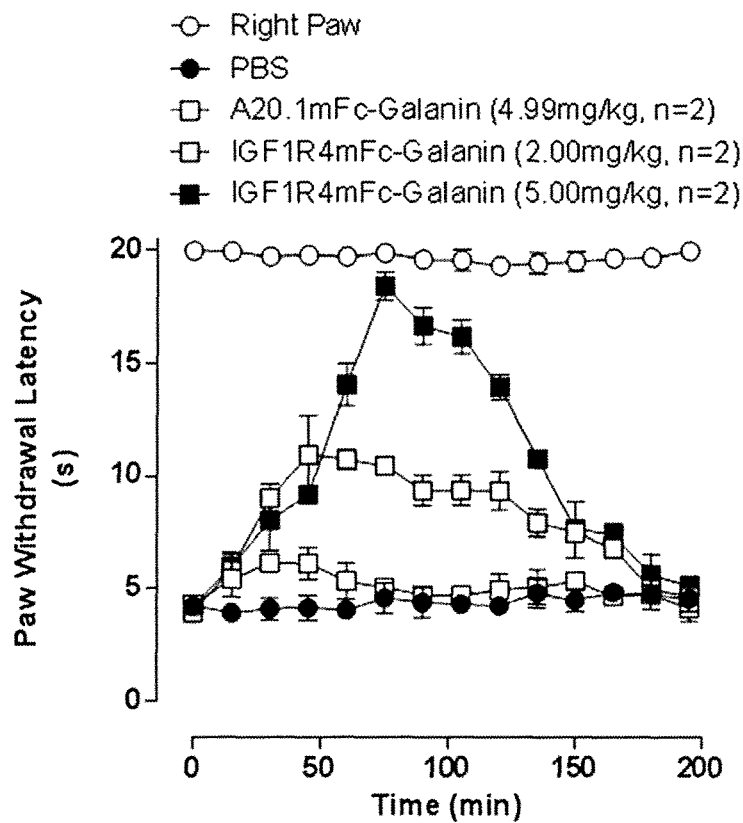
FIG. 9C shows dose-dependent (2 mg/kg and 5 mg/kg) inhibition of thermal hyperalgesia in Hargreaves model of inflammatory pain with IGF1R-4-mFc-Galanin conjugate administered iv. In contrast, A20.1-mFc-Galanin (5 mg/kg) did not induce any reversal of thermal hyperalgesia.
Figure 9D:
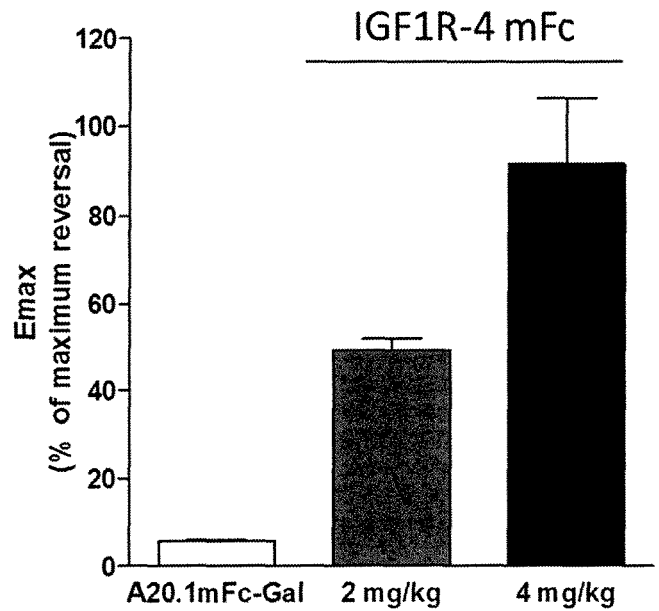
FIG. 9D shows percent reversal of thermal hyperalgesia (Emax) at the peak of response achieved with various doses of A20.1-mFc-Galanin and IGF1R-4-mFc-Galanin.

Results were analyzed as temporal courses of Paw Withdrawal Latencies (PWL, sec) versus time (min or hrs) (FIGS. 9A and C). FIG. 9B shows the results as area under the curve (AUC) and compares it to the % of Maximum Possible Effect (% MPE). FIG. 9D shows the results as percent reversal (of thermal hyperalgesia) at the peak response (Emax).

The results show that intravenously administered galanin does not reduce pain compared to PBS. In contrast, a single injection of FC5-Gal or IGF1R4-Gal produce measurable analgesic effect, suggesting that this $V_HH$ 'ferries' Galanin across the BBB to produce an analgesic effect by binding to GalR1 and/or 2 in the brain parenchyma. The effect of IGF1R-4-Galanin is significantly more pronounced than that induced by FC5-Gal, suggesting that the IGF1R receptor has a higher rate of BBB transport than the putative FC5 receptor. The results demonstrate that IGF1R-4 $V_HH$ can 'ferry' molecules of at least 3000 Da across the BBB using receptor-mediated transcytosis pathway (the combined MW of antibody-peptide conjugate is about 18 kDa). Active, receptor mediated transport is required since the BBB is known to prevent the passage of all hydrophilic molecules greater than 0.5 kDa. Similarly, IGF1R4-mFc-Galanin produces a dose-dependent suppression of thermal hyperalgesia whereas A201.mFc-Galanin is ineffective. This suggests that IGF1R-4 $V_HH$ can ferry molecules similar in size to antibodies (~80 kD) across the BBB. The IGF1R-4mFc-Galanin was about 5-fold more potent in suppressing thermal hyperalgesia than IGF1R-4-Galanin, suggesting that bi-valent display and extended plasma half-life contribute to improved efficacy of brain delivery.

Example 13: IGF1R-4 Levels in CSF and Plasma

An in vivo assay was carried out to determine whether IGF1R-4 $V_HH$ is able to cross into the brain, and specifically into the cerebrospinal fluid (CSF), as well as to quantify its presence in CSF and serum.

Animals were housed singly in polypropylene cages, and were allowed free access to food and water. Experiments were done in a 12 h light/dark cycle at a temperature of 24° C. and a relative humidity of 50±5%. All animal procedures were approved by the NRC's Animal Care Committee and were in compliance with the Canadian Council of Animal Care guidelines.

Male Wistar rats, 8-10 weeks of age (weight range, 230-250 g) were used. To sample CSF, the fur on the neck and head region of animals was shaved and they were then placed in a Plexiglas chamber and moderately anesthetized with 3% isoflurane; the CSF was collected essentially as described by Nirogi et al (2009). The anesthetized rat was placed in a metal frame instrument (generously provided by Dr. Vinicio Granados-Soto; CINVESTAV, Mexico) and immobilised using earbars. The position of the animal's head was maintained downward at approximately 45°. A depressible surface with the appearance of a rhomb between the occipital protuberance and the spine of the atlas was made visible by rubbing the cotton embedded in ethanol (75%) over this surface. 27G needle covered with PE-10 tubing (Becton Dickinson, Mississauga, ON, Canada) 10 cm in length and connected to a 100 cc insulin syringe was inserted horizontally and centrally into the cisterna magna for CSF collection without making incisions. Two resistance points (clicks) along the needle path can be easily felt, due to the tearing of the skin and the ripping of atlanto-occipital membrane. When the needle passed the second resistance point, CSF was collected (40-100 μL) through the needle by applying a gentle suction of the insulin syringe. After the CSF sampling, corresponding blood was collected by cardiac puncture after thoracotomy and placed in vacutainer tubes (Becton Dickinson, Mississauga, ON, Canada) with clot activator and gel, and then centrifuged at 3,000×g for 15 min. Serum was removed using a micropipette and rapidly frozen at −80° C. until further analyses.

Serum and CSF samples were analyzed by mass spectrometry and nanoLC-SRM based quantification as described in Example 9.

CSF collection is a delicate procedure during which CSF can be easily contaminated with blood. Since the amounts of $V_HH$ s are expected to be much smaller in the CSF (<0.1%) than blood, even a slight contamination with blood could seriously compromise the value of an individual CSF sample. It was therefore necessary to develop stringent exclusion criteria for blood-contaminated CSF samples. To evaluate blood-CSF albumin ratio, a nanoLC-SRM method was developed for quantifying albumin levels in plasma and CSF. An albumin peptide APQVSTPTLVEAAR (SEQ ID NO:37) was selected based on its unique retention time and m/z value (Mol Pharm) in order to have minimum interference with other peptide peaks in the multiplex assay. The intensity of the peptide was quantified in both CSF and plasma samples using SRM as described above. The albumin ratio was calculated as follows for each rat:

Albumin Ratio=Intensity per nL of plasma analyzed/ Intensity per nL of CSF analyzed A ratio of 1500 and below was considered as blood contaminated.

Figure 10:
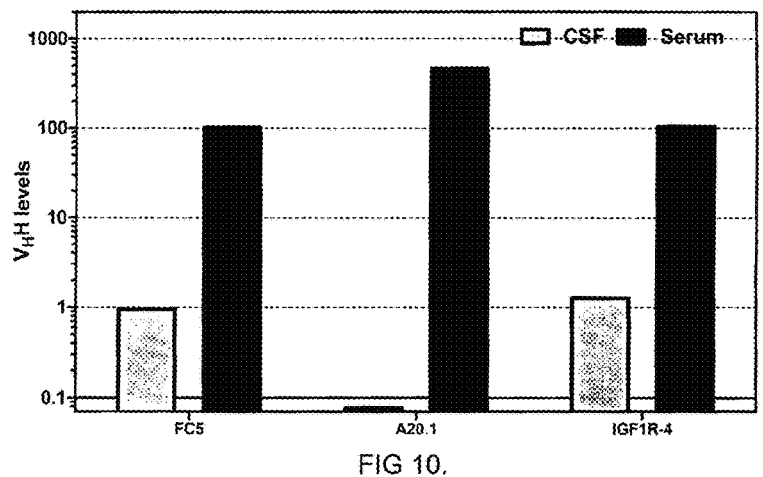
FIG. 10 shows plasma and CSF levels of IGF1R-4, and 'positive' control V$_H$H, FC5 and 'negative' control V$_H$H A20.1 30 min after systemic (tail vein) co-administration of 6 mg/kg of each antibody The CSF was collected from cisterna magna. Plasma and CSF levels of IGF1R-4, FC5 and A20.1 were determined using the MRM-ILIS method that 'tracks' and quantifies specific protein peptide signatures. Albumin levels in the CSF were concurrently determined by MRM. All CSF samples having a plasma/CSF ratio lower than 1500 were excluded as potentially blood-contaminated. The CSF/serum ratio for IGF1R-4 was 1.2% compared to 0.9% for FC5 and 0.017% for A20.1.

Results are shown in FIG. 10. Animals were co-injected with 6 mg/kg each of IGF1R-4, FC5 or A20.1, and CSF and serum were collected 30 min after injection. The figure shows that CSF/serum ratio for IGF1R-4 is 1.2%, compared to 0.98% for FC5 and 0.017% for A20.1, suggesting that both IGF1R-4 and FC5 have higher CSF penetration and brain exposure from co-injected control antibody, A20.1.

Example 14: Immunodetection of IGF1R-4-mFc

To ascertain that high levels of IGF1R-4-mFc detected in the CSF after peripheral administration originate at least in part from parenchymal extracellular space, in other words, that the intact construct had crossed the BBB, immunodetection of IGF1R-4-mFc in rat brains was performed.

Briefly, brains of animals were harvested immediately following animal perfusion with PBS 24 h after 6 mg/kg tail-vein injection of either IGF1R-4-mFc or A20.1mFc. The brains were frozen and sectioned on cryotome into 12 μm sections. Sections were fixed for 10 min RT in 100% Methanol, washed 3× in PBS and incubated for 1 h in 10% normal goat serum (NGS) containing 0.3% TritonX-100 in 1×PBS. Goat anti-m-IgG Fcγ-cy3 (Cat#115-165-071, Jackson Immuno Research, lot#106360) 1:200 in 5% NGS containing 0.3% TritonX-100 in 1×PBS was applied overnight at 4° C. Sections were washed three times in 1× Vasculature-staining lectin RCAI (Cat# FL-1081, Vector) 1:500 in 1×PBS was then added for 10 min. After washing three times with 1×PBS, sections were covered with a cover slip in Dako fluorescent mounting medium (Cat#S3023, Dako) and spiked with 2 μg/mL Hoechst (Cat#H3570, Invitrogen) to stain nuclei. Images were captured with Olympus 1×81 Fluorescent Microscope using 10× and 60× Objectives and channels as shown in Table 3.

TABLE 3

Objectives and channels used for fluorescent microscopy.

| | Fluorescent molecule | Excitation (nm) | Emmision (nm) |
|---|---|---|---|
| RCAI-vessels | FITC | 495 | 518 |
| Hoechst33342-nuclei | Hoechst | 350 | 461 |
| IGF1R-5-m-Fc | Cy3 | 531 | 593 |

Figure 11:
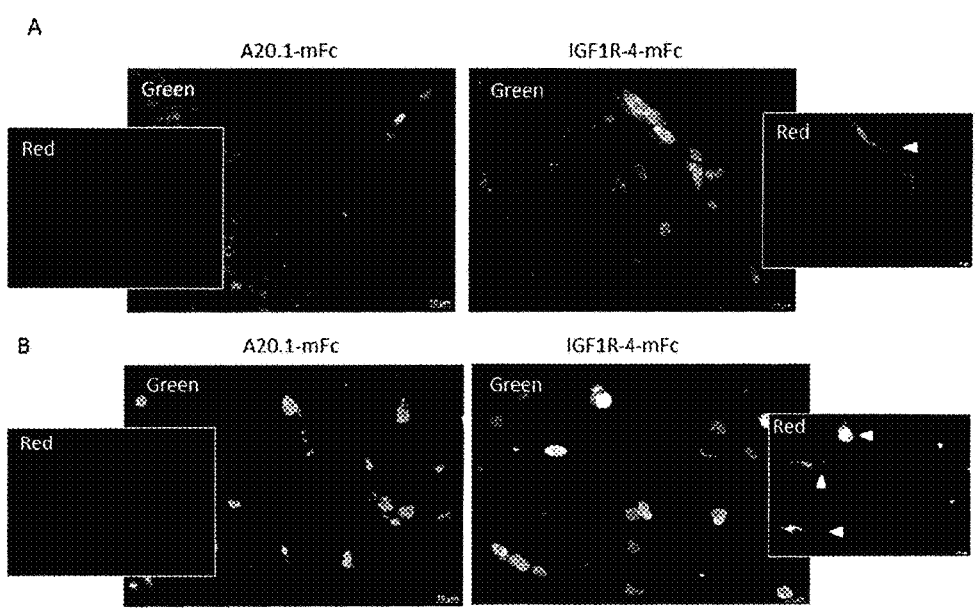
FIG. 11 shows immuno-detection of IGF1R-4mFc in brain sections 24 h after tail-vein administration of a 6 mg/kg dose. Sacrifice perfusion with PBS was carried out on the rats and brain sections (12 µm) were obtained using the vibratome. IGF1R-4mFc was immuno-detected using an anti-mouse Fc antibody (red; red channel only shown in inserts). Blood vessels in the brain section (dentate gyrus, A; frontal cortex, B) were detected using lectin RCA1 (green). IGF1R-4mFc could be detected in both vessels and outside the vessels (i.e. in the brain parenchyma, transmigrated across the BBB) as indicated by arrowheads.

Results are shown in FIG. 11. Immunodetection of mouse Fc showed strong staining of brain vessels throughout different brain regions, as well as staining of perivascular brain parenchyma, indicating that the IGF1R-4-mFc is accumulated in brain vessels and also transmigrated the BBB into surrounding brain parenchyma. In contrast, no mFc-specific staining could be detected in A20.1mFc-injected animals. The results support the assertion that increased CSF levels of IGF1R-4-mFc are indicative of the construct transmigration across the BBB. This is further strongly supported by the observation that galanin linked to IGF1R-4 induced pharmacological response (analgesia) on parenchymal GalR1 and GalR2 receptors. Collectively, in vitro BBB transmigration results, in vivo pharmacokinetic (serum/CSF levels) and pharmacodynamic (Hargreaves model) results demonstrate that IGF1R-4 $V_HH$ transmigrates the intact BBB at significantly higher rates than other $V_HH$s via active receptor-mediated transcytosis triggered by its binding to IGF1R epitopes and that it can 'ferry' a range (1-80 kD) of otherwise non-permeable molecules across the blood-brain barrier.

Example 15: IGF1R-4 Effect on 'Physiological' Function of IGF1R

From a safety perspective, it is important to show that the antibody of the invention does not interfere with the physiological function of the receptor—i.e., signaling induced by its natural ligand, IGF-1—when engaging its receptor for drug delivery via receptor-mediated transcytosis. In view of this, it is important to demonstrate that IGF1R-4 $V_HH$ or IGF1R-4-mFc do not interfere with physiological signaling through IGF1R or the related insulin receptor (IR) induced by their natural ligands.

To determine whether IGF1R-4 induces signaling through IGF1R or IR alone, or interferes with signalling as stimulated by the receptor's natural ligands, IGF-1 or insulin, their effect on phosphorylation of the receptors themselves or receptor-stimulated downstream kinase, Akt, was determined in SV-ARBEC cells.

SV-ARBEC were grown to confluence in M199 base medium supplemented with peptone, D-glucose, BME amino acids, BME vitamins, antibiotic/antimycotic solution and fetal bovine serum, according to art-known methods. The cells were switched into serum free medium 18 h prior to treatment. IGF1R-4 $V_HH$ or IGF1R-4-Fc fusion (100 nM or 500 nM) was added to the cells 1 h prior to the addition of either 200 ng/ml IGF-1, 10 μg/ml of insulin or vehicle. The cells were incubated with ligands or vehicle for 20 minutes and then washed twice in Hank's balanced salt solution. Cells were subsequently lysed using 1×RIPA buffer (Cell Signaling Technology) supplemented with 1% Triton-x 100 and protease inhibitor cocktail (Sigma). The cells were given 2×20 second bursts in a water bath sonicator and lysates were clarified by centrifugation at 14,000 rpm for 10 minutes. Protein concentration was determined using DC protein assay system (BIO-RAD laboratories). Equal μg of protein samples were resolved on a 4-20% gradient SDS polyacrylamide gel at 125V and transferred to PVDF membrane. Phospho-Akt (Ser 473) was detected by overnight incubation in 1:1000 dilution of the primary antibody against this target (Cell Signaling Technology) followed by a 1 h incubation with goat anti-rabbit IgG-HRP secondary antibody then reacted with ECL Plus reagent and visualized on autoradiography film. Densitometry values were determined using Un-Scan-It software (Silk Scientific Inc.).

Figure 12A:
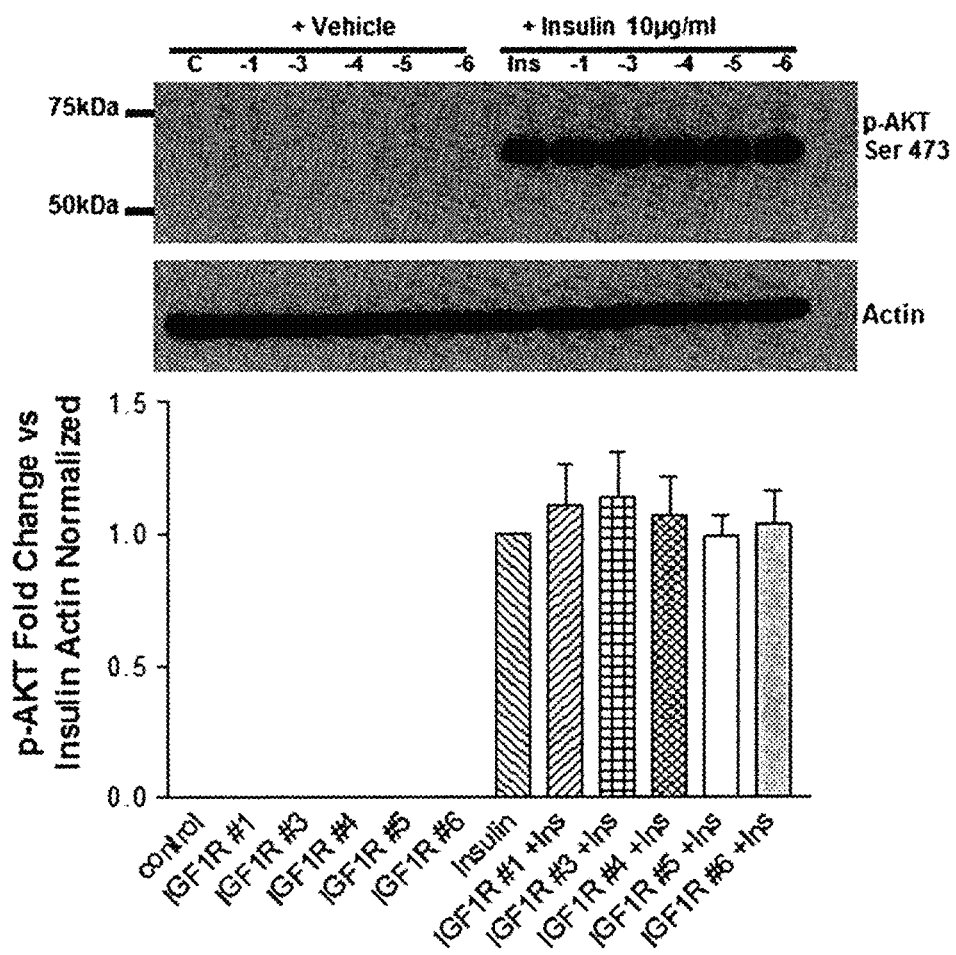
FIG. 12A is a representative Western blot showing that neither IGF1R-4, nor any of the other anti-IGF1R V$_H$H tested (IGF1R-1, -3, -5, or -6) induce downstream Akt phosphorylation alone at a concentration of 100 nM. Neither does the presence of 100 nM of IGF1R-4, or any of the other anti-IGF1R V$_H$Hs inhibit Akt phosphorylation as induced by 10 µg/ml of insulin. The quantitation of Western blot band densities from 3 independent experiments is shown in the bar graph (average+/−SD) below the gel image.
Figure 12B:
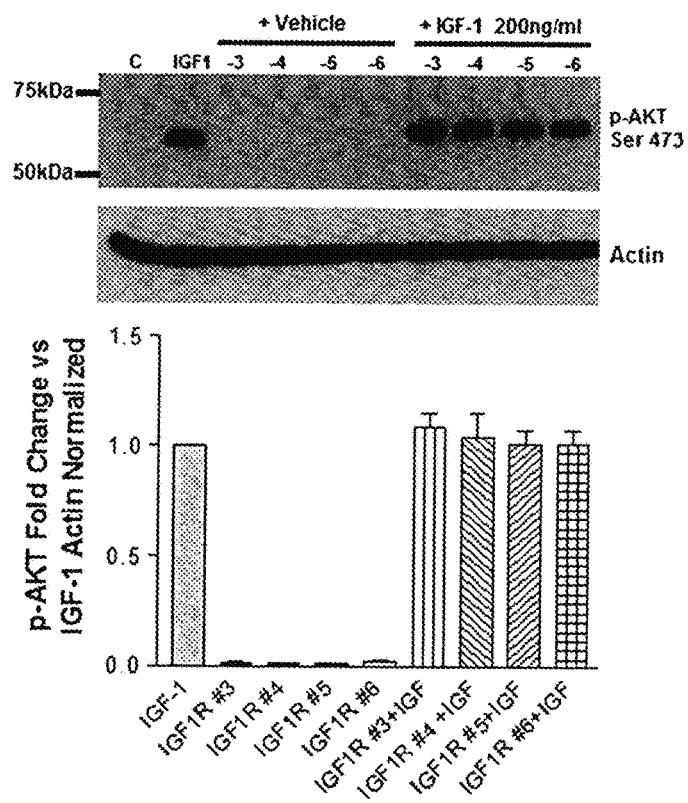
FIG. 12B is a representative Western blot showing that neither IGF1R-4, nor any of the other anti-IGF1R V$_H$H tested (IGF1R, -3, -5, or -6) at 100 nM induce phosphorylation of Akt on their own and neither inhibit IGF-1 induced Akt phosphorylation (i.e. signaling) induced upon stimulation with 200 ng/ml of IGF-1. The quantitation of Western blot band densities from 3 independent experiments is shown in the bar graph (average+/−SD) below the gel image.
Figure 12C:
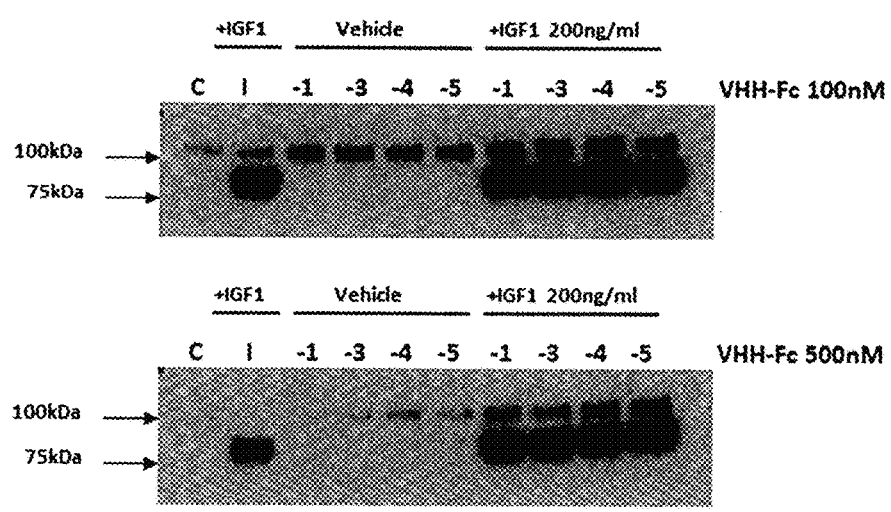
FIG. 12C shows Western blots probed for phosphorylated IGF1R. Cells were incubated with either 100 nM or 500 nM IGF1R-4-mFc, or any of the other anti-IGF1R V$_H$H-mFc fusions (IGF1R-1, -3, or -4-mFc) alone or stimulated with 200 ng/ml IGF-1 in presence of the respective IGF1R-V$_H$H-mFc fusion proteins. The Western blots indicate that none of the fusion constructs inhibited IGF-1 induced phosphorylation of IGF1R and neither induced receptor phosphorylation on their own.

The results are shown in FIG. 12. Western blot analyses of Akt phosphorylation showed that IGF1R-4 did not inhibit Akt phosphorylation induced by 10 μg/ml of insulin or by 200 ng/ml of IGF-1 when co-applied with at 100 nM of IGF1R-4 or IGF1R-4-mFc or 500 nM IGF1R-4-mFc. Neither did either of the $V_HH$ or Fc fusions induce Akt signalling on its own (FIGS. 12A, 12B and 12C, labelled "–4"). The results demonstrate that even in bivalent display in the Fc fusion format IGF1R-4 does not trigger receptor dimerization and down-stream signaling, and therefore does not interfere with the receptor function in the presence of the natural ligand. This feature of IGF1R-4 ('silent binder') is important for its application as a BBB carrier for therapeutics, since it confers a favourable safety profile.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

REFERENCES

All patents, patent applications and publications referred to herein and throughout the application are hereby incorporated by reference.

Abbott N J (2013) Blood-brain barrier structure and function and the challenges for CNS drug delivery. J Inherit Metab Dis. 36(3):437-49.

Abulrob A, Sprong H, Van Bergen en Henegouwen P, Stanimirovic D (2005) The blood-brain barrier transmigrating single domain antibody: mechanisms of transport and antigenic epitopes in human brain endothelial cells. J Neurochem. 2005 November; 95(4):1201-14.

Arbabi-Ghahroudi, M. Desmyter A, Wyns L, Hamers R., and Muyldermans S (1997) Selection and identification of single domain antibody fragments from camel heavy-chain antibodies, FEBS Lett 414, 521-526

Arbabi-Ghahroudi, M., To, R., Gaudette, N., Hirama, T., Ding, W., MacKenzie, R., and Tanha, J. (2009a) Protein Eng. Des. Sel. 22, 59-66.

Arbabi-Ghahroudi, M., MacKenzie, R., and Tanha, J. (2009b) Methods Mol. Biol. 525, 187-216.

Bell, A., Wang, Z. J., Arbabi-Ghahroudi, M., Chang, T. A., Durocher, Y., Trojahn, U., Baardsnes, J., Jaramillo, M. L., Li, S., Baral, T. N., O'Connor-McCourt, M., Mackenzie, R., and Zhang, J. (2010) Cancer Lett. 289, 81-90.

Broussau, s., Jabbour, N., Lachapelle, G., Durocher, Y., Tom, R., Transfiguracion, J., Gilbert, R. and Massie, B. (2008) Mol Ther 16, 500-507.

Chothia, C., and Lesk, A. M. (1987) J. Mol. Biol. 196, 901-917.

Davies J., and L. Riechmann, Affinity improvement of single antibody VH domains: residues in all three hypervariable regions affect antigen binding. Immunotechnology 2 (1996) 169-179

De Kruif, J., and Logtenberg, T. (1996) J. Biol. Chem. 271, 7630-7634.

Demeule, M.; Currie, J. C.; Bertrand, Y.; Che, C.; Nguyen, T.; Regina, A.; Gabathuler, R.; Castaigne, J. P.; Beliveau, R. Involvement of the low-density lipoprotein receptor-related protein in the transcytosis of the brain delivery vector angiopep-2, J. Neurochem. 2008, 106, 1534-1544.

Dumoulin, M., Conrath, K., Van Meirhaighe, A., Meersman, F., Heremans, K., Frenken, L. G., Muyldermans, S., Wyns, L., and Matagne, A. (2002) Protein Sci 11, 500-515.

Durocher, Y., S. Perret, et al. (2002). "High-level and high-throughput recombinant protein production by transient transfection of suspension-growing human 293-EBNA1 cells." Nucleic Acids Res 30(2): E9.

Doyle, P. J., Arbabi-Ghahroudi, M., Gaudette, N., Furzer, G., Savard, M. E., Gleddie, S., McLean, M. D., MacKenzie, C. R., and Hall, J. C. (2008) Mol. Immunol. 45, 3703-3713.

Eisenberg, D., Schwarz, E., Komaromy, M., and Wall, R. (1984) J. Mol. Biol. 179, 125-142

Erdlenbruch B, Alipour M, Fricker G, Miller D S, Kugler W, Eibl H, Lakomek M (2003) Alkylglycerol opening of the blood-brain barrier to small and large fluorescence markers in normal and C6 glioma-bearing rats and isolated rat brain capillaries. Br J Pharmacol. 140(7):1201-10.

Fenner, L., Widmer, A. F., Goy, G., Rudin, S., and Frei, R. (2008) J. Clin. Microbiol. 46, 328-330.

Gaillet, B., Gilbert, R., Broussau, S., Pilotte, A., Malenfant, F., Mullick, A., Gamier, A., and Massie, B. (2010) Biotechnol Bioeng 106, 203-215.

Gan Y, Jing Z, Stetler R A, Cao G (2013) Gene delivery with viral vectors for cerebrovascular diseases. Front Biosci (Elite Ed). 5:188-203. Review.

Garberg, P.; Ball, M.; Borg, N.; Cecchelli, R.; Fenart, L.; Hurst, R. D.; Lindmark, T.; Mabondzo, A.; Nilsson, J. E.; Raub, T. J.; Stanimirovic, D.; Terasaki, T.; Oberg, J. O.; Osterberg, T. In vitro models for the blood-brain barrier, Toxicol. In Vitro 2005, 19, 299-334.

Gergov, M.; Ojanpera, I.; Vuori, E. Simultaneous screening for 238 drugs in blood by liquid chromatography-ion spray tandem mass spectrometry with multiple-reaction monitoring, J. Chromatogr. B Analyt. Technol. Biomed. Life Sci. 2003, 795, 41-53.

Gaillet B, Gilbert R, Amziani R, Guilbault C, Gadoury C, Caron A W, Mullick A, Garnier A, Massie B (2007) High-level recombinant protein production in CHO cells using an adenoviral vector and the cumate gene-switch. Biotechnol Prog. January-23(1):200-9

Gottesman et al., Ann. Rev. Biochem., 62, 385-427 (1993)

Hamers-Casterman, C., Atarhouch, T., Muyldermans, S., Robinson, G., Hamers, C., Songa, E. B., Bendahman, N., and Hamers, R. (1993) Nature 363, 446-448.

Haqqani A S, Caram-Salas N, Ding W, Brunette E, Delaney C E, Baumann E, Boileau E, Stanimirovic D (2012) Multiplexed evaluation of serum and CSF pharmacokinetics of brain-targeting single-domain antibodies using a NanoLC-SRM-ILIS method. Mol Pharm. 2013 May 6; 10(5):1542-56.

Hargreaves K M, Troullos E S, Dionne R A, Schmidt E A, Schafer S C, Joris J L (1988) Bradykinin is increased during acute and chronic inflammation: therapeutic implications. Clin Pharmacol Ther. 44(6):613-21.

Huang Y L, Säljö A, Suneson A, Hansson H A (1995) A new approach for multiple sampling of cisternal cerebrospinal fluid in rodents with minimal trauma and inflammation. J Neurosci Methods. 63(1-2):13-22.

Hussack, G., Hirama, T., Ding, W., MacKenzie, R., and Tanha, J. (2011) PLoS ONE 6, e28218.

Hussack G, Arbabi-Ghahroudi M, van Faassen H, Songer J G, Ng K K, MacKenzie R, Tanha J (2011b) Neutralization of Clostridium difficile toxin A with single-domain antibodies targeting the cell receptor binding domain. J Biol Chem. 286(11): 8961-76.

Iqbal U. Abulrob A. Stanimirovic D B (2011) Integrated platform for brain imaging and drug delivery across the blood-brain barrier. Methods Mol. Biol. 686, 465-481.

Iqbal, U., Trojahn, U., Albaghdadi, H., Zhang, J., O'Connor, M., Stanimirovic, D., Tomanek, B., Sutherland, G., and Abulrob, A. (2010) Br. J. Pharmacol. 160, 1016-1028.

Jespers, L., Schon, O., Famm, K., and Winter, G. (2004) Nat. Biotechnol. 22, 1161-1165. Kabat E A, Wu T T. Identical V region amino acid sequences and segments of sequences in antibodies of different specificities. Relative contributions of VH and VL genes, minigenes, and complementarity-determining regions to binding of antibody-combining sites. J Immunol. 1991; 147:1709-19.

Kim, D. Y., Kandalaft, H., Ding, W., Ryan, S., van Fassen, H., Hirama, T., Foote, S. J., MacKenzie, R., and Tanha, J. (2012) PEDS advance access Aug. 30, 2012, 1-9.

Kornhuber M E, Kornhuber J, Cimniak U (1986) A method for repeated CSF sampling in the freely moving rat. J Neurosci Methods. 17(1):63-8.

Lefranc, M.-P. et al., (2003) Dev. Comp. Immunol., 27, 55-77.

Li S, Zheng W, Kuolee R, Hirama T, Henry M, Makvandi-Nejad S, Fjallman T, Chen W, Zhang J. Pentabody-mediated antigen delivery induces antigen-specific mucosal immune response. Mol Immunol 2009; 46:1718-26.

Merritt, E. A., and Hol, W. G. (1995) Curr. Opin. Struct. Biol. 5, 165-171.

Muruganandam A, Tanha J, Narang S, Stanimirovic D (2001) Selection of phage-displayed llama single-domain antibodies that transmigrate across human blood-brain barrier endothelium. FASEB J. 2002 February; 16(2):240-2.

Musher, D. M., Manhas, A., Jain, P., Nuila, F., Waqar, A., Logan, N., Marino, B., Graviss, E. A. (2007) J. Clin. Microbiol. 45, 2737-2739.

Nhan T, Burgess A, Cho E E, Stefanovic B, Lilge L, Hynynen K. (2013) Drug delivery to the brain by focused ultrasound induced blood-brain barrier disruption: Quantitative evaluation of enhanced permeability of cerebral vasculature using two-photon microscopy. J Control Release. 172(1):274-280.

Nicaise M, Valeio-Lepiniec M, Minard P, Desmadril M. (2004) Affinity transfer by CDR grafting on a nonimmunoglobulin scaffold. Protein Sci. 13(7): 1882-1891.

Nielsen, U. B., Adams, G. P., Weiner, L. M., and Marks, J. D. (2000) Cancer Res. 60, 6434-6440.

Nirogi, R.; Kandikere, V.; Mudigonda, K.; Bhyrapuneni, G.; Muddana, N.; Saralaya, R.; Benade, V. (2009) A simple and rapid method to collect the cerebrospinal fluid of rats and its application for the assessment of drug penetration into the central nervous system, J. Neurosci. Methods, 178, 116-119.

Nuttall, S. D., Krishnan, U. V., Doughty, L., Pearson, K., Ryan, M. T., Hoogenraad, N. J., Hattarki, M., Carmichael, J. A., Irving, R. A., and Hudson, P. J. (2003) Eur. J. Biochem. 270, 3543-3554.

Pardridge, W. M.; Buciak, J. L.; Friden, P. M. Selective transport of an anti-transferrin receptor antibody through the blood-brain barrier in vivo, J. Pharmacol. Exp. Ther. 1991, 259, 66-70.

Pardridge, W. M., Adv. Drug Delivery Reviews, 15, 5-36 (1995)

Pardridge, W. M. Drug and gene delivery to the brain: the vascular route, Neuron. 2002, 36, 555-558.

Planche, T., Aghaizu, A., Holliman, R., Riley, P., Poloniecki, J., Breathnach, A., and Krishna, S. (2008) Lancet Infect. Dis. 8, 777-784.

Preston E, Slinn J, Vinokourov I, Stanimirovic D. (2008) Graded reversible opening of the rat blood-brain barrier by intracarotid infusion of sodium caprate. J Neurosci Methods. 168(2):443-9.

Ridgway, J. B., Presta, L. G., and Carter, P. (1996) Protein Eng. 9, 617-621.

Robertson C R, Flynn S P, White H S, Bulaj G (2011) Anticonvulsant neuropeptides as drug leads for neurological diseases. Nat Prod Rep. 28(4):741-62.

Rüssmann, H., Panthel, K., Bader, R. C., Schmitt, C., and Schaumann, R. (2007) Eur. J. Clin. Microbiol. Infect. Dis. 26, 115-119.

Samani, A. A., Chevet, E., Fallavollita, L., Galipeau, J., and Brodt, P. (2004) Cancer Research 64, 3380-3385.

Samuels B. L., J. Clin. Pharmacol. Ther., 54, 421-429 (1993)

Sloan, L. M., Duresko, B. J., Gustafson, D. R., and Rosenblatt, J. E. (2008) J. Clin. Microbiol. 46, 1996-2001.

Sumbria R K, Zhou Q H, Hui E K, Lu J Z, Boado R J, Pardridge W M. (2013) Pharmacokinetics and brain uptake of an IgG-TNF decoy receptor fusion protein following intravenous, intraperitoneal, and subcutaneous administration in mice. Mol Pharm. 10(4):1425-31.

Tanha, J., Muruganandam, A., and Stanimirovic, D. (2003) Methods Mol. Med. 89, 435-449.

To, R., Hirama, T., Arbabi-Ghahroudi, M., MacKenzie, R., Wang, P., Xu, P., Ni, F., and Tanha, J. (2005) J. Biol. Chem. 280, 41395-41403.

Turgeon, D. K., Novicki, T. J., Quick, J., Carlson, L., Miller, P., Ulness, B., Cent, A., Ashley, R., Larson, A., Coyle, M., Limaye, A. P., Cookson, B. T., and Fritsche, T. R. (2003) J. Clin. Microbiol. 41, 667-670.

Watanabe, T., Acta Oncol., 34, 235-241 (1995)

Xiao G, Gan L S. (2013) Receptor-mediated endocytosis and brain delivery of therapeutic biologics. Int J Cell Biol. doi: 10.1155/2013/703545. Epub 2013 Jun. 11. Yaksh T L, Rudy T A (1976) Chronic catheterization of the spinal subarachnoid space. Physiol Behav. 17(6):1031-6.

Yu, Y. J.; Zhang, Y.; Kenrick, M.; Hoyte, K.; Luk, W.; Lu, Y.; Atwal, J.; Elliott, J. M.; Prabhu, S.; Watts, R. J.; Dennis, M. S. Boosting brain uptake of a therapeutic antibody by reducing its affinity for a transcytosis target, Sci. Transl. Med. 2011, 3, 84ra44.

Zhang, J., Li, Q., Nguyen, T.-D., Tremblay, T.-L., Stone, E., To, R., Kelly, J., and MacKenzie, C. R. (2004a) J. Mol. Biol. 341, 161-169.

Zhang, J., Tanha, J., Hirama, T., Khiew, N. H., To, R., Tong-Sevinc, H., Stone, E., Brisson, J. R., and MacKenzie, C. R. (2004b) J. Mol. Biol. 335, 49-56.

Zhu et al., Immunology and Cell Biology (2010) 88:667-675.

European Patent No. 519596

European Patent No. 626390

U.S. Pat. No. 5,693,761
U.S. Pat. No. 5,766,886
U.S. Pat. No. 5,821,123
U.S. Pat. No. 5,859,205
U.S. Pat. No. 5,869,619
U.S. Pat. No. 6,054,297
U.S. Pat. No. 6,180,370
WO 02/057445
WO 2011/127580
WO 95/04069
WO/2004/076670
WO2003/046560

The invention claimed is:

1. An isolated or purified single domain antibody or antigen-binding fragment thereof, comprising
a complementarity determining region (CDR) 1 sequence of GGTVSPTA (SEQ ID NO:1);
a CDR2 sequence of ITWSRGTT (SEQ ID NO:2); and
a CDR3 sequence of AASTFLRILPEESAYTY (SEQ ID NO:3),
wherein the single domain antibody or antigen-binding fragment thereof is specific for Insulin-Like Growth Factor 1 Receptor (IGF1R).

2. The isolated or purified single domain antibody or antigen-binding fragment thereof of claim 1, comprising the sequence
$X_1VX_2LX_3ESGGGLVQX_4GGSLRLSCX_5X_6SGGTVS$ $PTAMGWX_7RQAPGKX_8X_9EX_{10}VX_{11}HITWSRGT$ $TRX_{12}ASSVKX_{13}RFTISRDX_{14}X_{15}KNTX_{16}YLQM$ $NSLX_{17}X_{18}EDTAVYYCAASTFLRILPEESAYTYW$ $GQGTX_{19}VTVSS$ (SEQ ID NO:4), where $X_1$ is E or Q; $X_2$ is K or Q; $X_3$ is V or E; $X_4$ is A or P; $X_5$ is A or E; $X_6$ is V or A; $X_7$ is V or F; $X_8$ is G or E; $X_9$ is L or R; $X_{10}$ is F or W; $X_{11}$ is G or S; $X_{12}$ is V or Y; $X_{13}$ is D or G; $X_{14}$ is N or S; $X_{15}$ is A or S; $X_{16}$ is L or V; $X_{17}$ is K or R; $X_{18}$ is A or S; and $X_{19}$ is L or Q.

3. The isolated or purified single domain antibody or antigen-binding fragment thereof of claim 1 comprising a sequence selected from the group consisting of:

```
(SEQ ID NO: 5)
QVKLEESGGGLVQAGGSLRLSCEVSGGTVSPTAMGWFRQAPGKEREFVGH
ITWSRGTTRVASSVKDRFTISRDSAKNTVYLQMNSLKSEDTAVYYCAAST
FLRILPEESAYTYWGQGTQVTVSS;

(SEQ ID NO: 6)
QVQLVESGGGLVQPGGSLRLSCAVSGGTVSPTAMGWVRQAPGKGLEWVGH
ITWSRGTTRYASSVKGRFTISRDNSKNTVYLQMNSLRAEDTAVYYCAAST
FLRILPEESAYTYWGQGTLVTVSS;

(SEQ ID NO: 7)
QVQLVESGGGLVQPGGSLRLSCAVSGGTVSPTAMGWFRQAPGKGLEFVGH
ITWSRGTTRYASSVKGRFTISRDNSKNTVYLQMNSLRAEDTAVYYCAAST
FLRILPEESAYTYWGQGTLVTVSS;

(SEQ ID NO: 8)
QVQLVESGGGLVQPGGSLRLSCAVSGGTVSPTAMGWFRQAPGKGLEFVGH
ITWSRGTTRYASSVKGRFTISRDSSKNTVYLQMNSLRAEDTAVYYCAAST
FLRILPEESAYTYWGQGTLVTVSS; and (SEQ ID NO: 9)
QVQLVESGGGLVQPGGSLRLSCAVSGGTVSPTAMGWFRQAPGKEREFVGH
ITWSRGTTRYASSVKGRFTISRDSSKNTVYLQMNSLRAEDTAVYYCAAST
FLRILPEESAYTYWGQGTLVTVSS.
```

4. The isolated or purified single domain antibody or antigen-binding fragment thereof of claim 1, wherein the single domain antibody is of camelid origin.

5. The isolated or purified single domain antibody or antigen-binding fragment thereof of claim 1, wherein the single domain antibody or antigen-binding fragment thereof is in a multivalent display format.

6. The isolated or purified single domain antibody or antigen-binding fragment thereof of claim 5, wherein the single domain antibody or antigen-binding fragment thereof is linked to a Fc fragment.

7. The isolated or purified single domain antibody or antigen-binding fragment thereof of claim 1, wherein the single domain antibody or antigen-binding fragment thereof is immobilized onto a surface.

8. The isolated or purified single domain antibody or antigen-binding fragment thereof of claim 1, wherein the single domain antibody or antigen-binding fragment thereof is linked to a cargo molecule.

9. The isolated or purified single domain antibody or antigen-binding fragment thereof of claim 8, wherein the cargo molecule has a molecular weight in the range of about 1 kD to about 200 kDa.

10. The isolated or purified single domain antibody or antigen-binding fragment thereof of claim 8, wherein the cargo molecule is a detectable agent, a therapeutic, a peptide, a growth factor, a cytokine, a receptor trap, a chemical compound, a carbohydrate moiety, an enzyme, an antibody or fragment thereof, a DNA-based molecule, a viral vector, or a cytotoxic agent; one or more liposomes or nanocarriers loaded with a detectable agent, a therapeutic, a peptide, an enzyme, an antibody or fragment thereof, a DNA-based molecule, a viral vector, or a cytotoxic agent; or one or more nanoparticle, nanowire, nanotube, or quantum dots.

11. A composition comprising one or more than one isolated or purified single domain antibody or antigen-binding fragment thereof of claim 1 and a pharmaceutically-acceptable carrier, diluent, or excipient.

* * * * *